(12) United States Patent
Dykens et al.

(10) Patent No.: US 6,323,039 B1
(45) Date of Patent: Nov. 27, 2001

(54) COMPOSITIONS AND METHODS FOR ASSAYING SUBCELLULAR CONDITIONS AND PROCESSES USING ENERGY TRANSFER

(75) Inventors: James A. Dykens, Encinitas; Gönül Veliçelebi; Soumitra S. Ghosh, both of San Diego, all of CA (US)

(73) Assignee: Mitokor, San Diego, CA (US)

( * ) Notice: Subject to any disclaimer, the term of this patent is extended or adjusted under 35 U.S.C. 154(b) by 0 days.

(21) Appl. No.: 09/338,122

(22) Filed: Jun. 22, 1999

(51) Int. Cl.$^7$ .................................................. G01N 21/76
(52) U.S. Cl. ........................... 436/172; 436/2; 548/405; 548/110; 548/417
(58) Field of Search ........................ 435/5, 6, 7; 436/2, 436/172; 548/405, 110, 417

(56) References Cited

U.S. PATENT DOCUMENTS

| | | |
|---|---|---|
| 4,271,001 | 6/1981 | Imafuku et al. . |
| 4,343,782 | 8/1982 | Shapiro . |
| 5,169,788 | 12/1992 | Chen et al. . |
| 5,459,268 | 10/1995 | Haugland et al. . |
| 5,686,261 | 11/1997 | Zhang et al. . |
| 5,869,689 | 2/1999 | Zhang et al. . |

FOREIGN PATENT DOCUMENTS

WO 96/41166   12/1996   (WO) .

OTHER PUBLICATIONS

Cortese et al., "Novel Flourescence Membrane Fusion Assays Reveal GTP-Dependent Fusogenic Properties of Outer Mitochondrial Membrane-Derived Proteins," *Biochimica et Biophysics Acta*1371: 185–198, 1997.

González and Tsien, "Improved Indicators of Cell Membrane Potential That USe Fluorescence Resonance Energy Transfer," *Chemistry & Biology*4(4): 269–271, 1997.

González and Tsien, "Voltage Sensing by Fluorescence Resonance Energy Transfer in Single Cells," *Biophysical Journal*69: 1272–1280, 1995.

Lemasters et al., "The Mitochondrial Permeability Transition in Cell Death: A Common Mechanism in Necrosis, Apoptosis and Autophagy," *Biochimica et Biophysica Acta*1366: 177–196, 1998.

Rizzuto et al., "Double Labelling of Subcellar Structures With Organelle–Targeted GFP Mutants in vivo," *Current Biology*6(2) 183–188, 1996.

Lakowicz "Principles of Fluorescence Spectroscopy" pp. 303–339, Plenum Press, New York 1983.*

* cited by examiner

Primary Examiner—John S. Brusca
Assistant Examiner—Jeffrey S. Lundgren
(74) Attorney, Agent, or Firm—Seed Intellectual Property Law Group, PLLC

(57) ABSTRACT

The invention provides compositions and methods for monitoring subcellular compartments such as organelles by energy transfer techniques that do not require specific intermolecular affinity binding events between energy transfer donor and energy transfer acceptor molecules. Provided are methods for assaying cellular membrane potential, including mitochondrial membrane potential, by energy transfer methodologies including fluorescence resonance energy transfer (FRET). Diagnostic and drug screening assays are also provided.

54 Claims, 11 Drawing Sheets

DIRECT MEASUREMENT

INDIRECT MEASUREMENT

COMPOSITIONS AND METHODS FOR ASSAYING SUBCELLULAR CONDITIONS AND PROCESSES USING ENERGY TRANSFER

TECHNICAL FIELD

The invention relates generally to biological assays for detecting physiological conditions within cells. More specifically, the invention relates to monitoring molecular interactions in subcellular compartments based on energy transfer from a first compound (the energy transfer donor) to a second compound (the energy transfer acceptor).

BACKGROUND OF THE INVENTION

The cell is the basic unit of life and comprises a variety of subcellular compartments including, for example, the organelles. An organelle is a structural component of a cell that is physically separated, typically by one or more membranes, from other cellular components, and which carries out specialized cellular functions. Organelles and other subcellular compartments vary in terms of, inter alia, their composition and number in cells derived from different tissues, among normal and abnormal cells, and in cells derived from different species. Accordingly, organelles and other subcellular compartments, and macromolecules specifically associated therewith, represent novel targets for the development of agents that specifically impact, respectively, a particular tissue within an animal, abnormal (diseased) but not normal (healthy) cells, or cells from an undesired species but not cells from a desirable species.

For example, members of the Bcl-2 family of proteins (discussed in more detail infra) associate with the outer membranes of mitochondria and with other cellular membranes. The translocation of Bcl-2 proteins from one intracellular position to another occurs during apoptosis, a process by which some abnormal (e.g., pre-cancerous) cells are directed to undergo programmed cell death (PCD), thus eliminating their threat to their host organism. Means for monitoring the accumulation of Bcl-2 proteins in various subcellular compartments, or their translocation from one intracellular location to another, would allow identification of agents designed to impact apoptosis, and to assay the effects of such agents in cells.

As another example, cytoplasmic cellular hybrids (cybrids) comprising the nucleus of one cell type and organelles (mitochondria) from another cell type have been prepared. Experiments with such cybrids have demonstrated that cellular defects associated with diseased cells are transferred with cytoplasmic elements (mitochondria) from diseased cells to cybrids. Diseases that have been demonstrated to have a cytoplasmic component in this manner include Alzheimer's disease and Parkinson's disease (Swerdlow et al., *Neurology* 49:918–925, 1997; Swerdlow et al., *Annals of Neurology* 40:663–671, 1996). Means for monitoring intracellular processes during the formation of cybrids, or for comparing intracellular processes between cybrids that have a common nuclear background but that differ according to the sources of donor cytoplasm as their sources of mitochondria, would allow one to study the mechanisms of such processes and to identify agents that impact such processes.

By way of further example, it is possible to develop antibacterial agents by taking advantage of the fact that bacterial cells comprise structures (e.g., cell walls) that are not present in eukaryotic cells, and by developing agents that specifically impact these structures. In contrast, it has been more difficult to develop agents to treat diseases and disorders resulting from eukaryotic parasites of mammals including humans, in part because of the fact that many cellular features of such parasites have structural similarities to homologous structures found in the host's cells; as a result, any agent that negatively impacts a cellular component of such a parasite is also likely to have a negative effect on the analogous component of the eukaryotic host cells.

There is thus a need for methods and compositions that allow for the rapid and detailed monitoring of processes within subcellular compartments and macromolecules associated therewith. Further, there is a need for methods and compositions for identifying and screening for agents that impact such processes in specific instances.

One objective of the present invention is to provide methods and compositions for monitoring and assaying processes within subcellular compartments and macromolecules associated therewith. When such processes are associated with particular diseases and/or disorders, the invention may be used in a predicative, diagnostic or prognostic modality.

Another objective of the present invention is to provide methods for screening for and identifying agents that impact organelles and other subcellular compartments in specific ways. When such agents are specific for undesirable abnormal cells, or for the cells of an undesirable parasites, they are expected to have remedial, therapeutic, palliative, rehabilitative, preventative, prophylactic or disease-impeditive effects on patients comprising such undesirable cells.

The present invention fulfils these needs and realizes these and other objectives. Other advantages of the invention are apparent from the disclosure.

SUMMARY OF THE INVENTION

The present invention is directed in part to methods and compositions for monitoring cellular processes, conditions and molecules using energy transfer (ET) techniques. Such ET-based methods and compositions further provide means to screen for and identify agents that alter (e.g., increase or decrease) such processes, conditions and molecules. Accordingly, in one aspect the invention provides a method for assaying mitochondrial membrane potential, comprising the steps of contacting a sample comprising one or more mitochondria, simultaneously or sequentially and in either order, with each of a first and a second energy transfer molecule that is not endogenous to the mitochondria, wherein the first and second energy transfer molecules each localize independently of one another to the same submitochondrial site or to acceptably adjacent submitochondrial sites that are mitochondrial outer membrane, mitochondrial inner membrane, mitochondrial intermembrane space or mitochondrial matrix, and wherein the first energy transfer molecule is an energy donor molecule and the second energy transfer molecule is an energy acceptor molecule; exciting the energy donor molecule to produce an excited energy donor molecule; and detecting a signal generated by energy transfer from the first energy transfer molecule to the second energy transfer molecule, wherein the concentration of at least one of the energy transfer molecules in the mitochondria changes as a function of membrane potential.

In certain embodiments of this aspect of the invention the excited energy donor molecule transfers energy to the energy acceptor molecule to produce an excited energy acceptor molecule, and the signal detected results from energy released by the excited energy acceptor molecule. In certain embodiments energy transfer from the first energy transfer molecule to the second energy transfer molecule results in a decrease in the detectable signal. In certain further embodiments the method comprises contacting the mitochondria with an agent that induces dissipation of mitochondrial membrane potential. In certain other embodiments the agent that induces dissipation of mitochondrial membrane potential is an ionophore. In certain further embodiments the method comprises contacting the mitochondria with an agent that induces collapse of mitochondrial membrane potential. In another embodiment the agent that induces collapse of mitochondrial membrane potential is CCCP or FCCP. In certain embodiments the sample is washed prior to the step of detecting a signal, and in other embodiments the signal detected is compared with a reference signal. In certain further embodiments the reference signal is generated by an indicator of cell number, an indicator of mitochondrial mass, an indicator of cellular protein, an indicator of cellular DNA, an indicator of mitochondrial DNA, an indicator of mitochondrial protein and an indicator of fluid volume.

In other embodiments of the invention, the sample comprises one or more mitochondria that are present within at least one cell, and the signal detected is compared with a reference signal. In certain further embodiments the reference signal is generated from a subcellular site that may be a mitochondrial outer membrane, mitochondrial inner membrane, mitochondrial intermembrane space, mitochondrial matrix, cytoplasm, nucleus, nuclear membrane or plasma membrane. In another embodiment the reference signal is generated from extracellular medium. In another embodiment mitochondria are present within at least one cell during at least one step, and in certain further embodiments the cell is an organism, a cultured cell, a cybrid cell, a plant cell or an animal cell. In certain other embodiments the cell is present in a biological sample derived from a multicellular organism, which in some embodiments is a plant cell and in other embodiments an animal cell; in some embodiments the animal is a mammal that in some embodiments is a human. In a further embodiment the human has, is suspected of having or is at risk of having a disease or disorder associated with organellar dysfunction, which in certain further embodiments is mitochondrial dysfunction and in certain other embodiments is lysosomal dysfunction.

In another embodiment of this aspect of the invention, the first energy transfer molecule localizes to a submitochondrial site that is mitochondrial matrix or mitochondrial inner membrane, and the second energy transfer molecule localizes to a submitochondrial site that is mitochondrial matrix or mitochondrial inner membrane. In one embodiment the concentration of the first energy transfer molecule in the submitochondrial site does not change as a function of membrane potential, and the concentration of the second energy transfer molecule in the mitochondrial matrix decreases as a function of membrane potential. In another embodiment the first energy transfer molecule has an excitation maximum at a wavelength of from about 373 nm to about 390 nm, and an emission maximum at a wavelength of from about 400 nm to about 500 nm; and the second energy transfer molecule has an excitation maximum at a wavelength of from about 400 nm to about 500 nm. In a further embodiment the first energy transfer molecule is a fusion protein, wherein the fusion protein comprises a blue-shifted green fluorescent protein polypeptide having a mutation in at least one of Phe-64, Ser-65, Tyr-66, Val-68 and Tyr-145, and a polypeptide sequence that localizes the fusion protein to a submitochondrial site that is mitochondrial matrix or mitochondrial inner membrane; and the second energy transfer molecule is DASPEI, DASPMI, 4-Di-1-ASP, 2-Di-1-ASP, $DiOC_7(3)$, $DiOC_6(3)$, JC-1 or SYTO® 18 yeast mitochondrial stain. In another embodiment the first energy transfer molecule has an excitation maximum at a wavelength of from about 425 nm to about 440 nm, and an emission maximum at a wavelength of from about 450 nm to about 535 nm; and the second energy transfer molecule has an excitation maximum at a wavelength of from about 450 nm to about 530 nm.

In another embodiment the first energy transfer molecule is a fusion protein, wherein the fusion protein comprises a cyan-shifted Green Fluorescent Protein polypeptide having a mutation in at least one of Phe-64, Ser-65, Tyr-66, Asn-146, Met-153, Val-163 and Asn-212, and a polypeptide sequence that localizes the fusion protein to a submitochondrial site selected from the group consisting of mitochondrial matrix and mitochondrial inner membrane; and the second energy transfer molecule is DASPEI, 2-Di-1-ASP, $DiOC_6(3)$, SYTO® 18 yeast mitochondrial stain, rhodamine 6G, JC-1, NBD C6-ceramide or NBD C6-sphingomyelin. In another embodiment the first energy transfer molecule has an excitation maximum at a wavelength of from about 470 nm to about 500 nm, and an emission maximum at a wavelength of from about 505 nm to about 565 nm; and the second energy transfer molecule has an excitation maximum at a wavelength of from about 505 nm to about 565 nm.

In yet another embodiment, the first energy transfer molecule is nonylacridine orange, MitoTracker® Green FM, MitoFluorm™ Green or a fusion protein, wherein the fusion protein comprises a Green Fluorescent Protein polypeptide that is a wildtype Green Fluorescent Protein polypeptide, a red-shifted Green Fluorescent Protein polypeptide having a mutation in one or more of Phe-64, Ser-65, Tyr-66, Gln-69, Ser-72 and Thr-203 or a yellow-shifted Green Fluorescent Protein polypeptide having a mutation in one or more of Phe-64, Ser-65, Tyr-66, Gln-69, Ser-72 and Thr-203, and a polypeptide sequence that localizes the fusion protein to a submitochondrial site that is mitochondrial matrix or mitochondrial inner membrane; and the second energy transfer molecule is rhodamine 123, JC-1, tetrabromorhodamine 123, rhodamine 6G, TMRM, TMRE, tetramethylrosamine or rhodamine B. In another embodiment, the first energy transfer molecule has an excitation maximum at a wavelength of from about 545 to about 560 nm, and an emission maximum at a wavelength of from about 565 to about 625 nm; and the second energy transfer molecule has an excitation maximum at a wavelength of from about 565 to about 625 nm. In an further embodiment the first energy transfer molecule is MitoTracker® Orange CMTMRos; and the second energy transfer molecule is $DiOC_2(5)$. In another embodiment the first energy transfer molecule has an excitation maximum at a wavelength of from about 495 to about 510 nm, and an emission maximum at a wavelength of from about 510 to about 570 nm; and the second energy transfer molecule has an excitation maximum at a wavelength of from about 510 to about 560 nm. In another embodiment the first energy transfer molecule is a fusion protein, wherein the fusion protein comprises a polypeptide sequence that is a FLASH protein sequence or a yellow-shifted Green Fluorescent Protein polypeptide sequence having a mutation in one or more of Ser-65, Tyr-66, Ser-72 and Thr-203, and a polypeptide sequence that localizes the fusion protein to a submitochondrial site that is mitochondrial matrix and mitochondrial inner membrane; and the second energy transfer molecule is JC-1, tetrabromorhodamine 123, rhodamine 6G, TMRM, TMRE, tetramethylrosamine, rhodamine B and 4-dimethylaminotetramethylrosamine.

In another embodiment of this aspect of the invention, a relative amount of the signal generated by energy transfer is detected. In certain other embodiments the signal is detected over a period of time and a rate of change in the signal level is determined, and in certain other embodiments the signal is detected over a period of time and integrated. In another embodiment membrane potential comprises an electric potential, a pH potential, or both. In one embodiment the first and second energy transfer molecules localize to within from about 10 angstroms to about 100 angstroms of each other, and in another embodiment they localize to within from about 10 angstroms to about 50 angstroms of each other and in another embodiment they localize to within from about 20 angstroms to about 50 angstroms of each other. In certain embodiments the signal is generated by fluorescence resonance energy transfer.

Turning to another aspect, the present invention provides a method for identifying an agent that alters mitochondrial membrane potential, comprising the steps of contacting, in the absence and presence of a candidate agent, a sample comprising one or more mitochondria simultaneously or sequentially and in either order with each of a first and a second energy transfer molecule that is not endogenous to the mitochondria, wherein the first and second energy transfer molecules each localize independently of one another to the same submitochondrial site or to acceptably adjacent submitochondrial sites, the sites being mitochondrial outer membrane, mitochondrial inner membrane, mitochondrial intermembrane space or mitochondrial matrix, and the first energy transfer molecule is an energy donor molecule and the second energy transfer molecule is an energy acceptor molecule; exciting the energy donor molecule to produce an excited energy donor molecule; detecting a signal generated by energy transfer from the first energy transfer molecule to the second energy transfer molecule, wherein the concentration of at least one of the energy transfer molecules in the mitochondria changes as a function of membrane potential; and comparing the signal generated in the absence of the candidate agent to the signal generated in the presence of the candidate agent, and therefrom identifying an agent that alters mitochondrial membrane potential.

In another aspect the invention provides a method for identifying a regulator of an agent that alters mitochondrial membrane potential, comprising the steps of contacting, in the absence and presence of a candidate regulator, an agent that alters mitochondrial membrane potential including such an agent identified according to the method provided hereinabove and a sample comprising one or more mitochondria simultaneously or sequentially and in either order with each of a first and a second energy transfer molecule that is not endogenous to the mitochondria, wherein the first and second energy transfer molecules each localize independently of one another to the same submitochondrial site or to acceptably adjacent submitochondrial sites that are mitochondrial outer membrane, mitochondrial inner membrane, mitochondrial intermembrane space or mitochondrial matrix, and the first energy transfer molecule is an energy donor molecule and the second energy transfer molecule is an energy acceptor molecule; exciting the energy donor molecule to produce an excited energy donor molecule; detecting a signal generated by energy transfer from the first energy transfer molecule to the second energy transfer molecule, wherein the concentration of at least one of the energy transfer molecules in the mitochondria changes as a function of membrane potential; and comparing the signal generated in the absence of the candidate regulator to the signal generated in the presence of the candidate regulator, and therefrom identifying a regulator of an agent that alters mitochondrial membrane potential. In one embodiment the regulator is an agonist of the agent that alters mitochondrial potential, and in another embodiment the regulator is an antagonist of the agent that alters mitochondrial potential. In another embodiment the agent that alters mitochondrial membrane potential is an apoptogen. In another embodiment the agent that alters mitochondrial membrane potential is thapsigargin, an ionophore or an excitatory amino acid or derivative thereof. In certain further embodiments the ionophore is ionomycin or A23187. In certain other embodiments the excitatory amino acid or derivative thereof is glutamate, NAAG, NMDA, AMPA, APPA or kainate.

Turning now to another aspect, the invention provides a method for identifying an agent that preferentially alters mitochondrial membrane potential in mitochondria from a first biological source without substantially altering mitochondrial membrane potential in mitochondria from a second biological source, comprising the steps of contacting, in the absence and presence of a candidate agent, each of a first and a second biological sample comprising one or more mitochondria simultaneously or sequentially and in either order with each of a first and a second energy transfer molecule that is not endogenous to the mitochondria, wherein the first sample is derived from a first biological source and the second sample is derived from a second biological source that is distinct from the first biological source, the first and second energy transfer molecules each localize independently of one another to the same submitochondrial site or to acceptably adjacent submitochondrial sites that are mitochondrial outer membrane, mitochondrial inner membrane, mitochondrial intermembrane space or mitochondrial matrix, and the first energy transfer molecule is an energy donor molecule and the second energy transfer molecule is an energy acceptor molecule; exciting the energy donor molecule to produce an excited energy donor molecule in the presence of each of the first and second samples; detecting a signal generated by energy transfer from the first energy transfer molecule to the second energy transfer molecule in the presence of each of the first and second samples, wherein the concentration of at least one of the energy transfer molecules in the mitochondria changes as a function of membrane potential; and comparing the signal generated in the presence of each of the first and second samples in the absence of the candidate agent to the signal generated in the presence of each of the first and second samples in the presence of the candidate agent, and therefrom identifying an agent that preferentially alters mitochondrial membrane potential In one embodiment the first and second biological sources are distinct biological species, and in another embodiment the first biological source is a mammal suspected of having, diagnosed as having or predisposed to having a disease, and the second biological source is a mammal that is not suspected of having and has not been diagnosed as having or predisposed to having the disease. In a further embodiment the first biological source is a human and the second biological source is a human. In another embodiment the disease is Alzheimer's disease, Parkinson's disease or type II diabetes.

The present invention provides, in another aspect, a method for identifying an agent that preferentially alters mitochondrial membrane potential in mitochondria from a first biological sample without substantially altering mitochondrial membrane potential in mitochondria from a second biological sample, comprising the steps of contacting, in the absence and presence of a candidate agent, each of a first and a second biological sample comprising one or more mitochondria simultaneously or sequentially and in either order with each of a first and a second energy transfer molecule that is not endogenous to the rnitochondria, wherein the first sample is derived from a first tissue and the second sample is derived from a second tissue that is distinct from the first tissue, the first and second energy transfer molecules each localize independently of one another to the same submitochondrial site or to acceptably adjacent submitochondrial sites that are mitochondrial outer membrane, mitochondrial inner membrane, mitochondrial intermembrane space or mitochondrial matrix, and the first energy transfer molecule is an energy donor molecule and the second energy transfer molecule is an energy acceptor molecule; exciting the energy donor molecule to produce an excited energy donor molecule in the presence of each of the first and second samples; detecting a signal generated by energy transfer from the first energy transfer molecule to the second energy transfer molecule in the presence of each of the first and second samples, wherein the concentration of at least one of the energy transfer molecules in the mitochondria changes as a function of membrane potential; and comparing the signal generated in the presence of each of the first and second samples in the absence of the candidate agent to the signal generated in the presence of each of the first and second samples in the presence of the candidate agent, and therefrom identifying an agent that preferentially alters mitochondrial membrane potential. In one embodiment the first tissue and the second tissues are derived from the same subject, while in another embodiment the first and second tissues are each derived from a subject of the same species. In another embodiment the first and second tissues are derived from subjects of distinct species.

It is still another aspect of the invention to provide a method of detecting the fusion of a first mitochondrion and a second mitochondrion, comprising the steps of contacting a first sample comprising one or more mitochondria with a first energy transfer molecule that is not endogenous to the mitochondria; contacting a second sample comprising one or more mitochondria with a second energy transfer molecule that is not endogenous to the mitochondria; wherein the first and second energy transfer molecules each localize independently of one another to the same submitochondrial site or to acceptably adjacent submitochondrial sites that are mitochondrial outer membrane, mitochondrial inner membrane, mitochondrial intermembrane space or mitochondrial matrix, and the first energy transfer molecule is an energy donor molecule and the second energy transfer molecule is an energy acceptor molecule; contacting the first sample with the second sample under conditions and for a time sufficient to permit mitochondrial fusion; exciting the energy donor molecule to produce an excited energy donor molecule; and detecting a signal generated by energy transfer from the first energy transfer molecule to the second energy transfer molecule, and therefrom determining fusion of the first mitochondrion and the second mitochondrion.

The invention provides, in another aspect, a method of identifying an agent that alters the fusion of mitochondria, comprising the steps of contacting a first sample comprising one or more mitochondria with a first energy transfer molecule that is not endogenous to the mitochondria; contacting a second sample comprising one or more mitochondria with a second energy transfer molecule that is not endogenous to the mitochondria; wherein the first and second energy transfer molecules each localize independently of one another to the same submitochondrial site or to acceptably adjacent submitochondrial sites that are mitochondrial outer membrane, mitochondrial inner membrane, mitochondrial intermembrane space or mitochondrial matrix, and the first energy transfer molecule is an energy donor molecule and the second energy transfer molecule is an energy acceptor molecule; contacting, in the absence and presence of a candidate agent, the first sample with the second sample under conditions and for a time sufficient to permit mitochondrial fusion; exciting the energy donor molecule to produce an excited energy donor molecule; detecting a signal generated by energy transfer from the first energy transfer molecule to the second energy transfer molecule; and comparing the signal detected in the absence of the candidate agent to the signal detected in the presence of the candidate agent, and therefrom identifying an agent that alters the fusion of the mitochondria. In certain embodiments the agent increases mitochondrial membrane potential, in certain other embodiments the agent dissipates mitochondrial membrane potential, in certain other embodiments the agent collapses mitochondrial membrane potential, and in certain embodiments the agent alters an equilibrium distribution of at least one ionic species on either side of a cellular membrane. In a further embodiment the ionic species is $Ca^{+2}$ and the cellular membrane is a mitochondrial membrane. In certain embodiments the agent that collapses mitochondrial membrane potential is an apoptogen, and in certain other embodiments the agent that collapses mitochondrial membrane potential interacts with an adenine nucleotide translocator, and in certain other embodiments the agent that collapses mitochondrial membrane potential is atractyloside, carboxyatractyloside, bongkrekic acid or isobongkrekic acid.

Turning to another aspect, the invention provides a reagent for measuring mitochondrial $\Delta\psi$ mitochondrial membrane potential, comprising a FRET donor molecule and a FRET acceptor molecule, wherein the accumulation of at least one of the molecules in mitochondria is dependent on $\Delta\psi$ and the accumulation of the other of the molecules in mitochondria is independent of $\Delta\psi$. In one embodiment the molecule that accumulates in mitochondria independent of $\Delta\psi$ is NAO, MitoTracker® Green FM, MitoFluorm™, DAPI, or a fusion protein comprising a polypeptide that is a red-shifted Green Fluorescent Protein polypeptide, a yellow-shifted Green Fluorescent Protein polypeptide or a "FLASH" polypeptide, and a polypeptide sequence that localizes the fusion protein to the mitochondrial matrix or inner membrane. In certain other embodiments the molecule that accumulates in mitochondria in a manner dependent on $\Delta\psi$ is TMRM, TMRE, rhodamine 123, ethidum bromide, 4-Di-1-ASP, 2-Di-1-ASP or DASPEI. The invention also provides, in certain embodiments, a kit comprising the reagent just described and ancillary reagents for measuring mitochondrial $\Delta\psi$.

It is another aspect of the present invention to provide a method for assaying cellular membrane potential, comprising the steps of: contacting a sample comprising at least one cellular membrane, simultaneously or sequentially and in either order, with each of a first and a second energy transfer molecule that is not endogenous to the sample, wherein the first and second energy transfer molecules each localize independently of one another to the same membrane site or to acceptably adjacent membrane sites such that at least one of the energy transfer molecules localizes to a cellular membrane that forms a subcellular compartment, and the first energy transfer molecule is an energy donor molecule and the second energy transfer molecule is an energy acceptor molecule; exciting the energy donor molecule to produce an excited energy donor molecule; and detecting a signal generated by energy transfer from the first energy transfer molecule to the second energy transfer molecule, wherein the concentration of at least one of the energy transfer molecules in the membrane site changes as a function of membrane potential. In one embodiment the first energy transfer molecule localizes to a first membrane site that is mitochondria, endoplasmic reticulum, Golgi, lysosome or plasma membrane and the second energy transfer molecule localizes to the same membrane site or to an acceptably adjacent membrane site that is mitochondria, endoplasmic reticulum, Golgi, lysosome or plasma membrane. In another embodiment the concentration of the first energy transfer molecule in the first membrane site does not change as a function of membrane potential, and the concentration of the second energy transfer molecule in the membrane site decreases as a function of membrane potential.

In one embodiment the first energy transfer molecule has an excitation maximum at a wavelength of from about 373 nm to about 390 nm, and an emission maximum at a wavelength of from about 400 nm to about 500 nm; and the second energy transfer molecule has an excitation maximum at a wavelength of from about 400 nm to about 500 nm. In a further embodiment the first energy transfer molecule has an excitation maximum at a wavelength of from about 425 nm to about 440 nm, and an emission maximum at a wavelength of from about 450 nm to about 535 nm; and the second energy transfer molecule has an excitation maximum at a wavelength of from about 450 nm to about 530 nm. In another embodiment the first energy transfer molecule has an excitation maximum at a wavelength of from about 470 nm to about 500 nm, and an emission maximum at a wavelength of from about 505 nm to about 565 nm; and the second energy transfer molecule has an excitation maximum at a wavelength of from about 505 nm to about 565 nm. In another embodiment the first energy transfer molecule has an excitation maximum at a wavelength of from about 545 to about 560 nm, and an emission maximum at a wavelength of from about 565 to about 625 nm; and the second energy transfer molecule has an excitation maximum at a wavelength of from about 565 to about 625 nm.

In yet another aspect, the invention provides a method for identifying an agent that alters a cellular membrane potential, comprising the steps of contacting, in the absence and presence of a candidate agent, a sample comprising one or more cellular membranes simultaneously or sequentially and in either order with each of a first and a second energy transfer molecule that is not endogenous to the sample, wherein the first and second energy transfer molecules each localize independently of one another to the same membrane site or to acceptably adjacent membrane sites such that at least one of the energy transfer molecules localizes to a cellular membrane that forms a subcellular compartment, and the first energy transfer molecule is an energy donor molecule and the second energy transfer molecule is an energy acceptor molecule; exciting the energy donor molecule to produce an excited energy donor molecule; detecting a signal generated by energy transfer from the first energy transfer molecule to the second energy transfer molecule, wherein the concentration of at least one of the energy transfer molecules in the subcellular compartment changes as a function of membrane potential; and comparing the signal generated in the absence of the candidate agent to the signal generated in the presence of the candidate agent, and therefrom identifying an agent that alters cellular membrane potential.

Another aspect of the invention is to provide a method for identifying a regulator of an agent that alters cellular membrane potential, comprising the steps of contacting, in the absence and presence of a candidate regulator, an agent that alters a cellular membrane potential (which may be an agent identified according to the method just described) and a sample comprising one or more cellular membranes simultaneously or sequentially and in either order with each of a first and a second energy transfer molecule that is not endogenous to the sample, wherein the first and second energy transfer molecules each localize independently of one another to the same membrane site or to acceptably adjacent membrane sites such that at least one of the energy transfer molecules localizes to a cellular membrane that forms a subcellular compartment, and the first energy transfer molecule is an energy donor molecule and the second energy transfer molecule is an energy acceptor molecule; exciting the energy donor molecule to produce an excited energy donor molecule; detecting a signal generated by energy transfer from the first energy transfer molecule to the second energy transfer molecule, wherein the concentration of at least one of the energy transfer molecules in the subcellular compartment changes as a function of membrane potential; and comparing the signal generated in the absence of the candidate regulator to the signal generated in the presence of the candidate regulator, and therefrom identifying a regulator of an agent that alters cellular membrane potential.

In another aspect the invention provides a method for identifying an agent that preferentially alters a cellular membrane potential in a membrane from a first biological source without substantially altering cellular membrane potential in a membrane from a second biological source, comprising the steps of contacting, in the absence and presence of a candidate agent, each of a first and a second biological sample comprising one or more cellular membranes simultaneously or sequentially and in either order with each of a first and a second energy transfer molecule that is not endogenous to the sample, wherein the first sample is derived from a first biological source and the second sample is derived from a second biological source that is distinct from the first biological source, the first and second energy transfer molecules each localize independently of one another to the same membrane site or to acceptably adjacent membrane sites such that at least one of the energy transfer molecules localizes to a cellular membrane that forms a subcellular compartment, and the first energy transfer molecule is an energy donor molecule and the second energy transfer molecule is an energy acceptor molecule; exciting the energy donor molecule to produce an excited energy donor molecule in the presence of each of the first and second samples; detecting a signal generated by energy transfer from the first energy transfer molecule to the second energy transfer molecule in the presence of each of the first and second samples, wherein the concentration of at least one of the energy transfer molecules in the subcellular compartment changes as a function of membrane potential; and comparing the signal generated in the presence of each of the first and second samples in the absence of the candidate agent to the signal generated in the presence of each of the first and second samples in the presence of the candidate agent, and therefrom identifying an agent that preferentially alters cellular membrane potential Turning to another aspect, the invention provides a method for identifying an agent that preferentially alters a cellular membrane potential in a membrane from a first biological sample without substantially altering a cellular membrane potential in a membrane from a second biological sample, comprising the steps of contacting, in the absence and presence of a candidate agent, each of a first and a second biological sample comprising one or more cellular membranes simultaneously or sequentially and in either order with each of a first and a second energy transfer molecule that is not endogenous to the sample, wherein the first sample is derived from a first tissue and the second sample is derived from a second tissue that is distinct from the first tissue, the first and second energy transfer molecules each localize independently of one another to the same membrane site or to acceptably adjacent membrane sites such that at least one of the energy transfer molecules localizes to a cellular membrane that forms a subcellular compartment, and the first energy transfer molecule is an energy donor molecule and the second energy transfer molecule is an energy acceptor molecule; exciting the energy donor molecule to produce an excited energy donor molecule in the presence of each of the first and second samples; detecting a signal generated by energy transfer from the first energy transfer molecule to the second energy transfer molecule in the presence of each of the first and second samples, wherein the concentration of at least one of the energy transfer molecules in the subcellular compartment changes as a function of membrane potential; and comparing the signal generated in the presence of each of the first and second samples in the absence of the candidate agent to the signal generated in the presence of each of the first and second samples in the presence of the candidate agent, and therefrom identifying an agent that preferentially alters a cellular membrane potential.

In still another aspect the invention provides a method for detecting a specific type of cell in a sample, comprising the steps of contacting a sample comprising one or more mitochondria simultaneously or sequentially and in either order with each of a first and a second energy transfer molecule that is not endogenous to the mitochondria, wherein the first and second energy transfer molecules each localize independently of one another to the same subcellular site or to acceptably adjacent subcellular sites, and the first energy transfer molecule is an energy donor molecule and the second energy transfer molecule is an energy acceptor molecule; exciting the energy donor molecule to produce an excited energy donor molecule; and detecting a signal generated by energy transfer from the first energy transfer molecule to the second energy transfer molecule, wherein at least one of the energy transfer molecules preferentially accumulates in the specific type of cell; wherein the signal correlates with the presence of the specific type of cell in the sample. In one embodiment the method further comprises the step of comparing the signal generated in the sample with the signal generated from a control sample lacking the specific type of cell. In another embodiment the specific type of cell is a cancer cell.

In another aspect the invention provides a method for identifying a $\Delta\psi_m$ stabilizing agent, comprising the steps of contacting, in the absence and presence of a candidate $\Delta\psi_m$ stabilizing agent, an agent that alters $\Delta\psi_m$ and a sample comprising one or more mitochondria simultaneously or sequentially and in either order with each of a first and a second energy transfer molecule that is not endogenous to the mitochondria, wherein the first and second energy transfer molecules each localize independently of one another to the same submitochondrial site or to acceptably adjacent submitochondrial sites that are mitochondrial outer membrane, mitochondrial inner membrane, mitochondrial intermembrane space or mitochondrial matrix, and the first energy transfer molecule is an energy donor molecule and the second energy transfer molecule is an energy acceptor molecule; exciting the energy donor molecule to produce an excited energy donor molecule; detecting a signal generated by energy transfer from the first energy transfer molecule to the second energy transfer molecule, wherein the concentration of at least one of the energy transfer molecules in the mitochondria changes as a function of membrane potential; and comparing the signal generated in the absence of the candidate $\Delta\psi_m$ stabilizing agent, to the signal generated in the presence of the candidate $\Delta\psi_m$ stabilizing agent, and therefrom identifying $\Delta\psi_m$ stabilizing agent. In one embodiment the mitochondria are contained within cells, and in a further embodiment the agent that alters $\Delta\psi_m$ is an agent that increases the level of cytosolic Ca2+. In another embodiment the agent that increases the level of cytosolic Ca2+ is a calcium ionophore or thapsigargin. In another embodiment the cells comprise one or more types of glutamate receptors. In another further embodiment the agent that increases the level of cytosolic Ca2+ is an excitatory amino acid or a derivative thereof. In another further embodiment the excitatory amino acid or derivative thereof is glutamate, NAAG, NMDA, AMPA, APPA or kainate. In another embodiment the invention provides a $\Delta\psi_m$ stabilizing agent identified according to the method just described. In another embodiment, the invention provides a method of treating stroke comprising administering the $\Delta\psi_m$ stabilizing agent to a patient in need thereof.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 3 shows representative data from FRET-based assays of $\Delta\psi_m$.

SYMBOLS AND ABBREVIATIONS

Figure 1A:
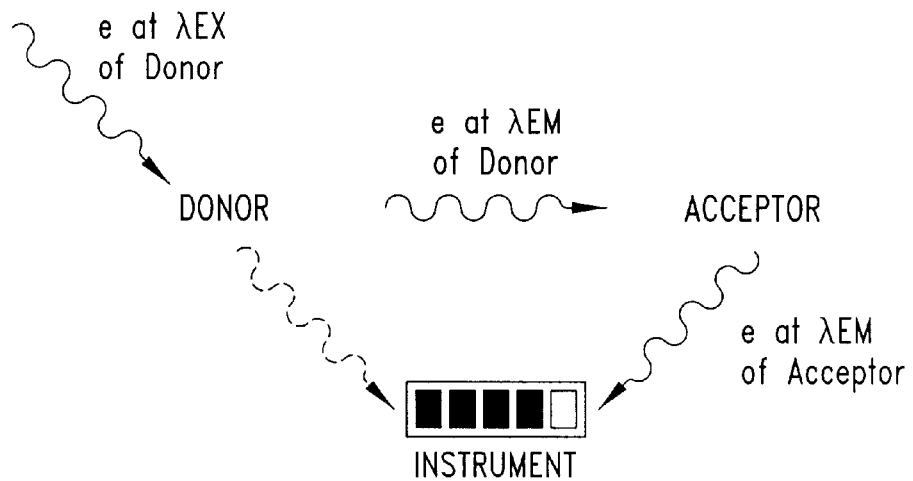
FIG. 1 schematically depicts direct and indirect methods for measuring energy transfer. Symbols: "$\lambda_{EX}$," peak excitation wavelength; "$\lambda_{EM}$," peak emission wavelength; "e," energy; open box, receptive filter setting; closed box, closed filter setting.

Descriptions of specialized terms and abbreviations are listed in Table 1. Unless otherwise, indicated, symbols for nucleotides and amino acids are as described in 37 § C.F.R. 1.821.

| Term or Abbreviation (if any) | Description or Formula | If Chemical or Instrument: Name of Supplier(s)* |
|---|---|---|
| $\Delta\psi$, $\Delta\psi m$ | mitochondrial membrane potential | — |
| $\Delta pH$ | pH potential | — |
| A-23187 | 1-(4,5-dimethoxy-2-nitrophenyl)ethyl ester | Calbiochem |
| 4-BA | 4-bromo A-23187 | Calbiochem |
| ANT | adenine nucleotide translocator | — |
| AO | acridine orange | MP |
| ATR | atractyloside | Sigma |
| BKA | bongkrekic acid | Biomol, Calbiochem |
| — | BODIPY ® TR ceramide | MP |
| — | BODIPY ® FL $Br_2$ $C_5$-ceramide | MP |
| — | BODIPY ® FL $C_5$-ceramide | MP |
| — | BODIPY ® FL $C_5$-sphingomyelin | MP |
| — | BODIPY ® FL conjugate isomer 1 | MP |
| BFA | brefeldin A from *Penicillium brefeldianum* | MP |
| calcein | (a.k.a. fluorexon, fluorescein complexion) | MP, Sigma |
| CATR | carboxyatractyloside | Calbiochem |
| CO-Fluro | 5-carboxyfluorescein | MP |
| CCCP | carbonyl cyanide m-chlorophenyl-hydrazone | Sigma |
| CsA | cyclosporin A | Calbiochem |
| DAPI | 4',6-diamidino-2-phenylindole | MP |
| DASPEI | 2-(4-(dimethylamino)styryl)-N-ethylpyridinium iodide | MP |
| DASPMI | dimethylaminostyrylmethylpyridinium iodide; comprises 2 isomers, 2-Di-1-ASP and 4-Di-1-ASP | MP |
| 2-Di-1-ASP | 2-(4-(dimethylamino)styryl)-N-methylpyridmium iodide | MP |
| 4-Di-1-ASP | 4-(4-(dimethylamino)styryl)-N-methylpyridmium iodide | MP |
| $DilC_{16}(3)$ | 1,1'-dihexadecyl-3,3,3',3'-tetramethyl-indocarbocyanine perchlorate | MP |
| $DilC_{18}(3)$ | 1,1'-dioctadecyl-3,3,3',3'-tetramethyl-indocarbocyanine perchlorate | MP |
| — | 4-dimethylamino-tetramethylrosamine | MP |
| $DiOC_2(5)$ | 3,3'-diethyloxadicarbocyanine iodide | MP |
| $DiOC_5(3)$ | 3,3'-dipentyloxacarbocyanine iodide | MP |
| $DiOC_6(3)$ | 3,3'-dihexyloxadicarbocyanine iodide | MP |
| $DiOC_7(3)$ | 3,3'-diheptyloxadicarbocyanine iodide | MP |
| EtBr | ethidium bromide | Sigma |
| ET | energy transfer | — |
| ETC | electron transport chain | — |
| FCCP | carbonyl cyanide p-(trifluoromethoxy)phenyl-hydrazone | Sigma |
| FLASH | fluorescein arsenical helix binder | — |
| FLIPR ™ | Fluorometric Imaging Plate Reader | Mol. Dev. |
| FRET | fluorescence resonance energy transfer | — |
| FUN-1 ™ | (proprietary compound) | MP |
| | hydroxystilbamidine, methanesulfonate | MP |
| JC-1 | 5,5',6,6'-tetrachloro-1,1',3,3'-tetra-ethylbenzimidazoylcarbocyanine iodide | MP |
| lucigenin | bis-N-methylacridinium nitrate | MP |
| LysoSensor ™ s | (proprietary compounds) | MP |
| LysoTracker ™s | (proprietary compounds) | MP |
| MELAS | Mitochondrial Encephalopthy, Lactic Acidosis and Stroke | — |

-continued

| Term or Abbreviation (if any) | Description or Formula | If Chemical or Instrument: Name of Supplier(s)* |
|---|---|---|
| MixCon | Mixed Controls (cybrids) | — |
| MPP+ | 1-methyl-4-phenylpyridinium | Calbiochem, RBI |
| MPT | Mitochondrial Permeability Transition | — |
| mtDNA | mitochondrial DNA | — |
| MitoFluor ™s | (proprietary compounds) | MP |
| MitoTracker ®s | (proprietary compounds) | MP |
| NAO | 10-N-nonyl acridine orange | MP |
| — | NBD $C_6$-ceramide | MP |
| — | NBD $C_6$-sphingomyelin | MP |
| — | oligomycin | Calbiochem |
| PI | propidium iodide | Sigma |
| PMF | protonmotive force | — |
| rh123 | rhodamine 123 | MP, Calbiochem |
| rhB | rhodamine B | MP |
| rh6G | rhodamine 6G | MP |
| RR | ruthenium red (ammoniated ruthenium oxychloride) | Sigma |
| SNAFL® calcein | seminapthofluorescein calcein | MP |
| SYTO®18 | (proprietary compound) | MP |
| TB-rh123 | tetrabromorhodamine 123 | MP |
| TMRE | tetramethylrhodamine, ethyl ester | MP |
| TMRM | tetramethylrhodamine, methyl ester | MP |
| — | tetramethylrosamine | MP |
| — | 4-dimethylaminotetramethylrosamine | MP |
| — | thapsigargin | Calbiochem |
| — | valinomycin | Calbiochem |
| Green Fluorescent Proteins | | vectors from Aurora/Clontech |
| GFP | green fluorescent protein | — |
| BFP | blue-shifted green fluorescent protein | — |
| CFP | cyan-shifted green fluorescent protein | — |
| RFP | red-shifted green fluorescent protein | — |
| YFP | yellow-shifted green fluorescent protein | — |

*Abbreviations for suppliers: "Calbiochem", Calbiochem, Inc., La Jolla, CA; "MP," Molecular Probes, Inc., Eugene, OR; "Biomol," Biomol Research :Laboratories, Inc., Plymouth Meeting, MA; "Mol. Dev.," Molecular Devices, Sunnyvale, CA; "Aurora," Aurora Biosciences Corp., San Diego, CA; "Clontech," CLONTECH Laboratories, Inc., Palo Alto, CA; "Sigma," Sigma Chemical Co., St. Louis, MO; RBI, Research Biochemicals International, Natick, MA.

DETAILED DESCRIPTION OF THE INVENTION

The present invention pertains in part to the use of intermolecular energy transfer to monitor intracellular and intraorganellar conditions. In particular, the invention derives from the unexpected observation that such intracellular and intraorganellar conditions can be surveyed using energy transfer molecule donor-acceptor pairs that need not undergo specific intermolecular recognition events such as affinity binding interactions. Rather, according to the present disclosure, under particular naturally occurring or artificially induced intracellular and/or intraorganellar physiologic conditions, appropriately paired energy transfer donor and acceptor molecules can be selected that accumulate at acceptably adjacent sites as provided herein, to generate detectable signals.

By way of background, energy transfer (ET) is generated from a resonance interaction between two molecules: an energy-contributing "donor" molecule and an energy-receiving "acceptor" molecule. Energy transfer can occur when (1) the emission spectrum of the donor overlaps the absorption spectrum of the acceptor and (2) the donor and the acceptor are within a certain distance (for example, less than about 10 nm) of one another. The efficiency of energy transfer is dictated largely by the proximity of the donor and acceptor, and decreases as a power of 6 with distance. Measurements of ET thus strongly reflect the proximity of the acceptor and donor compounds, and changes in ET sensitively reflect changes in the proximity of the compounds such as, for example, association or dissociation of the donor and acceptor.

According to the present invention, both energy transfer molecules, the ET donor molecule and the ET acceptor molecule, are molecules that are not endogenous to the sample as provided herein (by way of non-limiting example, a cell, an organelle such as a mitochondrion, or a subcellular or suborganellar compartment) with which they are contacted. The donor and acceptor compounds may co-localize to a subcellular compartment in such a manner as to achieve sufficient proximity to one another for a particular type of energy transfer to occur. In certain aspects of the invention, such co-localization may be dependent upon, or may be disrupted by, intracellular processes or responses to chemical agents. For instance, such processes or responses can lead to, respectively, an increase or a decrease in energy transfer that can be detected, for example, by detecting a signal. Thus, for example, detection of the degree or rate of energy transfer between the ET donor and ET acceptor molecules may provide in pertinent part a method for assaying a given intracellular process or response. In certain preferred embodiments the invention provides a method for assaying a cellular membrane potential, and in certain other preferred embodiments the invention provides a method for assaying mitochondrial membrane potential.

It is therefore an aspect of the invention to provide a method for assaying a cellular membrane potential, in pertinent part, by contacting a sample comprising one or more cellular membranes with an ET donor and an ET acceptor molecule, exciting the ET donor to produce an excited ET donor molecule and detecting a signal generated by energy transfer from the ET donor to the ET acceptor. The sample may be contacted with the ET donor and the ET acceptor simultaneously, or it may be contacted with the ET donor and the ET acceptor sequentially and in either order, depending on the particular donor and acceptor being used. Optionally, the sample may be washed under suitable conditions prior to the step of detecting a signal, for example to improve sensitivity for detecting the signal. Those having ordinary skill in the art can readily determine the manner by which the sample is contacted, in view of the properties of the sample and of the ET molecules selected, and in view of the teachings provided herein. As also provided herein, the subject invention method can employ any suitable ET donor molecule and ET acceptor molecule that can function as a donor-acceptor pair. As discussed in greater detail below, the method of the present invention may be used to identify an agent that alters a cellular membrane potential, or to identify a molecule that is a regulator of such an agent.

In certain preferred embodiments the invention is directed to a method for assaying mitochondrial membrane potential, wherein neither the ET donor molecule nor the ET acceptor molecule is endogenous to mitochondria, and wherein the ET donor and the ET acceptor each localize independently of one another to the same submitochondrial site or to acceptably adjacent submitochondrial sites as provided herein.

Optionally, in preferred embodiments the ET donor molecule and the ET acceptor molecule may both be light emission molecules, for example fluorescent, phosphorescent, or chemiluminescent molecules or the like, which emit a detectable signal in the form of light when excited by excitation light of an appropriate wavelength. Preferred ET donor-acceptor combinations that can be used according to the present invention are fluorescent donors with fluorescent or phosphorescent acceptors, or phosphorescent donors with phosphorescent or fluorescent acceptors. "Fluorescence" refers to luminescence (emission of light) that is caused by the absorption of radiation at one wavelength ("excitation"), followed by nearly immediate re-radiation ("emission"), usually at a different wavelength, that ceases almost at once when the incident radiation stops. At a molecular level, fluorescence occurs as certain compounds, known as fluorophores, are taken from a ground state to a higher state of excitation by light energy; as the molecules return to their ground state, they emit light, typically at a different wavelength. "Phosphorescence," in contrast, refers to luminescence that is caused by the absorption of radiation at one wavelength followed by a delayed re-radiation that occurs at a different wavelength and continues for a noticeable time after the incident radiation stops. "Chemniluminescence" refers to luminescence resulting from a chemical reaction, and "bioluminescence" refers to the emission of light from living organisms or cells, organelles or extracts derived therefrom.

Figure 1B:
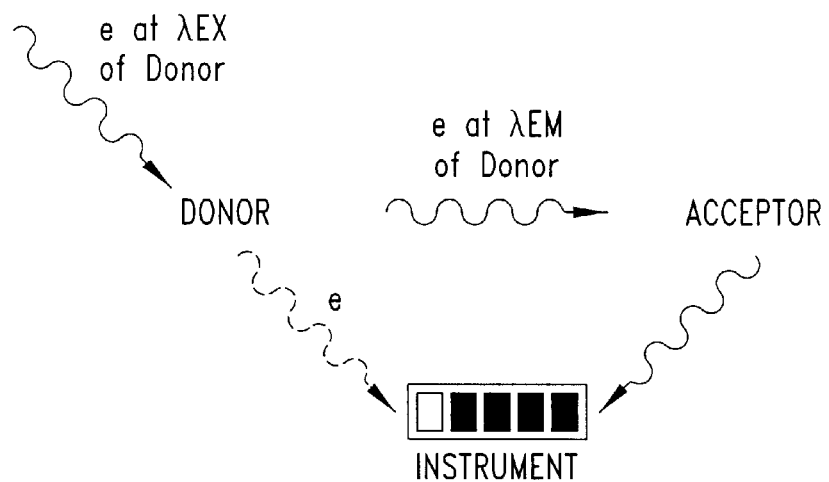

In certain preferred embodiments, a detectable signal that is generated by energy transfer between ET donor and acceptor moleclues results from fluorescence resonance energy transfer (FRET). FRET occurs within a molecule, or between two different types of molecules, when energy from an excited donor fluorophore is transferred directly to an acceptor fluorophore (for a review, see Wu et al., *Analytical Biochem.* 218:1–13, 1994). In general, the energy transfer from an excited fluorophore (e.g., an ET donor molecule) to an absorber (e.g., an ET acceptor molecule) is measured by (1) measuring the spectra (including changes in the spectra) of fluorescence from the energy donor molecule and the energy acceptor molecule; (2) measuring the speed at which the intensity of the fluorescent intensity of the energy donor molecule decreases after pulse-laser excitation (i.e., the fluorescence lifetime); or (3) measuring the reduction in intensity of fluorescence from the energy donor compound (i.e., indirect measurement of FRET), or the increase in intensity of fluorescence from the energy acceptor compound (i.e., direct measurement of FRET). Direct measurement of energy transfer involves monitoring the signal from an excited energy acceptor molecule, which increases as the ET compounds achieve proximity to each other, whereas indirect measuring of energy transfer involves monitoring a signal from an excited ET donor molecule that decreases (i.e., that is quenched) as the compounds achieve proximity (FIG. 1).

The use of FRET to monitor specific intermolecular and/or intramolecular interactions that involve specific inter- and intramolecular recognition events (including associative and dissociative events, e.g., affinity and binding interactions) that bring ET donor and ET acceptor fluorophores into close proximity with one another, is known in the art. When measuring such intermolecular interactions, the ET donor and acceptor fluorophores are typically situated on two different molecules that are known or believed to enter into close association with each other. On the other hand, when intramolecular interactions are measured, the ET donor and acceptor fluorophores are present on the same molecule.

In contrast to such known uses of FRET methodologies, wherein ET donor and acceptor fluorophores are brought into proximity with each other through known specific molecular interactions, the present invention is based on the unexpected observation that energy transfer can occur between ET donor and ET acceptor fluorophores that are brought into proximity with one another by virtue of their having selectively concentrated or accumulated in a common subcellular compartment, for example, an organelle, a sub organellar site or other subcellular locale. As a result, the present invention can be used to monitor a variety of conditions or processes within, or associated with, such subcellular compartments.

As provided herein, contemplated uses of the invention include but need not be limited to (i) monitoring conditions and processes within subcellular compartments, (ii) monitoring interactions between pairs of macromolecules found within or associated with such subcellular compartments, (iii) identifying agents that influence subcellular compartments and/or intracellular processes in a species-specific manner, and (iv) identifying agents that influence subcellular compartments and/or intracellular processes in such a manner as to treat diseases and disorders of mammals and other animals, including humans, and plants. Each of these uses is described in greater detail below.

Typically, the invention relates in part to a method for assaying a sample, which in preferred embodiments is a biological sample and in particularly preferred embodiments is a biological sample containing one or more mitochondria. In other preferred embodiments the biological sample contains one or more cellular membranes, including the plasma membrane and intracellular membrane bounded compartments such as endosomes, lysosomes, peroxisomes, mitochondria, chloroplasts, endocytic and secretory vesicles, ER-Golgi constituents, organelles and the like. Biological samples may be provided by obtaining a blood sample, biopsy specimen, tissue explant, organ culture or any other tissue or cell preparation from a subject or a biological source. The subject or biological source may be a human or non-human animal, a plant, a unicellular or a multicellular organism, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like.

In certain embodiments of the invention, the subject or biological source may be suspected of having or being at risk for having a disease associated with organellar dysfunction including altered mitochondrial function and mitochondrial dysfunction, and in certain embodiments of the invention, the subject or biological source may be known to be free of a risk or presence of such a disease. Organellar dysfunction may further include abnormal, supranormal, inefficient, ineffective or deleterious activity at the organelle level, for example, defects in uptake, release, activity, sequestration, transport, metabolism, catabolism, synthesis, storage or processing of biological molecules and macromolecules such as proteins and peptides and their derivatives, carbohydrates and oligosaccharides and their derivatives including glycoconjugates such as glycoproteins and glycolipids, lipids, nucleic acids and cofactors including ions, mediators, precursors, catabolites and the like. Examples of organellar dysfunction may include, but need not be limited to, lysosomal storage defects such as the mucopolysaccaridoses, I-cell disease, Wolman disease and cholesteryl ester storage disease (e.g., Du et al., 1998 *Mol. Genet. Metab.* 64:126–34); plasma membrane defects such as ion channel dysfunction in cystic fibrosis; endoplasmic reticulum storage diseases (e.g., Kim and Arvan, 1998 *Endocr. Rev.* 19:173–202); diseases associated with Golgi defects (e.g., ALS, AD, Gonatas et al., 1998 *Histochem. Cell. Biol.* 109:591–600) and other types of organellar dysfunction that are known to those familiar with the art.

In certain preferred embodiments it may be desirable to compare the signal detected according to the method of the invention with a reference signal. Selection of a suitable reference signal will according to criteria with which those having ordinary skill in the art will be familiar, and may vary depending on the particular cellular membrane being assayed and upon the particular donor-acceptor pair employed. For example, a reference signal may be generated by a reference compound such as an ET donor or ET acceptor molecule or a distinct reporter molecule that is an indicator as provided herein, and may further be generated in the absence or presence of a sample. Such reporter molecules or indicators may include a detectable compound that can be detected as indicative of one or more of a quantity of a detectable component or a location of a detectable component, or the like. For example, by way of illustration and not limitation, a reference signal may be generated by a reporter molecule that permits normalization of a detected energy transfer signal according to the number of cells present (e.g., the reporter may be any of numerous known indicators of cell number, such as selective stains for cell nuclei, for example, propidium iodide or ethidium bromide).

In certain other embodiments, the reference signal is generated by an indicator of the mitochondrial mass, the mitochondrial number or the mitochondrial volume present. For example, where an indicator of mitochondrial mass is selected, a reporter molecule such as nonylacridine orange (which can also be an ET donor) may be employed. Methods for quantifying mitochondrial mass, volume and/or mitochondrial number are known in the art, and may include, for example, quantitative staining of a representative biological sample. Typically, quantitative staining of mitochondrial may be performed using organelle-selective probes or dyes, including but not limited to mitochondrion selective reagents such as fluorescent dyes that bind to mitochondrial molecular components (e.g., nonylacridine orange, MitoTrackers™) or potentiometric dyes that accumulate in mitochondria as a function of mitochondrial inner membrane electrochemical potential (see, e.g., Haugland, 1996 *Handbook of Fluorescent Probes and Research Chemicals— Sixth Ed.,* Molecular Probes, Eugene, Oreg.). As another example, mitochondrial mass, volume and/or number may be quantified by morphometric analysis (e.g., Cruz-Orive et al., 1990 *Am. J. Physiol.* 258:L148; Schwerzmann et al., 1986 *J. Cell Biol.* 102:97). These or any other means known in the art for quantifying mitochondrial mass, volume and/or mitochondrial number in a sample are within the contemplated scope of the invention. For example, the use of such quantitative determinations for purposes of calculating mitochondrial density is contemplated and is not intended to be limiting. In certain highly preferred embodiments, mitochondrial protein mass in a sample is determined using well known procedures. For example, a person having ordinary skill in the art can readily prepare an isolated mitochondrial fraction from a biological sample using established cell fractionation techniques, and therefrom determine protein content using any of a number of protein quantification methodologies well known in the art.

In other embodiments, a reference signal may be generated by a reporter molecule that permits normalization of a detected energy transfer signal according to the amount of protein present (e.g., coomassie blue, fluorescamine, bicinchoninic acid) or to the amount of nucleic acid present (e.g., ethidium bromide, acridine orange, methylene blue). As another example, a reference signal may be generated by a detectable reporter molecule that is soluble in a liquid medium containing the sample, but that cannot traverse cellular membranes and so serves as a marker of extracellular medium, for example as an indicator of fluid volume. For example, where extraordinarily sensitive instrumentation (e.g., see infra) may be used to detect ET signals, such an indicator may permit improved quantitative precision by calibration/normalization of sample volumes. Many compounds that are suitable for use as such reference signals will be known to those familiar with the art, who may select such compounds as sources of a reference signal in a manner dependent on, inter alia, the particular cellular membrane potential being assayed and the particular donor-acceptor pair employed.

As used herein, detecting a "relative amount" of a signal may include but is not limited to detecting a signal for purposes of comparing it to a reference signal as provided above. Thus, detecting a relative amount of a signal may refer to detecting only a portion of a signal (e.g., detecting a signal at less than 100% efficiency), or to detecting a signal only a portion of which is generated by energy transfer, or to detecting a portion of a signal relative to a signal detected from another sample such as a control sample, regardless of whether any of such other signals detected are reference signals as provided herein. Detection of a signal according to the methods disclosed herein may include quantification of ET by conventional or arbitrarily assigned units of measure. In certain embodiments, a signal may be detected over a period of time such that one or more behaviors of the signal may be analyzed as a function of time. For instance, in some embodiments described herein, a signal may be detected over a period of time, which refers to any method of detecting a sample in a manner that provides more than a single detection event, such that a correlation of a detected signal with a discrete point in time can be established. Thus, for example, in certain embodiments a change in an amount of a signal may be detected over two or more time points, and a rate of change in the level of signal is determined (e.g., a slope or a rate-of-change of a slope such as a first order derivative is determined, when the signal level is plotted as a function of time). As another example, in certain other embodiments an amount of a signal may be cumulatively determined over a discrete time interval, to provide a summed signal (e.g., an integrated signal). These and other techniques known in the art for analyzing quantitative data, and in particular for analyzing such data having a temporal component, are within the contemplated invention and are described in greater detail below.

Thus, any of the methods provided by the invention can be modified so as to also include a reference signal that correlates with a reference parameter of interest for the purpose of, e.g., standardizing for cell number, quantity of cellular protein or cellular nucleic acids, mitochondrial mass, quantity of mitochondrial protein or mitochondrial nucleic acids, indicator of fluid volume or the like. The reference signal, which can be used as an internal standard, need not result from energy transfer and can involve any signal that can be correlated with the desired reference parameter but which does not interfere with detection of the test/assay signal. In the context of the invention, a reference compound can interfere with the test/assay signal if it generates a signal that cannot be resolved from the test/assay signal, or if it localizes to the same subcellular compartment as the ET donor and acceptor compounds and itself acts as an ET acceptor or donor compound.

An instrument such as FLIPR™ can be set to alternate between reading signals at two different wavelengths with a cycling time of about one second; in this manner, the reference signal and the test/assay signal (e.g., FRET, $\Delta\psi$) can be read over the same time course. However, the reference need not be read at the same time as the test/assay signal. For example, in some aspects of the invention, it is necessary to disrupt the cells in order to detect the reference signal, and this typically necessitates that the reference signal be read after the test or assay has been completed.

Some non-limiting examples of reference signals include the following. After the test or assay, as is known in the art, cellular protein (including mitochondrial protein) can be measured using methods such as the Bradford or Lowry assays, and nucleic acid can be measured via the use of fluroescent dyes such as propidium iodide (PI). Nucleic acids can also be measured in living cells. For example, in digitonin-permeabilized cells, propidium iodide (PI; peak excitation, 536 nm; peak emission, 617 nm when bound to a nucleic acid) binds nuclear and cytoplasmic nucleic acids but cannot access the mitochondrial matrix and the mitochondrial nucleic acids contained therein; PI thus provides a reference signal for quantity of cellular nucleic acids. The permeant compound acridine orange (AO) can be used in living cells to distinguish RNA and DNA as it has distinct excitation/emission spectra depending on the type of nucleic acid to which it is bound (AO:DNA, peak excitation, 500 nm; peak emission, 526 nm; AO:RNA, peak excitation, 460 nm; peak emission, 650 nm). The SYTO stains can also be used to detect nucleic acids in living cells; the manufacturer (Molecular Probes, Inc., Eugene, Oreg.) of the SYTO stains indicates that all of the SYTO stains can access nuclear and cellular nucleic acids and some can also access mitochondrial nucleic acids; one skilled in the art will be able to apply techniques such as, e.g., fluorescent microscopy to determine what types of nucleic acids are detected by the use of a particular SYTO stain. JC-1 green fluorescence and NAO fluorescence can be used to measure mitochondrial mass in living cells (Mancini et al., *Ann. Surg. Oncol.* 5:287–295, 1998; Vayssiere et al., *In Vitro Cell. Dev. Biol.* 28A:763–772, 1992, respectively).

The present invention provides diagnostic and prognostic methods, as well as screening assays, i.e., methods of identifying agents that alter a monitored process or condition, for example mitochondrial membrane potential. Diagnostic uses include methods for assaying a cellular process or condition (e.g., a cellular membrane potential such as mitochondrial membrane potential) wherein a biological sample comprising a cellular membrane or subcellular compartment (e.g., an organelle such as a mitochondrion) is taken from a patient suspected of having or being prone or predisposed to a disease or disorder (e.g., having an increased risk for or probability of developing the disease relative to the risk in a reference population), and wherein further the process or condition may be altered relative to that determined in a control sample derived from a patient known to not have the disease or disorder. Prognostic uses include methods wherein a biological sample comprising a cellular membrane or subcellular compartment is taken from a patient known to have a disease or disorder in which the monitored intracellular process or condition is altered. In such prognostic uses, for example, biological samples from the patient are prepared and tested for their response to agents known to impact the monitored intracellular process or condition in some, but not all, instances. A desired response of the biological sample to a particular agent indicates that the patient from which the sample was taken will respond best to a treatment that correlates with positive response to that treatment. In a related aspect, pharmacogenetic studies using the invention are employed to determine the correlations between different treatments and specific measurements generated by the invention.

Non-limiting examples of diseases or disorders that are thought to involve the altered function or dysfunction of subcellular compartments include Alzheimer's disease, Parkinson's disease, type II diabetes and lysosomal storage disorders. When the subcellular compartment of interest is the mitochondrion, preferred biological samples are cybrids (e.g., cytoplasmic hybrid cells comprising a common nuclear component but having mitochondria derived from different individuals, i.e., patients and controls). Methods for preparing and using cybrids are described in U.S. Pat. No. 5,888,438, published PCT applications WO 95/26973 and WO 98/17826, King and Attardi (*Science* 246:500–503, 1989), Chomyn et al. (*Mol. Cell. Biol.* 11:2236–2244, 1991), Miller et al. (*J. Neurochem.* 67:1897–1907, 1996), Swerdlow et al. (*Annals of Neurology* 40:663–671, 1996), Cassarino et al. (*Biochim. Biophys. Acta* 1362:77–86, 1997), Swerdlow et al. (*Neurology* 49:918–925, 1997), Sheehan et al. (*J. Neurochem.* 68:1221–1233, 1997), and Sheehan et al. (*J. Neurosci.* 17:4612–4622, 1997), all of these being hereby incorporated by reference.

The term "screening" refers to the use of the invention to identify agents that impact the monitored intracellular process or condition in a negative or positive fashion. Cells or organelles are treated with an agent thought to impact the monitored intracellular process or condition, and the response of a subcellular compartment of interest to the agent is monitored and compared to a control sample that has been treated with only the vehicle used to deliver the agent. Agents that impact the monitored intracellular process or condition result in an altered response of the subcellular compartment of interest relative to the response in the control sample. In certain aspects of the invention, agents that act in a species-specific manner are identified by the screening methods of the invention.

The present invention relates to energy transfer between chemically distinct and independent ET donor and acceptor molecules that can occur (i) when both ET donor and ET acceptor molecules are localized to the same subcellular compartment; (ii) when one ET molecule (i.e., the ET donor or the ET acceptor) is localized to a particular subcellular compartment and the other ET molecule (i.e., the ET acceptor or the ET donor) is localized to a membrane that forms one border of that subcellular compartment; or (iii) when one ET molecule (i.e., the ET donor or the ET acceptor) is localized to a subcellular compartment and the other ET molecule (i.e., the ET acceptor or the ET donor) transiently or otherwise associates with that subcellular compartment.

In situation (i), a change in the efficiency and/or rate of energy transfer between the ET donor and acceptor molecules correlates with a change in a condition or the occurrence of a given process within the subcellular compartment of interest. Non-limiting examples of this aspect of the invention, described in greater detail below, include methods for assaying mitochondrial membrane potential ($\Delta\psi$) or pH potential ($\Delta$pH), photosynthesis within chloroplasts, and formation of secondary lysosomes. According to the invention such methods may also be used to detect the presence of specific cell types in a biological sample, when at least one subcellular compartment of a specific cell type accumulates and/or retains the ET donor or acceptor molecule to a greater extent than do other cell types.

In situation (ii), a change in the rate of energy transfer between the ET donor and acceptor molecules correlates with a process that influences the cellular membrane (e.g., alters the membrane potential) containing either the ET donor or ET acceptor molecule, and/or influences the subcellular compartment bounded by the cellular membrane, which compmartment contains the other member (e.g., ET acceptor or donor molecule) of the ET molecule pair. Non-limiting examples of this aspect of the invention, described in more detail herein, include methods for monitoring the mitochondrial pore transition (MPT) and viral uncoating processes.

In situation (iii), a change in the rate of energy transfer between the ET donor and acceptor molecules correlates with the association of a detectably labeled molecule (e.g., labeled with either an ET donor or ET acceptor) with, or its dissociation from, a labeled subcellular compartment (e.g., labeled with either an ET acceptor or ET donor). Non-limiting examples of such embodiments of the invention, described in greater detail below, include methods for monitoring the association of Bcl-2 protein with, or the dissociation of cytochrome c from, the outer mitochondrial membrane.

Donor-Acceptor Pairs

There are provided, according to the present invention, paired ET molecules wherein each pair comprises an ET donor molecule and an ET acceptor molecule. As described herein there are several criteria for determining combinations of energy-donating compounds (ET donor molecules) and energy-accepting compounds (ET acceptor molecules) that are acceptable for ET-based assays of the invention. Additional criteria may specifically apply when the assay is designed to monitor a particular intracellular state or activity such as, for example, mitochondrial inner membrane potential ($\Delta\psi$ or $\Delta\psi$m), association of a particular intracellular molecule or factor with a particular organelle, release of a particular intracellular molecule or factor from an organelle or the like.

One criterion for determining a suitable ET donor-acceptor pair for use according to the present invention is that the energy emission spectrum of the ET donor molecule should at least partially overlap the energy absorption spectrum of the ET acceptor molecule, so that energy transfer from the donor to the acceptor can occur. Typically, an ET donor compound has an emission peak wavelength (herein, "$\lambda D(em)$") that is within several nm of the excitation peak wavelength of the acceptor compound (herein, "$\lambda A(ex)$"). That is, the difference between D(em) and A(ex) is typically from about 70 nm to about 20 nm or less, with typical values for the difference $$\Delta = \lambda D(em) - \lambda A(ex)$$

being $\leq 60$ nm, $\leq 50$ nm, $\leq 40$ nm, $\leq 30$ nm, $\leq 25$ nm, $\leq 20$ nm, $\leq 15$ nm, $\leq 10$ nm, $\leq 5$ nm or $\leq 1$ nm. When excitation or emission is plotted as a function of wavelength, however, certain compounds that are suitable for use as ET donor molecules or ET acceptor molecules may have broad peaks, such that energy may be detectably transferred between certain paired ET donor and ET acceptor molecules having a larger difference between D(em) and A(ex) than that just described. For example, certain donor-acceptor pairs may be suitable for ET methodologies as provided herein even where energy transfer between them is highly inefficient (i.e., where one or both of the ET donor and acceptor may be used with light having a wavelength that is far from the excitation peak wavelength and/or the emission peak wavelength for the ET molecule), so long as the ET donor and the ET acceptor are within sufficient proximity of one another for detectable energy transfer to occur. Those having ordinary skill in the art can readily determine without undue experimentation when fluorescence resonance energy transfer is present, such that selection of appropriate ET donor-acceptor pairs may be accomplished according to established criteria and the teachings provided herein.

For example, routine screening may be employed by combining in solution (e.g., in the absence of a biological sample) at least a candidate ET donor molecule and a candidate ET acceptor molecule as disclosed herein, for purposes of determining whether a detectable FRET signal can be generated. For certain donor-acceptor combinations, selective accumulation of one or both of the donor and acceptor in a subcellular compartment may depend on binding of the donor and/or the acceptor to a molecule present in the subcellular compartment, and for other donor-acceptor pairs accumulation in such compartments may not involve such binding. Thus, screening of certain donor-acceptor pairs for their facilitation of a detectable FRET signal in solution may include adding to the solution at least one suitable biomolecule such as a protein- or peptide-, a lipid-, a nucleic acid- or a carbohydrate-containing species that will be selected by the person having ordinary skill in the art based upon familiarty with the nature of the donor and/or the acceptor and/or the properties of a subcellular compartment in a contemplated biological sample to be used in the subject invention method. Without wishing to be bound by theory, in order to detect a FRET signal the concentrations of the ET donor and acceptor molecules used in such a pilot experiment may in certain such instances exceed those to be used in the subject invention methods as provided herein. However, similarly detectable concentrations of such ET molecules may accumulate in a sample subcellular compartment as described herein, even where substantially lower concentrations of ET molecules are initially contacted with the sample. Those familiar with the art will also readily appreciate that the fluorescence spectral properties of ET donor and ET acceptor molecules may vary as a function of solution and sample conditions employed (e.g., solvent selected, solvent and ionic strength, pH, nature of the sample, etc.).

Another criterion useful in selecting a suitable ET donor-acceptor pair for use according to the present invention is that the emission signal from the excited ET acceptor compound must be capable of being distinguished from the emission signal from the excited ET donor compound. An emission signal from an excited donor can be so distinguished if, for example, (1) the wavelength of the emission signal from the excited acceptor is sufficiently distinct from the wavelength of the emission signal from the excited donor or (2) the acceptor quenches the emission signal from the excited donor.

A variety of classes of compounds can serve as ET acceptor molecules and ET donor molecules according to the present invention, and the acceptor and donor can, but need not, belong to the same class of compound. For instance, a fluorescent protein might serve as an ET donor molecule for an ET acceptor that is a small organic compound, or to an acceptor that is a different fluorescent protein, so long as other criteria necessary for the assay are satisfied. Table 1 lists, among other things, abbreviations for ET donor and acceptor compounds, and Table 2 lists some ET donor-acceptor pairings that are appropriate for ET-based assays (with the exception of the various Green Fluorescent Protein derivatives, most of the compounds listed in Table 2 are available from Molecular Probes, Inc., Eugene, Oreg.).

TABLE 2

Donor-Acceptor Pairs for ET-Based Assays

| | DONORS | | | ACCEPTORS | |
|---|---|---|---|---|---|
| Compound | Peak Excitation Wavelength | Peak Emission Wavelength | Peak Excitation Wavelength | Peak Emission Wavelength | Compound |
| Group I | 373–388 nm | 400–500 nm | Suitable for Use with Any Group I Donor: | | |
| BFP-F64L/S65T/Y66H/Y145F | 380 nm | 440 nm | 433 nm | 475 nm (501 nm)* | CFP-F64L/S65T/Y66W/N146I/M153T/V163A/N212L |
| BFP-Y66H/Y145F | 381 nm | 445 nm | | | |
| BFP-Y66H | 382 nm | 448 nm | 461 nm | 585 nm | 2-Di-1-ASP |
| BFP-F64M/Y66H/V68I | 385 nm | 450 nm | 461 nm | 589 nm | DASPEI |
| LysoTracker ™ Yellow DND-22 | 373 nm | 422 nm | 470 nm* | 510 nm | wildtype GFP |
| LysoSensor ™ Yellow DND-192 | 374 nm | 424 nm | 466 nm | 536 nm | NBD $C_6$-ceramide |
| LysoSensor ™ Yellow DND-167 | 373 nm | 425 nm | 466 nm | 536 nm | NBD $C_6$-sphingomyelin |
| | | | 475 nm | 605 nm | 4-Di-1-ASP |
| | | | 442 nm | 505 nm | LysoSensor ™ Green DND-153 |
| | | | 443 nm | 505 nm | LysoSensor ™ Green DND-189 |
| | | | 479 nm | 507 nm | RFP-S65C |
| | | | 482 nm | 504 nm | $DiOC_7(3)$ |
| | | | 483 nm | (none) | SYTO ® 18 |
| | | | 484 nm | 501 nm | $DiOC_6(3)$ |
| | | | 484 nm | 500 nm | $DiOC_5(3)$ |
| | | | 488 nm | 507 nm | RFP-F64L/S65T |
| | | | 489 nm | 511 nm | RFP-S65T |
| | | | 490 nm | 509 nm | RFP-F64MI S65G/Q69L |
| | | | 485–585 nm | 590 nm | JC-1 aggregates** |
| Group IIA | 360–375 nm | 465–560 nm | Suitable for Use with Any Group IIA, IIB or IIC Donor: | | |
| DAPI | 365 nm | 520 nm | 466 nm | 536 nm | NBD $C_6$-ceramide |
| hydroxystilbamidine, methanesulfonate | 361 nm | 536 nm | 466 nm | 536 nm | NBD $C_6$-sphingomyelin |
| Group IIB | 390–405 nm | 465–560 nm | 475 nm | 605 nm | 4-Di-1-ASP |
| wildtype GFP | 395 nm (470 nm)* | 510 nm | 483 nm | (none) | SYTO ® 18 |
| | | | 484 nm | 500 nm | $DiOC_5(3)$ |
| | | | 502 nm | 512 nm | YFP-S6SG/Y66W/572A/T203Y |

TABLE 2-continued

Donor-Acceptor Pairs for ET-Based Assays

| | DONORS | | | ACCEPTORS | |
|---|---|---|---|---|---|
| Compound | Peak Excitation Wavelength | Peak Emission Wavelength | Peak Excitation Wavelength | Peak Emission Wavelength | Compound |
| | | | 503 nm | 510 nm | Brefeldin A, BODIPY ® FL conjugate isomer 1 |
| Group IIC | 445–460 nm | 465–560 nm | 507 nm | 529 nm | rhodamine 123 |
| Lucigenin | 455 nm | 505 nm | 510 nm | 527 nm | JC-1 monomers** |
| | | | 505 nm | 511 nm | BODIPY ® FL C$_5$-ceramide |
| | | | 505 nm | 512 nm | BODIPY ® FL C$_5$-sphingomyelin |
| | | | 489 nm | 520 nm | acridine orange |
| | | | 504 nm | 511 nm | LysoTracker ™ Green DND-26 |
| | | | 508 nm | (none) | FUN-1 ™ |
| | | | 532 nm | 545 nm | LysoTracker ™ Green Br$_2$ |
| | | | 534 nm | 551 nm | LysoTracker ™ Yellow DND-68 |
| | | | 541 nm | 640 nm | Neutral Red |
| | | | 528 nm | 551 nm | rhodamine 6G |
| | | | 524 nm | 550 nm | tetrabromorhodamine 123 |
| | | | 528 nm | 551 nm | rhodamine 6G |
| | | | 533 nm | 545 nm | BODIPY ® FL Br$_2$ C$_5$-ceramide |
| | | | 546 nm | 590 nm | ethidium bromide |
| | | | 549 nm | 565 nm | DilC$_{18}$(3) |
| | | | 549 nm | 565 nm | DilC$_{16}$(3) |
| | | | 485–585 nm | 590 nm | JC-1 aggregates** |
| | | | 559 nm | 568 nm | Brefeldin A, BODIPY FL 558/568 conjugate isomer 1 |
| Group III | 425–440 nm | 450–535 nm | Suitable for Use with Any Group III Donor: | | |
| CFP-F64L/ S65T/Y66W/ N146I/M153T/ V163A/N212L | 433 nm 501 nm* | 475 nm | 461 nm | 585 nm | 2-Di-1-ASP |
| | | | 461 nm | 589 nm | DASPEI |
| | | | 466 nm | 536 nm | NBD C$_6$-ceramide |
| | | | 466 nm | 536 nm | NBD C$_6$-sphingomyelin |
| | | | 483 nm | (none) | SYTO ® 18 |
| | | | 484 nm | 500 nm | DiOC$_5$(3) |
| | | | 484 nm | 501 nm | DiOC$_6$(3) |
| | | | 485–585 nm | 590 nm | JC-1 aggregates** |
| | | | 489 nm | 520 nm | acridine orange |
| | | | 502 nm | 512 nm | YFP-S65G/Y66W/ S72A/T203Y |
| | | | 503 nm | 510 nm | Brefeldin A, BODIPY ® FL conjugate isomer 1 |
| | | | 504 nm | 511 nm | LysoSensor ™ Green DND-26 |
| | | | 505 nm | 511 nm | BODIPY ® FL C$_5$-ceramide |
| | | | 505 nm | 512 nm | BODIPY ® FL C$_5$-sphingomyelin |
| | | | 508 nm | (none) | FUN-1 ™ |
| | | | 528 nm | 551 nm | rhodamine 6G |
| | | | 532 nm | 545 nm | LysoSensor ™ Green Br$_2$ |
| | | | 534 nm | 551 nm | LysoTracker ™ Yellow DND-68 |
| | | | 541 nm | 640 nm | Neutral red |
| Group IV | 470–500 nm | 505–565 nm | Suitable for Use with Any Group IV Donor: | | |
| RFP-S65C | 479 nm | 507 nm | 507 nm | 529 nm | rhodamine 123 |
| RFP-F64L/S65T | 488 nm | 507 nm | 510 nm | 527 nm | JC-1 monomers** |

TABLE 2-continued

Donor-Acceptor Pairs for ET-Based Assays

| | DONORS | | ACCEPTORS | | |
|---|---|---|---|---|---|
| Compound | Peak Excitation Wavelength | Peak Emission Wavelength | Peak Excitation Wavelength | Peak Emission Wavelength | Compound |
| RFP-S65T | 489 nm | 511 nm | 524 nm | 550 nm | tetrabromorhodamine 123 |
| MitoFlour ™ Green | 489 nm | 517 nm | 528 nm | 551 nm | rhodamine 6G |
| RFP-F64M/ S65G/Q69L | 490 nm | 509 nm | 548 nm | 573 nm | TMRM |
| MitoTracker ® Green FM | 490 nm | 516 nm | 549 nm | 574 nm | TMRE |
| NAO | 495 nm | 519 nm | 550 nm | 574 nm | tetramethylrosamine |
| wildtype GFP | 470 nm* | 510 nm | 556 nm | 578 nm | rhodamine B |
| acridine orange | 489 nm | 520 nm | 505 nm | 511 nm | BODIPY ® FL $C_5$-ceramide |
| | | | 505 nm | 512 nm | BODIPY ® FL $C_5$-sphingomyelin |
| | | | 508 nm | (none) | FUN-1 ™ |
| | | | 533 nm | 545 nm | BODIPY ® FL $Br_2$ $C_5$-ceramide |
| | | | 534 nm | 551 nm | LysoTracker ™ Yellow DND-68 |
| | | | 541 nm | 640 nm | Neutral red |
| | | | 549 nm | 565 nm | $DilC_{18}(3)$ |
| | | | 549 nm | 565 nm | $DilC_{16}(3)$ |
| | | | 559 nm | 568 nm | Brefeldin A, BODIPY FL 558/568 conjugate isomer 1 |
| Group V | 495–509 nm | 511–570 nm | Suitable for Use with Any Group V Donor: | | |
| YFP-S65G/ Y66W/S72A/ T203Y | 502 nm | 512 nm | 510 nm | 527 nm | JC-1 monomers** |
| | | | 524 nm | 550 nm | tetrabromorhodamine 123 |
| "FLASH" proteins | 508 nm | 528 nm | 528 nm | 551 nm | rhodamine 6G |
| | | | 533 nm | 545 nm | BODIPY ® FL $Br_2$ $C_5$-ceramide |
| | | | 534 nm | 551 nm | LysoTracker ™ Yellow DND-68 |
| | | | 541 nm | 640 nm | Neutral red |
| | | | 548 nm | 573 nm | TMRM |
| | | | 549 nm | 574 nm | TMRE |
| | | | 549 nm | 565 nm | $DilC_{18}(3)$ |
| | | | 549 nm | 565 nm | $DilC_{16}(3)$ |
| | | | 550 nm | 574 nm | tetramethylrosamine |
| | | | 556 nm | 578 nm | rhodamine B |
| | | | 556 nm | 585 nm | 4-dimethylamino-tetramethylrosamine |
| | | | 559 nm | 568 nm | Brefeldin A, BODIPY FL 558/568 conjugate isomer 1 |
| Group VI | 545–560 nm | 565–625 nm | Suitable for Use with Any Group VI Donor: | | |
| MitoTracker ® Orange CMTMRos | 551 | 576 | 579 nm | 601 nm | $DiOC_2(5)$ |
| | | | 589 nm | 617 nm | BODIPY ® TR ceramide |

*Minor excitation or emission peak.
**JC-1 monomers vs. JC-1 aggregates: at higher concentrations (aqueous solutions > 0.1 uM) or in mitochondria with higher potentials, and the "J-aggregates: have different spectral properties than the parent compound.

A variety of small, hydrophilic molecules can serve as ET donor and ET acceptor molecules. Such compounds can be used when it is desired to have a donor and/or acceptor compound undergo energy transfer in a water-based subcellular site or compartment. It may be desired in some aspects of the invention to have such compounds preferentially accumulate in a water-based subcellular site or compartment. Some such compounds are known to preferentially accumulate at particular subcellular locations. Additionally or alternatively, a moiety that directs a compound to a subcellular location can be conjugated to a donor or acceptor moiety in order to generate a donor or acceptor compound capable of preferentially accumulating at the subcellular location of choice. For example, published PCT application WO 98/17826, herein incorporated by reference, describes methods for conjugating mitochondria-directing moieties to various compounds.

Small lipophilic molecules, can be used when it is desired to have a donor and/or acceptor compound preferentially accumulate in a cellular membrane, such membranes typically consisting in significant part of lipid bi-layers. Additionally or alternatively, a lipid or lipophilic molecule can be conjugated to a donor or acceptor moiety in order to generate a donor or acceptor compound capable of preferentially accumulating in a cellular membrane.

Examples of proteins that can serve as donor and acceptor compounds include fusion proteins comprising a "FLASH" (fluorescein arsenical helix binder) sequence (Griffin et al., *Science* 281:269–272, 1998), or an aequorin protein or a green fluorescent protein (Kendall et a., *Trends in Biotechnology* 16:216–224, 1998, and references cited therein). As used herein, the term "green fluorescent protein" encompasses the wildtype green fluorescent protein (wildtype GFP), as well as blue-shifted, cyan-shifted, red-shifted and yellow-shifted derivatives of wildtype GFP (designated, respectively, BFP, CFP, RFP and YFP; see published PCT application WO 98/06737). Table 2 includes descriptions of the amino acid changes in various green fluorescent protein derivatives and the respective excitation and emission peak wavelengths of these GFP derivatives.

In order to generate an expression construct that produces an aequorin, GFP or FLASH fusion protein that accumulates in the organelle or other subcellular site of interest, an expression vector comprising nucleotide sequences appropriate for gene expression can be manipulated to comprise (1) a first nucleic acid encoding a GFP derivative or FLASH polypeptide and (2) a second nucleic acid encoding a peptide sequence that directs a protein to an organelle or other subcellular site of interest (i.e., the "targeting sequence"), wherein the first and second nucleic acids are linked so as to have a common reading frame that comprises both nucleic acids. Such fusion proteins can be directed to a particular membrane within a cell (such as, for example, the nuclear membrane or the inner or outer membrane of organelles such as mitochondria and chloroplasts), or to other specific subcellular locations, depending on the nature of the particular targeting sequence that is used in a given instance. Table 3 lists some non-limiting examples of intracellular sites wherein the donor and acceptor compounds listed in Table 2 accumulate.

TABLE 3

Sites of Localization of Non-Protein Donor and Acceptor Compounds to Subcellular Compartments

| Subcellular Compartment | Compounds |
|---|---|
| Endoplasmic reticulum & Golgi apparatus | BODIPY ® TR ceramide; DiOC$_5$(3); NBD C$_6$-ceramide; NBD C$_6$-sphingomyelin; Brefeldin A; BODIPY ® FL conjugate isomer 1; BODIPY ® FL C$_5$-ceramide; BODIPY ® FL C$_5$- sphingomyelin; BODIPY ® FL Br$_2$C$_5$-ceramide; DilC$_{18}$(3); and DilC$_{16}$(3) |
| Lysosomes & other acidic organelles | acridine orange; FUN-1 ™; hydroxystilbamidine, methanesulfonate; LysoTracker ™s Blue DND-22, Green Br$_2$, Green DND-26, and Yellow DND-68; neutral red; Lysosensor ™s Blue DND-167, Blue DND-192, and Green DND-253 |
| Mitochondria | 2-Di-1-ASP; 4-Di-1-ASP; DASPEI; SYTO ® 18; DiOC$_6$(3); rhodamine 123; tetrabromorhodamine 123; JC-1; ethidium bromide; rhodamine 6G; TMRM; TMRE; tetramethylrosamine; rhodamine B; 4-dimethylamino-tetramethylrosamine; rhodamine 6G; DiOC$_2$(5); also DiOC$_7$(3) (plant mitochondria). |

A further criterion is that the donor and acceptor compounds should accumulate in the subcellular compartment at the same site, which will permit ET to take place, or at acceptably adjacent sites. By "acceptably adjacent" it is meant that such sites are within close enough proximity for ET to occur. Such sites are from about 100 Angstroms (Å) to about 10 Å or less from each other, typically about 80 Å, 60 Å, 50 Å, 40 Å, 30 Å, 25 Å, 20 Å, 15 Å, 10 Å, 5 Å or less from each other, preferably 70 Å or less from each other, more preferably 50 Å or less from each other, and most preferably 40 Å or less from each other, depending on the donor-acceptor pair of compounds. In any event, because the relationship of (i) the distance between an ET donor molecule and an ET donor molecule to (ii) the ability for ET to transpire is well established (see, e.g., Haugland, 1996 *Handbook of Fluorescent Probes and Research Chemicals— Sixth Ed.*, Molecular Probes, Eugene, Oreg.), those familiar with the art will readily appreciate that donor-acceptor intermolecular distance is a cardinal determinative factor for the efficiency of ET.

As a non-limiting example, one subcellular site of interest is the organelle known as the mitochondrion. The mitochondrion comprises an outer membrane that is exposed to the cytoplasm and with which various cytoplasmic factors may transiently or stably associate, an inner membrane, an intermembrane space between the inner and outer membranes, and a matrix (the compartment within the inner membrane), arranged as is shown in FIG. 1. For mitochondria, acceptably adjacent sites include (i) the outer membrane and the cytoplasm, including cytoplasmic factors associated with the outer membrane; (ii) the outer membrane and the intermembrane space; (iii) the intermembrane space and the inner membrane; and (iv) the inner membrane and the matrix, including factors within the matrix.

In the case of mitochondria, by way of example and not limitation, GFP fusion protein derivatives have been targeted to the mitochondrial matrix using cytochrome c oxidase subunit IV protein sequences sequences (Llopis et al., *Proc. Natl. Acad. Sci. U.S.A.* 95:6803–6808, 1993), to the internemebrane space using cytochrome c protein sequences (Mahajan et al., *Nature Biotech.* 16:547–552, 1998), and to the outer membrane of mitochondria using hexokinase (Sui et al., *Arch. Biochem. Biophys.* 345:111–125, 1997), Bcl-2 or Bax (Mahajan et al., *Nature Biotech.* 16:547–552, 1998) protein sequences. GFP fusion proteins have also been targeted to mitochondria using 3-oxoacyl-CoA thiolase (Zhang et al., *Biochem. Biophys. Res. Commun.* 242:390–395, 1998), OSCP (Prescott et al., *FEBS Letts.* 411:97–101, 1997) and BNIP3 (Yasuda et al., *J. Biol. Chem.* 273:12415–12421, 1998) protein sequences. Aequorin fusion protein derivatives have been targeted to mitochondria using cytochrome c oxidase protein sequences (Pinton et al., *Biofactors* 8:243–253, 1998; Rizzuto et al., *Nature* 358:325–327, 1992). Other fusion proteins have been described that target mitochondrial sites using protein sequences from mitochondrial (or bacterial) thiolases (Arakawa et al., *J. Biochem.*, Tokyo, 107:160–164, 1990), FO-ATPase subunit 9 (*J. Biol. Chem.* 271:25208–25212, 1996), manganese superoxide dismutase (Balzan et al., *Proc. Natl Acad. Sci. U.S.A.* 92:4219–4223, 1995), and P-450(SCC) (Kumamoto et al., *J. Biochem.*, Tokyo, 105:72–78, 1989).

In the case of chloroplasts, by way of example and not limitation, fusion proteins have been targeted to the outer membrane by use of the SCE70 heat shock protein targeting sequence (Wu et al., *J. Biol. Chem.* 268:19384–19391, 1993). Other targeting sequences, such as those from the Rieske iron-sulfur protein (Madueno et al., *J. Biol. Chem.* 269:17458–17463, 1994), direct fusion proteins across the thylakoid membrane.

If dual targeting to mitochondria and chloroplasts is desired, some fusion proteins comprising dual targeting sequences have been described (Creissen et al., *Plant J.* 8:167–175, 1995; Huang et al., *Plant Cell* 2:1249–1260, 1990). Conversely, when plant cells are being used and targeting to only mitochondria or chloroplasts is desired, care must be taken to ensure that a dual targeting sequence is not employed.

In the case of the nucleus, by way of example and not limitation, aequorin fusion protein derivatives have been targeted to the nucleus using nucleoplasmin protein sequences (Badminton et al., *J. Biol. Chem.* 271:31210–31214, 1997).

In the case of the endoplasmic reticulum (ER), by way of example and not limitation, aequorin fusion protein derivatives have been targeted to the endoplasmic reticulum using calreticulin protein sequences (Kendall et al., *Biochem. Biophys. Res. Commun.* 189:1008–1016, 1992).

In the case of the Golgi apparatus, by way of example and not limitation, aequorin fusion protein derivatives have been targeted to the Golgi plasma membrane using galactosyltransferase, SNAP-25, connexin and 5-HT$_{1A}$-receptor protein sequences (Burton et al., *Mol Cell. Biol.* 7:419–434, 1996; Marsault et al., *EMBO J.* 16:1575–1581, 1997; Daguzan et al., *Int. J. Dev. Biol.* 39:653–657, 1995). GFP fusion proteins have been targeted to the Golgi apparatus using galactosyltransferase protein sequences (Llopis et al., *Proc. Natl. Acad. Sci. U.S.A.* 95:6803–6808, 1993).

In the case of whole cell assays, another criterion is that the accumulation of ET donor and acceptor molecules should occur preferentially at sites within the mitochondrion or whichever organelle or subcellular compartment is of interest. However, some accumulation of the compounds in other, secondary intracellular sites in acceptable, particularly if the donor and acceptor do not accumulate at the same secondary intracellular site (i.e., so that ET cannot occur in the secondary sites), or if the amount of background ET-derived signal is low enough that events specific to the organelle of interest can be followed despite accumulation (s) of compound(s) at secondary sites. Moreover, most if not all of the assays described herein can be adapted for use with isolated organelles, in which instance preferential accumulation is not a criterion.

Instrumentation for Detecting Energy Transfer

A variety of instruments can be used in methods of the invention to excite a donor compound and to measure emission from an acceptor compound. Which instrument(s) is (are) applicable for a particular donor-acceptor pair depends on factors such as (1) the need to apply energy at a wavelength that will excite the donor compound, preferably at or near $\lambda D(ex)$, to samples; (2) the need to measure energy within the emission spectrum of the acceptor compound, preferably at or near $\lambda A(em)$; (3) the type of samples to be assayed in a given program; and (4) the number of samples to be assayed in a given program.

With regard to factors (1) and (2), the spectra of energy being applied to samples to excite a donor compound, and the spectra of energy being emitted by an excited acceptor compound and measured in samples will determine, in general, what type of instrument will be used. For example, although $\lambda D(em)$ should not be identical to $\lambda A(em)$, the minimal acceptable amount of difference between these two values will be influenced by, among other factors, the instrumentation being used. That is, as $\lambda D(em)$ approaches $\lambda A(em)$, instruments capable of resolving closely-spaced wavelengths are required, and an assay using a donor-acceptor pair wherein the difference between $\lambda D(em)$ and $\lambda A(em)$ is less than about 3 to about 5 nm requires a high resolution instrument. Conversely, an assay using a donor-acceptor pair wherein the difference between $\lambda D(em)$ and $\lambda A(em)$ is greater than about 50 to about 75 nm requires an instrument of medium to low resolution.

With specific regard to factor (2), the type of energy being emitted by an excited acceptor compound and measured in samples will determine, in general, what type of instrument will be used. By definition, a fluorometer is a device that measures fluorescent energy and should therefor be part of the instrumentation. A fluorometer may be anything from a relatively simple, manually operated instrument that accommodates only a few sample tubes at a time, to a somewhat more complex manually operated or robotic instrument that accommodates a larger numbert of samples in a format such as, e.g., a 96-well microplate (such as, e.g., an fmax™ fluorimetric plate reader, Molecular Devices Corp., Sunnyvale, Calif.; or a Cytofluor fluorimetric plate reader, model #2350, Millipore Corp., Bedford, Mass.), or a complex robotic instrument (such as, e.g., a FLIPR™ instrument; see infra) that accommodates a multitude of samples in a variety of formats such as 96-well microplates.

With regard to factor (3), the type of samples to be assayed in a given program, different formats will be appropriate for different types of samples. For example, 96-well microplates are suitable in instances where the cells or isolated organelles of interest adhere to the material of the microplate or to some material applied to the wells of the microplate; however, plastic fluorescence results in a larger background component at excitation wavelengths below about 400 nm. For measurements involving nonadherent cells or organelles, or soluble extracts prepared therefrom, an instrument capable of reading fluorescent signals in glass or polymeric tubes or tubing is preferred. Regardless of what type of format is used, it should allow for the introduction of donor and acceptor compounds, as well as control reagents and compounds being evaluated, into the samples at appropriate points in time.

Factor (4), the number of samples to be assayed in a given program, will influence how automated the instrument will be. For example, when high throughput (HTS) assaying of a large number of samples is desired, robotic or semi-robotic instruments are preferred. However, a fair number of samples can be processed manually, particularly when formats that accommodate large sample numbers (such as, e.g., 96-well microplates) are used.

Depending on the assay, a Fluorometric Imaging Plate Reader (FLIPR™) instrument (Molecular Devices, Sunnyvale, Calif.) is often the instrument of choice for ET-based assays of the invention. The FLIPR™ system (see http://www.moleculardevices.com/pages/flipr.html) has the following desirable features: it uses a combination of a water-cooled, argon-ion laser illumination and cooled CCD camera as an integrating detector that accumulates signal over the period of time in which it is exposed to the image and, as a result, its signal-to-noise characteristics are generally superior to those of conventional imaging optics; it also makes use of a proprietary cell-layer isolation optics that allow signal discrimination on a cell monolayer, thus reducing undesirable extracellular background fluorescence; it provides data in real-time, and can also provide kinetic data (i.e., readings at a multitude of timepoints); it has the ability to simultaneously stimulate and read all 96 wells of a 96-well microplate; it provides for precise control of temperature and humidity of samples during analysis; it includes an integrated state-of-the-art 96-well pipettor, which uses dispensible tips to eliminate carryover between experiments, that can be used to aspirate, dispense and mix precise volumes of fluids from microplates; and, in the case of the FLIPR$^{384}$ instrument, it can be adapted to run sample assays in a robotic or semi-robotic fashion, thus providing for analysis of large numbers of samples in shortest amount of time (e.g., up to about a hundred 96-well microplates per day).

Monitoring Conditions or Processes within Subcellular Compartments

The term "subcellular compartment" refers to any intracellular space that is, for at least some of the time, maintained in an at least partially isolated condition. Some type of physical barrier, typically a bilipid membrane, forms the border between a given subcellular compartment and other cellular components. A border around a subcellular compartment may be permeable, impermeable, or semi-permeable to molecules inside or outside the subcellular compartment. Subcellular compartments include, but are not limited to, known organelles such as, e.g. in a eukaryotic cell, the nucleus, the nucleolus, mitochondria, chloroplasts, endosomes, lysosomes, endoplasmic reticulum, Golgi apparatus, and the like. The present invention can also be used with extracellular subcellular structures that interact with and/or are internalized by cells including, by way of example and not limitation, viruses and other intracellular parasites. Some of the subcellular compartments that can be monitored or assayed using the present invention, and applications particular for each such subcellular compartment, are described in more detail in the following subsections.

Mitochondria

One subcellular compartment of particular interest is the organelle known as the mitochondrion (plural, mitochondria). Mitochondria are the main energy source in cells of higher organisms, and provide direct and indirect biochemical regulation of a wide array of cellular respiratory, oxidative and metabolic processes. These include electron transport chain (ETC) activity, which drives oxidative phosphorylation to produce metabolic energy in the form of adenosine triphosphate (ATP), and which also underlies a central mitochondrial role in intracellular calcium homeostasis.

In addition to their role in energy production in growing cells, mitochondria (or, at least, mitochondrial components) participate in programmed cell death (PCD), also known as apoptosis (Newmeyer et al., 1994, *Cell* 79:353–364; Liu et al., 1996, *Cell* 86:147–157). Apoptosis is apparently required for normal development of the nervous system and functioning of the immune system. Moreover, some disease states are thought to be associated with either insufficient or excessive levels of apoptosis (e.g., cancer and autoimmune diseases in the first instance, and stroke damage and neuro-degeneration in Alzheimer's disease in the latter case). For general reviews of apoptosis, and the role of mitochondria therein, see Green and Reed (1998, *Science* 281:1309–1312), Green (1998, *Cell* 94:695–698) and Kromer (1997, *Nature Medicine* 3:614–620). Thus, agents that affect apoptotic events, including those associated with mitochondrial components, might have a variety of remedial, therapeutic, palliative, rehabilitative, preventative, prophylactic or disease-impeditive uses.

A variety of apoptogens are known to those familiar with the art (see, e.g., Green et al., 1998 *Science* 281:1309 and references cited therein) and may include by way of illustration and not limitation: tumor necrosis factor-alpha (TNF-α); Fas ligand; glutamate; N-methyl-D-aspartate (NMDA); interleukin-3 (IL-3); herbimycin A (Mancini et al., 1997 *J. Cell Biol.* 138:449–469); paraquat (Costantini et al., 1995 *Toxicology* 99:1–2); ethylene glycols; protein kinase inhibitors, such as, e.g. staurosporine, calphostin C, caffeic acid phenethyl ester, chelerythrine chloride, genistein; 1-(5-isoquinolinesulfonyl)-2-methylpiperazine; N-[2-((p-bromocinnamyl)amino)ethyl]-5-5-isoquinolinesulfonamide; KN-93; quercitin; d-erythro-sphingosine derivatives; UV irradiation; ionophores such as, e.g.: ionomycin and valinomycin; MAP kinase inducers such as, e.g.: anisomycin, anandamine; cell cycle blockers such as, e.g.: aphidicolin, colcemid, 5-fluorouracil, homoharringtonine; acetylcholinesterase inhibitors such as, e.g. berberine; anti-estrogens such as, e.g.: tamoxifen; pro-oxidants, such as, e.g.,: tert-butyl peroxide, hydrogen peroxide; free radicals such as, e.g., nitric oxide; inorganic metal ions, such as, e.g., cadmium; DNA synthesis inhibitors such as, e.g.: actinomycin D; DNA intercalators such as, e.g., doxorubicin, bleomycin sulfate, hydroxyurea, methotrexate, mitomycin C, camptothecin, daunorubicin; protein synthesis inhibitors such as, e.g., cycloheximide, puromycin, rapamycin; agents that affect microtubulin formation or stability such as, e.g.: vinblastine, vincristine, colchicine, 4-hydroxyphenylretinamide, paclitaxel; Bad protein, Bid protein and Bax protein (see, e.g., Jurgenmeier et al., 1998 *Proc. Nat. Acad. Sci. USA* 95:4997–5002 and references cited therein); calcium and inorganic phosphate (Kroemer et al., 1998 *Ann. Rev. Physiol.* 60:619).

Figure 2:
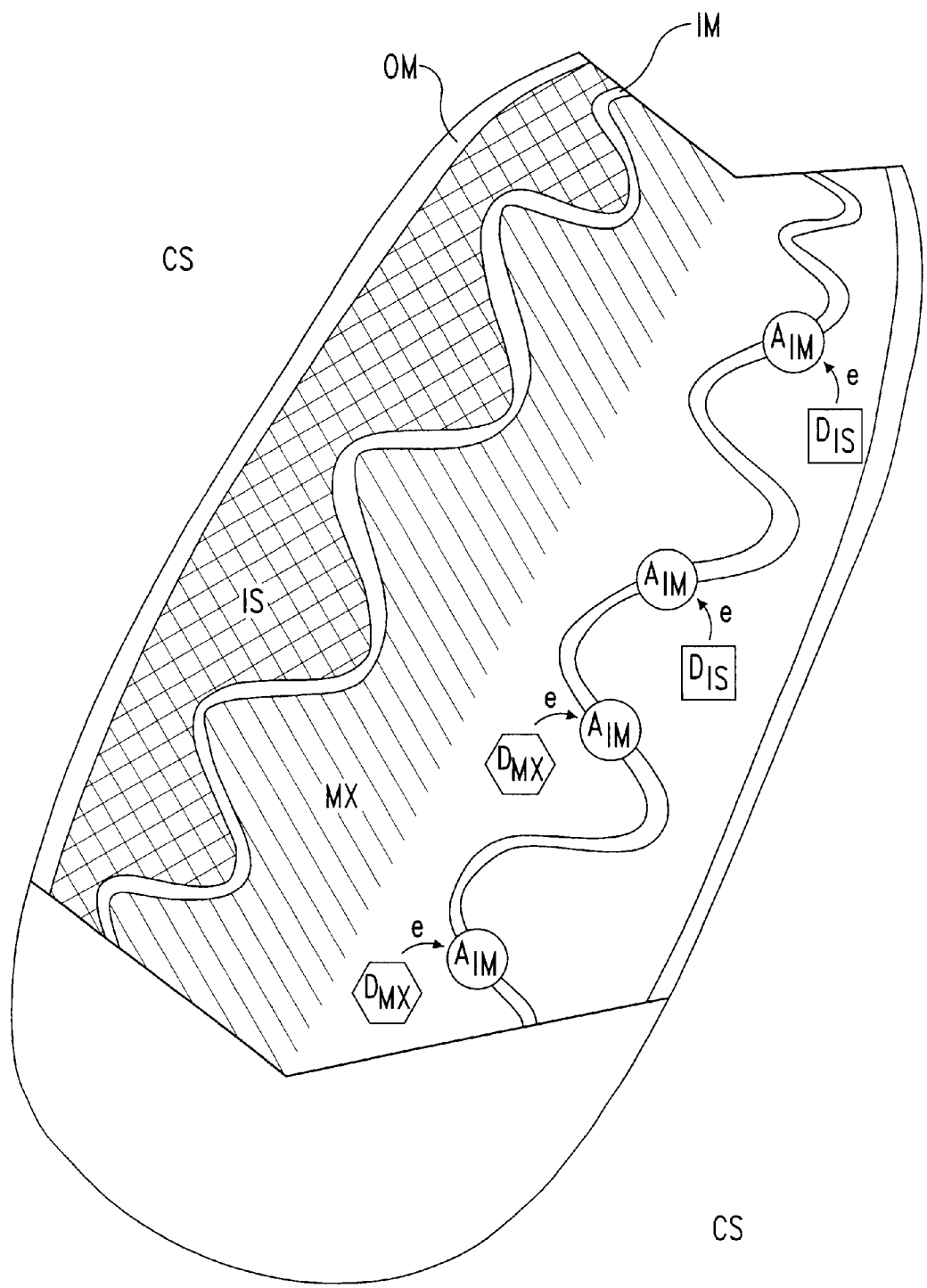
FIG. 2 schematically depicts submitochondrial structural compartments and energy transfer interactions between energy transfer donor and acceptor molecules in designated compartments: "CS," cytosolic space; "OM," outer membrane; "IS," intermembrane space; "IM," inner membrane; "MX," matrix; "$D_{MX}$," donor compound localizing to the matrix; "$A_{IM}$," acceptor compound localizing to the inner membrane; "$D_{IS}$," donor compound localizing to the intermembrane space; "e," energy.

Mitochondrial ultrastructural characterization reveals the presence of an outer mitochondrial membrane that serves as an interface between the organelle and the cytosol, a highly folded inner mitochondrial membrane that appears to form attachments to the outer membrane at multiple sites, and an intermembrane space between the two mitochondrial membranes (see FIG. 2). The subcompartment within the inner mitochondrial membrane is commonly referred to as the mitochondrial matrix. (For a review, see, e.g., Ernster et al., 1981 *J. Cell Biol.* 91:227s.) The cristae, originally postulated to occur as infoldings of the inner mitochondrial membrane, have recently been characterized using threedimensional electron tomography as also including tube-like conduits that may form networks, and that can be connected to the inner membrane by open, circular (30 nm diameter) junctions (Perkins et al., 1997, *Journal of Structural Biology* 119:260). While the outer membrane is freely permeable to ionic and non-ionic solutes having molecular weights less than about ten kilodaltons, the inner mitochondrial membrane exhibits selective and regulated permeability for many small molecules, including certain cations, and is impermeable to large (>~10 kDa) molecules.

Four of the five multisubunit protein complexes (Complexes I, III, IV and V) that mediate ETC activity are localized to the inner mitochondrial membrane. The remaining ETC complex (Complex II) is situated in the matrix. In at least three distinct chemical reactions known to take place within the ETC, protons are moved from the mitochondrial matrix, across the inner membrane, to the intermembrane space. This disequilibrium of charged species creates an electrochemical potential of approximately 220 mV referred to as the "protonmotive force" (PMF), which is often represented by the notation $\Delta\Psi$ or $\Delta\Psi m$. $\Delta\Psi m$ represents the sum of the electric potential and the pH potential (i.e., the pH differential) across the inner mitochondrial membrane (see, e.g., Ernster et al., 1981 *J. Cell Biol.* 91:227s and references cited therein).

$\Delta\Psi m$ provides the energy for phosphorylation of adenosine diphosphate (ADP) to yield ATP by ETC Complex V, a process that is coupled stoichiometrically with transport of a proton into the matrix. $\Delta\Psi m$ is also the driving force for the influx of cytosolic $Ca^{2+}$ into the mitochondrion. Under normal metabolic conditions, the inner membrane is impermeable to proton movement from the intermembrane space into the matrix, leaving ETC Complex V as the sole means whereby protons can return to the matrix. When, however, the integrity of the inner mitochondrial membrane is compromised, as occurs during mitochondrial permeability transition (MPT) that accompanies certain diseases associated with altered mitochondrial function, protons are able to bypass the conduit of Complex V without generating ATP, thereby uncoupling respiration from energy production. During MPT, $\Delta\Psi m$ collapses and mitochondrial membranes lose the ability to maintain an equilibrium distribution of one or more ionic species or other solutes, i.e., to selectively regulate permeability to solutes small (e.g., ionic $Ca^{2+}$, $Na^+$, $K^+$, $H^+$) and/or large (e.g., proteins).

Loss of mitochondrial membrane electrochemical potential may be the result of mechanisms such as free radical oxidation, or may be due to direct or indirect effects of mitochondrial and/or extramitochondrial gene products. Loss of mitochondrial potential appears to be a critical event in the progression of diseases associated with altered mitochondrial function, including degenerative diseases such as Alzheimer's Disease; diabetes mellitus; Parkinson's Disease; Huntington's disease; dystonia; Leber's hereditary optic neuropathy; schizophrenia; mitochondrial encephalopathy, lactic acidosis, and stroke (MELAS); cancer; psoriasis; hyperproliferative disorders; mitochondrial diabetes and deafness (MIDD) and myoclonic epilepsy ragged red fiber syndrome. To provide improved therapies for such diseases, agents that limit or prevent loss of mitochondrial membrane potential ($\Delta\Psi_m$) may be beneficial. The present invention provides a novel approach to the identification of agents useful for such diseases. The invention fulfills the need for an assay that permits rapid screening for agents capable of altering mitochondrial membrane potential and provides other related advantages.

Assays for Measuring Changes in Parameters in Subcellular Compartments

When the ET-based assay is designed to measure a change in state of, or decrease or increase in some activity at, a subcellular compartment or site, such as $\Delta\psi$ of mitochondria or the presence or absence of factors that are transiently associated with or released from an intracellular site, an additional criterion for donor-acceptor compounds is that one of the compounds (either the donor or the acceptor compound) must accumulate in and/or be released from the subcellular compartment or site in a manner that is dependent on the chosen parameter or activity, whereas the presence of the other compound (the acceptor or donor, respectively) in the subcellular compartment must be independent of the chosen parameter or activity.

Compounds whose mitochondrial concentration is dependent on $\Delta\psi$ include, by way of example and not limitation, TMRM (Farkas et al., *Biophys. J.* 56:1053–1069, 1989), TMRE (Ehrenberg et al., *Biophys. J.* 53:785–794, 1988), rhodamine 123 (Scaduto et al., *Biophys. J.* 76:469–477, 1999), ethidium bromide (Coppey-Moisan et al., *Biophys. J.* 71:2319–2328, 1996), DASPMI (4-Di-1-ASP and 2-Di-1-ASP) and DASPEI (Rafael et al., FEBS Letts. 170:181–185, 1984). Compounds whose mitochondrial concentration is not dependent on $\Delta\psi$ include, by way of example and not limitation, NAO (Maftah et al., *Biophys. Res. Commun.* 164:185–190, 1989), MitoTracker® Green FM and MitoFluor™ Green (Haugland, *Handbook of Fluorescent Probes and Research Chemicals,* 6th Ed., Molecular Probes, Inc., Eugene, Oreg., 1996, p. 269), and DAPI (Coppey-Moisan et al., *Biophys. J.* 71:2319–2328, 1996). Both collapse and dissipation of $\Delta\psi$ can be monitored using such compounds. As used herein, "$\Delta\psi$ collapse" refers to the rapid dissolution of $\Delta\psi$, ie., $\Delta\psi$ reaches zero within a few minutes after mitochondria are treated with an agent that induces collapse of mitochondrial membrane potential, such as, for instance CCCP or FCCP or any other agent capable of rapidly driving $\Delta\psi_m$ to zero. The term "$\Delta\psi$ dissipation" refers to a slower decrease in $\Delta\psi$ that does not result in $\Delta\psi$ reaching zero within a few minutes (although this may happen over a longer time frame or after repeated exposures) after mitochondria are treated with an agent that induces dissipation of mitochondrial membrane potential, such as, for example, ionomycin, thapsigargin, atractyloside, A23187, 4-bromo-A23187, adenine nucleotide translocator inhibitors, inhibitors of mitochondrial electron transport chain (ETC) complex I, inhibitors of ETC complex II in the presence of a complex I substrate, other partial inhibitors of the ETC or other agents that lead to an increased intramitochondrial calcium concentration as a result of elevated intracellular cytosolic free calcium concentration. Those having ordinary skill in the art are familiar with any number of mitochondrial ETC inhibitors that have been characterized with regard to which ETC components may be impaired. For additional disclosure relating to measurement of mitochondrial membrane potential, agents that induce collapse of mitochondrial membrane potential and agents that induce dissipation of mitochondrial membrane potential, see U.S. application Ser. Nos. 09/161,172 and 09/185,904.

Using mitochondria as an example, a variety of factors are known to be either (1) transiently associated with the outer membrane of the mitochondrion or (2) typically located at an intramitochondrial site but released from mitochondria during events such as, e.g., mitochondrial pore transition (MPT) or apoptosis (a.k.a. programmed cell death, PCD; for a review, see Green et al., *Science* 281:1309–1312, 1998). Examples of proteins belonging to class (1) include hexokinase II, and Bcl-2, Bcl-$X_L$, Bax and other members of the bcl-2 gene family (Kroemer, *Nature Med.* 3:614–620, 1997;

Nartita et al., *Proc. Natl. Acad. Sci. U.S.A.* 95:14681–14686, 1998). Examples of class (2) factors that are released during MPT or apoptosis include cytochrome c (Yang et al., *Science* 275:1129–1132, 1997; Kluck et al., *Science* 275:1132–1136, 1997), procaspase-2 and -9 (Susin et al., *J. Exp. Med.* 189:381–394, 1998) and apoptosis inducing factor (AIF; Susin et al., *J. Exp. Med.* 184:1331–1341, 1996, Susin et al., *J. Exp. Med.* 186:25–37, 1997). Nucleic acids comprising nucleotide sequences that encode these proteins can be used to construct fusion proteins with FLASH, aequorin or green fluorescent proteins such as wildtype GFP, BFP, CFP, RFP and YFP in order to construct fluorescent derivatives that exhibit the same transient associations with mitochondria, or releases from mitochondria, as the corresponding parent proteins. For example, hexokinase II fusion proteins that associate with the outer membrane of mitochondria (Sui et al., *Arch. Biochem. Biophys.* 345:111–125, 1997), and cytochrome c fusion proteins that localize GFP (Mahajan et al., *Nature Biotech.* 16:547–552, 1998) or other proteins (Nye et al., *Mol. Cell. Biol.* 10:5763–5771, 1990) to the intermembrane space of mitochondria, have been described. FLASH, aequorin and green fluorescent fusion proteins are used as donor or acceptor compounds in FRET-based assays designed to monitor the degree and/or rate of mitochondrial association or release of factors having various biological functions.

The ET-based methods of the invention possess certain advantages over other methods for assaying $\Delta\psi_m$. For example, methods that utilize a single potentiometric fluorophore (i.e., a fluorophore that accumulates in mitochondria in a $\Delta\psi_m$-dependent manner) may require that the fluorophores be present at concentrations that are toxic when agents that impact $\Delta\psi_m$ are introduced (see, e.g., U.S. Pat. No. 5,169,788). In contrast, the ET-based assays of $\Delta\psi_m$ of the invention can be carried out using lower, non-toxic doses of fluorophores. Furthermore, plasma membrane potential contributes to the signal in assays where a single potentiometric fluorophore is used, whereas the ET-based assays of the invention are specific for changes in mitochondrial membrane potential.

The detected fluorescence emission is typically compared to a reference signal. For quantitative measurements of $\Delta\Psi m$, the reference signal may be the signal observed in mitochondria with a known $\Delta\Psi m$, and one or more such references signals may be used. Alternatively, $\Delta\Psi m$ may be evaluated relative to a $\Delta\Psi m$ within the same type of mitochondria (e.g., mitochondria derived from the same subject or biological source), under certain specific conditions, to evaluate changes in $\Delta\Psi m$, or relative to a $\Delta\Psi m$ in a different type of mitochondria (e.g., mitochondria derived from a distinct subject or biological source). Specific embodiments of the present invention may employ different reference signals, as described in more detail below.

Chloroplasts

The chloroplast is an organelle found in plant cells wherein photosynthesis takes place. Photosynthesis, in addition to being an integral part of a plant cell's metabolism, is an important process that impacts many other living organisms as well. The reason for this is twofold: photosynthesis "fixes" atmospheric $CO_2$ into biologically usable carbohydrate $(CHO)_n$ molecules and also produces $O_2$ which is required by all aerobic organisms.

Like mitochondria, chloroplasts have a double (outer and inner) membrane, contain their own DNA and have translation factors (ribosomes, tRNAs, etc.) that are distinct from those found in the cytoplasm. Electron microscopy demonstrates that, like mitochondria, chloroplasts have a highly organized internal ultrastructure which includes flattened membranous bodies known as lamellae or thykaloid discs. Chloroplasts are, however, typically much larger than mitochondria; in higher plants they are generally cylindrical in shape and range from about 5 to $10\mu$ in length and from 0.5 to $2\mu$ in diameter. Like mitochondria, which are present in greater numbers in certain tissues (e.g., liver) than others, chloroplasts have greater copy numbers in some tissues than others. For example, mature leaves contain many chioroplasts and the total amount of chioroplast DNA in such leaves is about twice that of nuclear DNA (Jope et al., *J. Cell. Biol.* 79:631–636, 1978).

The Nucleus and the Nucleolus

The nucleus is the organelle that comprises most (from the standpoint of information, if not mass) of a cell's DNA in the form of several chromosomes (Mitochondria and chloroplasts have their own DNA molecules that are typically much smaller than the nuclear genomes, and thus encode fewer functions; however, as a cell contains only one nucleus and may contain many mitochondria and/or chloroplasts, the total mass of the DNA molecules in these organelles may approach that of the nuclear DNA.) The nucleus is bounded by two membranes collectively called the nuclear envelope (the membranes are known as the inner and outer nuclear membranes). Macromolecules, most particulary RNA molecules, are conveyed to or from the cytosol through openings in the nuclear envelope called nuclear pores.

The nucleolus is a subcompartment of the nucleus. In contrast to the remainder of the nucleus, wherein messenger (mRNA) molecules are transcribed from DNA, it appears that it is mainly ribosomal RNA (rRNA) molecules that are produced in the nucleolus.

Endosomes Lysosomes and Peroxisomes

Cells assimilate extracellular fluid, and macromolecules dissolved therein, by a process called endocytosis. Endocytotic vesicles are formed when a portion of the cell membrane evolves from a cup-shaped surface feature into an inwardly-directed "bud" and, eventually, a small membrane-bound vesicle that is taken up into the cytosol. At least two mechanisms have been proposed for the formation of the the cup-shaped surface features from which endosomes originate. First, local changes in the structure and/or composition of the lipid bilayer portion of the cell membrane can induce membrane curvature over a limited area thereof. Second, one or more coat proteins can act on a given location in the cell membrane to induce the formation of a cup-shaped surface feature. In the latter instance, the most well-characterized example are the "coated pits" that are formed, at least in part, by the protein clathrin (for a review, see Schekamn and Orci, *Science* 271:1526–1533, 1996).

Lysosomes contain various hydrolytic enzymes, each of which catalyzes the breakdown of specific types of macromolecules. Primary lysosomes containing such enzymes are produced intracellularly and may fuse with endosomes to form secondary lysosomes. In the latter type of vesicle, the enzymes from the primary lysosome are brought into contact with, and are thus free to act upon, the contents of the endosome. In general, after enzymatic digestion of the contents of the secondary lysosome, its membrane is dissolved in order to release its contents into the cytosol.

The formation and fate of, e.g., secondary lysosomes can be followed using the methods of the invention in the following manner. Cells are engineered to produce one or more lysosomal enzymes modified to contain a moiety capable of serving as an acceptor or donor in energy transfer.

Such cells are brought into contact with an agent that is taken up in endosomes, wherein the agent is or has been modified to be an ET acceptor or donor, respectively. When the resultant endosomes fuse with a primary lysosome, the acceptor and donor are present in the same subcellular compartment (the secondary lysosome), and ET occurs and can be monitored as described herein. The dissolution of the secondary lysosome liberates the ET acceptor-donor pair of molecules, which are then separated from each other as they are diluted into the cytosol, wherein the degree of ET decreases or ceases altogether.

Peroxisomes are another type of intracellular vesicles bounded by a single membrane. Unlike lysosomes, which generally contain hydrolytic enzymes, peroxisomes contain oxidative enzymes that generate and destroy hydrogen peroxide.

Endoplasmic Reticulum

The endoplasmic reticulum (ER) is composed of a series of flattended sheets, tubes and sacs that enclose a large intracellular space. The membrane of the ER is in structural continuity with the outer nuclear membrane and extends throughout the cytoplasm. Some functions of the ER include the synthesis and transport of membrane proteins and lipids. Generally speaking, two types of ERs may exist in a cell. Smooth ER is generally tubular in shape and is typically devoid of attached ribosomes; one major function of smooth ER is lipid metabolism. Rough ER typically occurs as flattened sheets, the cytosolic side of which is usually associated with many active (protein-synthesizing) ribosomes.

Golgi Apparatus

The Golgi apparatus is a system of stacked, flattened and membrane-enclosed sacs and is generally thought to be involved in the modification, sorting and packaging of macromolecules for secretion or for delivery to other subcellular compartments. Numerous small ($\geq$~50 nM) membrane-enclosed vesicles are thought to comprise macromolecules in order to carry out the transport thereof between the Golgi apparatus and other subcellular compartments.

Suborganellar Compartments

Certain components of organelles are also subcellular compartments within the scope of the invention. For example, mitochondria, chloroplasts and nuclei are surrounded by two membranes. The space between a set of paired membranes is not itself an organelle, but is a subcellular compartment as defined herein. Such spaces are named, e.g. and respectively, the mitochondrial intermembrane space, the chloroplast intermembrane space, the nuclear intermembrane space, etc. Conditions and processes within such spaces can be monitored according to the present invention by incorporating an acceptor-donor pair of molecules into the intermembrane, or by incorporating a donor or acceptor into the intermembrane space and an acceptor or donor, respectively, into either the inner or outer membrane.

The subcellular compartment may also be a membrane per se. In this aspect of the invention, membrane-directed donors [such as, e.g., 9-anthrylvinyl (LAPC)] and acceptors such as 3-perylenoyl (LPPC) are incorporated into one or more membranes of choice. The partition coefficients between membrane and aqueous phases are $8.3 \times 10^5$ and $10.5 \times 10^5$ or LAPC and LPPC, respectively (Razinkov et al., *Biochim. Biophys. Acta* 1329:149–158, 1997).

Intracellular Parasites

Other subcellular compartments of interest include intracellular parasites such as viruses and intracellular bacteria such as Rickettsiae and Chlamydia spp. Viruses consist of a genome, which may be composed of either DNA or RNA, that is surrounded by a protein shell. In the case of animal viruses, this protein shell is often itself enclosed within an envelope comprising both protein and lipid. Viruses multiply only within cells, as they are dependent on the host cells' macromolecular synthetic processes. They have thus been described as "genetic parasites."

One example of how the present invention may be applied to such intracellular parasites, provided by way of illustration and not limitation, is as follows. A viral particle typically consists of a "coat" or capsid surounding one or more nucleic acids. The capsid, which typically comprises one or more structural polypeptides, protects the viral nucleic acids in extracellular environments, but must (if the viral nucleic acids are to be liberated and replicated) be removed after the virus is internalized by a host cell. The process by which the capsid is removed is called "uncoating" and typically takes place in the cytoplasm (or a subcellular compartment, such as a vacuole, within the cytoplasm). Most animal viruses undergo uncoating as a result of the action of intracellular proteases on polypeptides that are a part of the capsid. Agents that inhibit or block viral uncoating, for example by inhibiting the action of intracellular proteases, are expected to be novel antiviral agents; a method of assaying viral uncoating would be useful for screening for such agents.

The present invention provides such a method for assaying viral uncoating in, for example, the following manner. Viral particles are prepared that contain an acceptor-donor pair of molecules ("loaded viruses"); this can be accomplished by, e.g., contacting viral particles or cells infected with viruses with a donor-acceptor pair of molecules that specifically localize to lipid membranes. By way of example and not limitation, the donor can be 9-anthrylvinyl (LAPC) and the acceptor can be 3-perylenoyl (LPPC) (Razinkov et al., *Biochim. Biophys. Acta* 1329:149–158, 1997).

Viral adsorption typically occurs equally well at 4° C. and 37° C., whereas uncoating, proceeds rapidly at 37° C., but slowly, if at all at 4° C. Accordingly, loaded viruses are contacted with cells at 4° C. for a period of time to allow for complete adsorption, after which the temperature is raised to 37° C. to allow uncoating to proceed. As uncoating of the loaded viruses proceeds, the donor-acceptor molecules are released from the capsid and they thus lose proximity to each other. This loss of proximity will be reflected in either an increase in fluorescence (if one molecule quenches the fluorescence of the other) or a decrease (if flurorescence is produced when the donor-acceptor molecules are in close proximity to each other). The rate of change in fluorescence thus correlates with viral uncoating. When added to this assay system, an agent that inhibits viral uncoating will reduce or eliminate the change in fluorescence.

Rickettsia are small, pleiomorphic, gram-negative coccobacilli that have adapted to intracellular growth in arthropods and other organisms. Except for *R. quintana* (the agent of trench fever), all rickettsiae require living cells for growth. Species differ in terms of the location of intracellular multiplication; for example, *R. tsutsugamushi* typically grow only in the cytoplasm, organisms of the spotted fever group grow both in the cytoplasm and the nucleus, and *C. burnetii* grows within the cytoplasm and phagolysosomes.

Chlamydiaceae is a family of obligate intracellular bacterial parasites that infect a number of vertebrate hosts, typically birds or mammals (including humans). The distinct developmental cycle of Chlamydia begins with the attachment to, and internalization by, a host cell by an elementary body (the metabolically dormant, extracellular phase of Chlyamydia). Phagocytized elementary bodies develop into reticulate bodies that multiply by binary fission. Elementary body progeny are formed from the replicated reticulate bodies and released when the host cells rupture.

The life-cycle of Chlamydia presents another non-limiting example of how the invention may be applied to intracellular parasites. Chlamydia survive intracellularly within phagosomes, in part because the elementary body cell wall appears to inhibit fusion of the phagosomes with lysosomes that contain hydrolytic enzymes that would degrade the elementary bodies if phagolysosomes were formed. When elementary bodies are labeled with a donor or acceptor molecule, and lysosomes with an acceptor or donor molecule, respectively, energy transfer will occur if phagolysosomes are formed. Agents that inhibit the elementary body'ability to prevent fusion of phagosomes and lysosomes will result in energy transfer that can be monitored by the present invention; such agents are expected to be novel antibiotics useful for treating Chlamydia infections.
Assaying Interactions Between Macromolecules within or Associated with Subcellular Compartments In another aspect of the invention, energy transfer is used to monitor interactions between pairs of macromolecules found within or associated with subcellular compartments. This embodiment, which is drawn to means for monitoring the association of a macromolecular species and an organelle or other subcellular compartment, should not be confused with systems in which energy transfer in used to evaluate the interaction between two types of macromolecules.

As one example, some cancer cells are thought to result, at least in part form overexpression of a protein that may preferentially associate with one or more subcellular compartments. The bcl-2 gene was initially identified as a causal factor in certain types of lymphatic cancers (B-cell lymphoma, hence the name) in which bcl-2 is overexpressed, resulting in an abnormally longer lifespan for B-cells, which in turn is thought to allow these cells to accumulate additional mutations resulting in frank malignancy and lymphatic tumor development (for reviews of the Bcl-2 family of proteins, see Davies, *Trends in Neuroscience* 18:355–358, 1995; Kroemer, *Nature Med.* 3:614–620, 1997; Wo95/13292; W095/00160; and U.S. Pat. No. 5,015,568).

Although the biochemical function of Bcl-2 is not known (i.e., it is not clear whether it acts as an enzyme, receptor or signaling molecule), it is known to be localized to the outer mitochnodrial membrane, the nuclear membrane and the endoplasmic reticulum. Another member of the Bcl-2 family of proteins, Bax, localizes to the outer mitochondrial membrane. Although FRET has been used to demonstrate the interaction of Bcl-2 and Bax in individual mitochondria (Mahajan et al., *Nat. Biotechnol.* 16:547–552, 1998), energy transfer has not been used to monitor the association (or dissociation) of such proteins with (or from) subcellular compartments. The present invention provides methods for monitoring the interactions of macromolecules with subcellular compartments.

One example of such a method is as follows. The width of the combined inner and outer mitochondria membranes has been estimated to be 22±4 nm (Perkins et al., *J. Structural Biol.* 119:260–272, 1997). Accordingly, loading the intermembrane space with donor (or acceptor) molecules would be expected to bring them in sufficiently close proximity with acceptor (or donor) molecules present within or associated with the outer mitochondrial membrane. Events such as the localization of Bcl-2 proteins to the outer mitochondrial membrane could thus be monitored by tagging Bcl-2 with an acceptor (or donor) that undergoes energy transfer with a donor (or acceptor) that has been loaded into the intermembrane space. In like fashion, the dissociation of proteins such as cytochrome c from mitochondria can be followed using donor- or acceptor-tagged cytochrome c proteins and acceptor- or donor-loaded (respectively) intramembrane spaces. Such processes are thought to represent significant events in apoptotic pathways (Green et al., *Science* 281:1309–1312, 1998; *Green*, Cell 94:695–698, 1998).
Screening for Species-Specific Agents In certain embodiments, the present invention provides screening assays for identifying species-specific agents. A "species-specific agent" refers to an agent that affects a subcellular compartment of a first organism belonging to one species but that does not affect the homologous subcellular compartment of a second organism belonging to another species. Thus the invention provides a method for identifying an agent that preferentially alters a cellular membrane potential in a subcellular compartment of a first biological source without substantially altering a corresponding cellular membrane potential in a subcellular compartment of a second biological source. In preferred embodiments, the subcellular compartment is a mitochondrion and the cellular membrane potential is mitochondrial membrane potential. The screening assays provided by the instant methods are thus directed in pertinent part to assaying, in the absence and presence of a candidate agent, a cellular membrane potential by contacting each of a first and second sample comprising one or more cellular membranes from a first and a second distinct biologcal source, respectively, with an ET donor and an ET acceptor molecule, exciting the ET donor to produce an excited ET donor molecule, detecting a signal generated by energy transfer from the ET donor to the ET acceptor and comparing the signal generated in the absence of the candidate agent to the signal generated in the presence of the candidate agent.

In those certain preferred embodiments wherein the invention is directed to a method for identifying an agent that preferentially alters mitochondrial membrane potential in mitochondria from a first biological source without substantially altering mitochondrial membrane potential in mitochondria from a second biological source, neither the ET donor molecule nor the ET acceptor molecule is endogenous to mitochondria, and the ET donor and the ET acceptor each localize independently of one another to the same submitochondrial site or to acceptably adjacent submitochondrial sites as provided herein. Typically, based upon the teachings provided herein, a person having ordinary skill in the art can readily determine when a candidate agent alters a cellular membrane potential such as mitochondrial membrane potential, for example, by detecting a statistically significant change in the membrane potential in the presence of the agent relative to the potential detected in the absence of the agent. Methods for determining mitochondrial membrane potential are also provided in U.S. application Ser. No. 09/161,172.

As used herein, an agent identified according to the instant method that is a species-specific agent or an agent that "preferentially" alters mitochondrial membrane potential in the mitochondria from a first biological source (e.g., a first species) without substantially altering the mitochondrial membrane potential in the mitochondria from a second biological source (e.g., a second species) refers to an agent that, following contact with mitochondria or cells of the first and second species, effects the continued viability of the mitochondria or cells from one of the species (i.e., either the first or the second species but not both) while effecting the death or growth impairment of the mitochondria or cells from the other species. Similarly, where such an agent does not "substantially" alter mitochondrial membrane potential in the mitochondria of the first species refers to an agent that, following contact with mitochondria or cells of the first and second species, effects the continued viability of the mitochondria or cells from one of the species (i.e., either the first or the second species but not both) while effecting the death or growth impairment of the mitochondria or cells from the other species. Thus, preferential alteration of mitochondrial membrane potential by such an agent may increase or may decrease $\Delta\Psi_m$, as long as the effect is species-specific. Without wishing to be bound by theory, cells that undergo death or growth impairment in a species-specific manner as a result of contact with such an agent identified according to the instant method may do so by becoming apoptotic or necrotic, by entering cell cycle arrest or by becoming cytostatic, or by failing to remain viable or capable of growth by any other mechanism.

In certain other embodiments an agent identified according to the instant method that that "preferentially" alters mitochondrial membrane potential in the mitochondria from a first biological sample (e.g., a first tissue) without substantially altering the mitochondrial membrane potential in the mitochondria from a second biological sample (e.g., a second tissue) refers to an agent that, following contact with mitochondria or cells of the first and second biological samples, effects the continued viability of the mitochondria or cells from one of the samples (i.e., either the first or the second tissue samples but not both) while effecting the death or growth impairment of the mitochondria or cells from the other sample. Similarly, where such an agent does not "substantially" alter mitochondrial membrane potential in the mitochondria of the first sample refers to an agent that, following contact with mitochondria or cells of the first and second species, effects the continued viability of the mitochondria or cells from one of the samples (i.e., either the first or the second samples but not both) while effecting the death or growth impairment of the mitochondria or cells from the other species. Thus, preferential alteration of mitochondrial membrane potential by such an agent may increase or may decrease $\Delta\Psi_m$, as long as the effect is sample-specific. According to these embodiments, an agent may be identified that acts selectively in a tissue-specific manner, such that the agent may be employed to manipulate mitochondrial membrane potential in certain tissue types but not other, even within the same organism. Alternatively, the first and second tissues may be derived from distinct subjects of the same species, or from subjects of distinct species. For example, according to such a method of the instant invention, an agent may be identified using this approach that preferentially alters neuronal cell mitochondrial membrane potential without substantially altering liver cell mitochondrial membrane potential.

Using mitochondria as an example of a subcellular compartment, this embodiment of the invention may be used, for example, to identify agents that selectively induce collapse of $\Delta\psi$ in mitochondria derived from different species, e.g., in trypanosomes (Ashkenazi et al., *Science* 281:1305–1308, 1998), and other eukaryotic pathogens and parasites, including but not limited to insects, but which do not induce $\Delta\psi$ collapse in the mitochondria found in the cells of their mammalian hosts. Such agents are expected to be useful for the prophylactic or therapeutic management of such pathogens and parasites.

For example, members of the phylum Apicomplexa (formerly called Sporozoa) comprise a large and diverse group of pathogenic protozoa that are intracellular parasites. Some members, including species of Babesia, Theileria and Eimeria, cause economically important animal diseases, and other members, such as *Toxoplasma gondii* and Cryptosporidium spp. also cause human disease, particularly in immunocompromised individuals. The acomplexicans are unusual in terms of their extrachromosomal DNA elements, as they comprise both a mitochondrial genome and a putative plastid genome (see Feagin, *Annu. Rev. Microbiol.* 48:81–104, 1994, for a review). Probably the most well-studied acomplexicans are species of Plasmodium, which cause malaria. Antimalarial agents include agents that specifically impact the function of Plasmodium mitochondria (Peters et al., *Ann. Trop. Med. Parsitol.* 78:567–579, 1984; Basco et al., *J. Eukaryot. Microbiol.* 41:179–183, 1994), and one such agent, atovaquone, collapses $\Delta\psi$ in mitochondria from *Plasmodium yoelii* but has no effect on $\Delta\psi$ of mamallian mitochondria (Srivastava et al., *J. Biol. Chem.* 272:3961–3966, 1997). Accordingly, the ET-based assay of $\Delta\psi$ of the present invention can be used to screen libraries of compounds for novel antimalarial agents, i.e., compounds that cause $\Delta\psi$ collapse in Plasmodium mitochondria but not in mamalian mitochondria.

As another example, this embodiment of the invention is used to create and identify agents that selectively induce $\Delta\psi$ collapse in mitochondria derived from undesirable plants (e.g., weeds) but not in desirable plants (e.g., crops), or in undesirable insects (in particular, members of the family Lepidoptera and other crop-damaging insects) but not in desirable insects (e.g., bees) or desirable plants. Such agents are expected to be useful for the management and control of such undesirable plants and insects. Cultured insect cells, including for example, the Sf9 and Sf21 cell lines derived from *Spodoptera frugiperda*, and the HIGH FIVE™ cell line from *Trichopolusia ni* (these three cell lines are available from InVitrogen, Carlsbad, Calif.) may be the source of mitochondria in certain such embodiments of the invention.

In this embodiment of the invention, the subcellular compartment of interest of a first species is loaded with a first donor-acceptor pair of molecules which fluoresce at a first wavelength, and the corresponding subcellular compartment from a second species is loaded with a second donor-acceptor pair of molecules which fluoresce at a second wavelength. For example, mitochondria from two different species may be loaded with such donor-acceptor pairs of molecules. The two types of loaded mitochondria are placed in a single chamber, and an agent to be tested for its ability to induce MPT in a species-specific manner is then also introduced into the chamber. The change in fluorescence at both the first and second wavelength is measured over time in a concomitant fashion. For example, a Fluorometric Imaging Plate Reader (FLIPR™) instrument (see infra) may be used to rapidly alternate between a first mode, in which fluorescence at the first wavelength is monitored, to a second mode in which fluorescence at the second wavelength is monitored. A species-specific agent will induce MPT in the mitochondria from the first species, but not in those in the mitochondria from the second species, and will thus effect the degree, rate, frequency or extent in changes of fluorescence at one wavelength but not the other.

Diagnostics and Screening for Therapeutic Agents

The invention may be used to develop assays of subcellular conditions or intracellular processes that are associated with diseases or disorders for a variety of purposes. One purpose is to aid in the diagnosis and prognosis of patients suffering from such diseases and disorders, and to help determine if an individual is potentially predisposed to developing such diseases and disorders. Another purpose is to screen collections of compounds for agents having remedial, therapeutic, palliative, rehabilitative, preventative, prophylactic or disease-impeditive effects on patients suffering from, or potentially predisposed to developing, such diseases and disorders.

The present invention therefore provides methods for identifying an agent that alters cellular membrane potential, and that in certain preferred embodiments alters mitochondrial membrane potential. In certain other preferred embodiments the invention provides a method for identifying a regulator of an agent that alters mitochondrial membrane potential. The screening assays provided by the instant methods are thus directed in pertinent part to assaying, in the absence and presence of a candidate agent or a candidate regulator, a cellular membrane potential by contacting a sample comprising one or more cellular membranes with an ET donor and an ET acceptor molecule, exciting the ET donor to produce an excited ET donor molecule, detecting a signal generated by energy transfer from the ET donor to the ET acceptor and comparing the signal generated in the absence of the candidate agent (or regulator) to the signal generated in the presence of the candidate agent (or regulator). Embodiments that are directed to a method for identifying a regulator of an agent that alters mitochondrial membrane potential further comprise contacting a sample, prior to the step of detecting, with an agent that is either a known agent that alters mitochondrial membrane potential or an agent that alters mitochondrial membrane potential and that is identified according to the methods provided herein.

In those certain preferred embodiments wherein the invention is directed to a method for identifying an agent that alters mitochondrial membrane potential, or to a method for identifying a regulator of an agent that alters mitochondrial membrane potential, neither the ET donor molecule nor the ET acceptor molecule is endogenous to mitochondria, and the ET donor and the ET acceptor each localize independently of one another to the same submitochondrial site or to acceptably adjacent submitochondrial sites as provided herein. Typically, based upon the teachings provided herein, a person having ordinary skill in the art can readily determine when a candidate agent alters a cellular membrane potential such as mitochondrial membrane potential, for example, by detecting a statistically significant change in the membrane potential in the presence of the agent relative to the potential detected in the absence of the agent. Methods for determining mitochondrial membrane potential are also provided in U.S. application Ser. No. 09/161,172.

Similarly, for purposes of determining whether a compound that is a candidate regulator of an agent that alters a cellular membrane potential such as mitochondrial membrane potential, methods for quantifying membrane potential will be useful. Agents that alter mitochondrial membrane potential include agents known to have such properties, including agents that dissipate mitochondrial membrane potential and agents that collapse mitochondrial membrane potential (e.g., those described in greater detail in the Examples below), as well as agents identified according to methods provided herein. A regulator of an agent that alters mitochondrial membrane potential includes any agent that in a specific manner directly or indirectly influences (e.g., increases or decreases) the ability of an agent that alters mitochondrial membrane potential to alter mitochondrial membrane potential. Thus, for example, a regulator of an agent that alters mitochondrial membrane potential may be an agonist or may be an antagonist of the agent that alters mitochondrial membrane potential. For example, where an agent that alters mitochondrial membrane potential dissipates the potential, a regulator that is an agonist may potentiate such dissipation (e.g., cause collapse) while a regulator that is an antagonist of the agent that alters mitochondrial membrane potential may confer a protective effect on mitochondrial membrane potential when the dissipating agent is present. Conversely, for an agent that alters mitochondrial membrane potential by preserving or enhancing $\Delta\Psi_m$, regulators that are agonists may also protect or enhance potential while regulators that are antagonists may lead to dissipation or collaspse of $\Delta\Psi_m$. Without wishing to be bound by theory, a regulator as described herein may participate in intermolecular interaction events (e.g., recognition, binding, complex formation, covalent modification, alteration of conformation) with one or more of an agent that alters mitochondrial membrane potential and the subcellular target or targets of the agent that alters mitochondrial membrane potential, including mitochondrial molecular components. (Mitochondrial molecular components are described, for example, in U.S. application Ser. No.b 09/161,172.)

Thus, where a number of disorders and diseases result from processes involving mitochondria, the main energy source in cells of higher organisms, the invention provides compositions and methods for monitoring mitochondrial membrane potential ($\Delta\psi$) and changes therein via energy transfer, as noted above. As described in detail herein, $\Delta\psi$ is required for a variety of mitochondrial functions, and defects in the production or maintenance of $\Delta\psi$ are associated with many diseases and disorders. Furthermore, changes in $\Delta\psi$ occur in a variety of subcellular processes that can serve as targets for the development of therapeutic agents. Thus, the ET-based assay of $\Delta\psi$ can be used to help confirm the presence of a disease or disorder associated with alterations in $\Delta\psi$ in an individual, or an individual's predisposition to such a disease or disorder, and to screen for agents that stabilize, increase or decrease (as appropriate) $\Delta\psi$ and can thus be used to treat such diseases and disorders. Moreover, the ET-based assay of $\Delta\psi$ can be used to screen for agents that selectively perturb $\Delta\psi$ in undesirable cells such as, e.g., cancer cells, thus leading to the specific destruction or inhibition of growth of such undesirable cells.

Mitochondria provide direct and indirect biochemical regulation of a wide array of cellular respiratory, oxidative and metabolic processes (for a review, see Ernster and Schatz, *J. Cell Biol.* 91:227s–255s, 1981), including electron transport chain (ETC) activity, which drives oxidative phosphorylation to produce metabolic energy in the form of adenosine triphosphate (ATP), and which also underlies a central mitochondrial role in intracellular calcium homeostasis. In addition to their role in metabolic processes, mitochondria are also involved in the genetically programmed cell suicide sequence known as "apoptosis" (Green and Reed, *Science* 281:1309–1312, 1998; Susin et al., *Biochim. et Biophys. Acta* 1366:151–165, 1998).

Defective mitochondrial activity, including but not limited to failure at any step of the elaborate multi-complex mitochondrial assembly, known as the electron transport chain (ETC), may result in (i) decreases in ATP production, (ii) increases in the generation of highly reactive free radicals (e.g., superoxide, peroxynitrite and hydroxyl radicals, and hydrogen peroxide), (iii) disturbances in intracellular calcium homeostasis and (iv) the release of factors (such as such as cytochrome c and "apoptosis inducing factor") that initiate or stimulate the apoptosis cascade. Because of these biochemical changes, mitochondrial dysfunction has the potential to cause widespread damage to cells and tissues.

A number of diseases and disorders are thought to be caused by or be associated with alterations in mitochondrial metabolism and/or inappropriate induction or suppression of mitochondria-related functions leading to apoptosis. These include, by way of example and not limitation, chronic neurodegenerative disorders such as Alzheimer's disease (AD) and Parkinson's disease (PD); auto-immune diseases; diabetes mellitus, including Type I and Type II; mitochondria associated diseases, including but not limited to congenital muscular dystrophy with mitochondrial structural abnormalities, fatal infantile myopathy with severe mtDNA depletion and benign "later-onset" myopathy with moderate reduction in mtDNA, MELAS (mitochondrial encephalopathy, lactic acidosis, and stroke) and MIDD (mitochondrial diabetes and deafness); MERFF (myoclonic epilepsy ragged red fiber syndrome); arthritis; NARP (Neuropathy; Ataxia; Retinitis Pigmentosa); MNGIE (Myopathy and external ophthalmoplegia; Neuropathy; Gastro-Intestinal; Encephalopathy), LHON (Leber's Hereditary Optic Neuropathy), Kearns-Sayre disease; Pearson's Syndrome; PEO (Progressive External Ophthalmoplegia); Wolfram syndrome; DIDMOAD (Diabetes Insipidus, Diabetes Mellitus, Optic Atrophy, Deafness); Leigh's Syndrome; dystonia; schizophrenia; and hyperproliferative disorders, such as cancer, tumors and psoriasis.

According to generally accepted theories of mitochondrial function, proper ETC respiratory activity requires maintenance of an electrochemical potential ($\Delta\Psi$) in the inner mitochondrial membrane by a coupled chemiosmotic mechanism. Conditions that dissipate or collapse this membrane potential, including but not limited to failure at any step of the ETC, may thus prevent ATP biosynthesis and hinder or halt the production of a vital biochemical energy source. Altered or defective mitochondrial activity may also result in a catastrophic mitochondrial collapse that has been termed "mitochondrial permeability transition" (MPT). In addition, mitochondrial proteins such as cytochrome c and "apoptosis inducing factor" may dissociate or be released from mitochondria due to MPT (or the action of mitochondrial proteins such as Bax), and may induce proteases known as caspases and/or stimulate other events in apoptosis (Murphy, *Drug Dev. Res.* 46:18–25, 1999).

Defective mitochondrial activity may alternatively or additionally result in the generation of highly reactive free radicals that have the potential of damaging cells and tissues. These free radicals may include reactive oxygen species (ROS) such as superoxide, peroxynitrite and hydroxyl radicals, and potentially other reactive species that may be toxic to cells. For example, oxygen free radical induced lipid peroxidation is a well established pathogenetic mechanism in central nervous system (CNS) injury such as that found in a number of degenerative diseases, and in ischemia (i.e., stroke). Mitochondrial involvement in the apoptotic cascade has been identified, for example mitochondrial release of cytochrome c, and may therefore be a factor in neuronal death that contributes to the pathogenesis of certain neurodegenerative (i.e., CNS) diseases.

There are, moreover, at least two deleterious consequences of exposure to reactive free radicals arising from mitochondrial dysfunction that adversely impact the mitochondria themselves. First, free radical mediated damage may inactivate one or more of the myriad proteins of the ETC. Second, free radical mediated damage may result in catastrophic mitochondrial collapse that has been termed "transition permeability". According to generally accepted theories of mitochondrial function, proper ETC respiratory activity requires maintenance of an electrochemical potential in the inner mitochondrial membrane by a coupled chemiosmotic mechanism. Free radical oxidative activity may dissipate this membrane potential, thereby preventing ATP biosynthesis and/or triggering mitochondrial events in the apoptotic cascade. Therefore, by modulating these and other effects of free radical oxidation on mitochondrial structure and function, the present invention provides compositions and methods for protecting mitochondria that are not provided by the mere determination of free radical induced lipid peroxidation.

For example, rapid mitochondrial permeability transition likely entails changes in the inner mitochondrial transmembrane protein adenylate translocase that results in the formation of a "pore". Whether this pore is a distinct conduit or simply a widespread leakiness in the membrane is unresolved. In any event, because permeability transition is potentiated by free radical exposure, it may be more likely to occur in the mitochondria of cells from patients having mitochondria associated diseases that are chronically exposed to such reactive free radicals.

Altered mitochondrial function characteristic of the mitochondria associated diseases may also be related to loss of mitochondrial membrane electrochemical potential by mechanisms other than free radical oxidation, and such transition permeability may result from direct or indirect effects of mitochondrial genes, gene products or related downstream mediator molecules and/or extramitochondrial genes, gene products or related downstream mediators, or from other known or unknown causes. Loss of mitochondrial potential therefore may be a critical event in the progression of mitochondria associated or degenerative diseases.

Diabetes

Diabetes mellitus is a common, degenerative disease affecting 5 to 10 percent of the population in developed countries. The propensity for developing diabetes mellitus is reportedly maternally inherited, suggesting a mitochondrial genetic involvement (Alcolado et al., *Br. Med. J.* 302:1178–1180, 1991; Reny, *Int. J. Epidem.* 23:886–890, 1994). Diabetes is a heterogenous disorder with a strong genetic component; monozygotic twins are highly concordant and there is a high incidence of the disease among first degree relatives of affected individuals.

At the cellular level, the degenerative phenotype that may be characteristic of late onset diabetes mellitus includes indicators of altered mitochondrial respiratory function, for example impaired insulin secretion, decreased ATP synthesis and increased levels of reactive oxygen species. Studies have shown that diabetes mellitus may be preceded by or associated with certain related disorders. For example, it is estimated that forty million individuals in the U.S. suffer from late onset impaired glucose tolerance (IGT). IGT patients fail to respond to glucose with increased insulin secretion. A small percentage of IGT individuals (5–10%) progress to insulin deficient non-insulin dependent diabetes (NIDDM) each year. Some of these individuals further progress to insulin dependent diabetes mellitus (IDDM). These forms of diabetes mellitus, NIDDM and IDDM, are associated with decreased release of insulin by pancreatic beta cells and/or a decreased end-organ response to insulin. Other symptoms of diabetes mellitus and conditions that precede or are associated with diabetes mellitus include obesity, vascular pathologies, peripheral and sensory neuropathies, blindness and deafness.

Due to the strong genetic component of diabetes mellitus, the nuclear genome has been the main focus of the search for causative genetic mutations. However, despite intense effort, nuclear genes that segregate with diabetes mellitus are known only for rare mutations in the insulin gene, the insulin receptor gene, the adenosine deaminase gene and the glucokinase gene. Accordingly, mitochondrial defects, which may include but need not be limited to defects related to the discrete non-nuclear mitochondrial genome that resides in mitochondrial DNA, may contribute significantly to the pathogenesis of diabetes mellitus (Anderson, *Drug Dev. Res.* 46:67–79, 1999).

A number of mitochondrial mutations associated with diabetic phenotypes have been described (for reviews, see Gerbitz et al., *Biochim. Biophys. Acta* 1271:253–260, 1995, or Rötig et al., *Diabetes Metab.* 22:291–298, 1996). A number of such mutations occur in genes encoding factors involved in protein translation within mitochondria, such as mitochondrial tRNAs (see, e.g., Suzuki et al., *Diabetes Care* 17:1428–1432, 1994; Kishimoto et al., *Diabetologia* 38:193–200, 1995; van der Ouweland et al., *Muscle Nerve Suppl.* 3:S124–S130, 1995; Hanna et al., *Am. J. Hum. Genet.* 56:1026–1033, 1995; Sano et al., *J. Neurol.* 243:441–444, 1996; Kameoka et al., *Biochem. Biophys. Res. Commun.* 245:523–527, 1998; and Hirai et al., *J. Clin. Endocrinol. Metab.* 83:992–994, 1998). Because mitochondrial translation is dependent on $\Delta\psi$ (Côté et al., *J. Biol. Chem.* 264:8487–8490, 1989; Côté et al., *J. Biol. Chem.* 265:7532–7538, 1990), alterations in $\Delta\psi$ may result in diabetic phenotypes in some instances, and individuals suspected of having or being predisposed to developing diabetes may be identified using the ET-based assay $\Delta\psi$ of the invention. Furthermore, agents that increase and/or stabilize $\Delta\psi$ are expected to have remedial, therapeutic, palliative, rehabilitative, preventative, prophylactic or disease-impeditive effects on patients suffering from, or thought to be predisposed to developing, diabetes. The ET-based assay of $\Delta\psi_m$ of the invention can also be used to estimate which agent(s) are most likely to be effective for a given individual, in that a patient having mitochondria that exhibit an altered $\Delta\psi_m$ is expected to be more likely to respond to agents that modulate $\Delta\psi_m$ than a patient having mitochondria with a normal $\Delta\psi$.

Parkinson's Disease

Parkinson's disease (PD) is a progressive, chronic, mitochondria associated neurodegenerative disorder characterized by the loss and/or atrophy of dopamine-containing neurons in the pars compacta of the substantia nigra of the brain. Like Alzheimer's Disease (AD), PD also afflicts the elderly. It is characterized by bradykinesia (slow movement), rigidity and a resting tremor. Although L-Dopa treatment reduces tremors in most patients for a while, ultimately the tremors become more and more uncontrollable, making it difficult or impossible for patients to even feed themselves or meet their own basic hygiene needs.

It has been shown that the neurotoxin 1-methyl-4-phenyl-1,2,3,6-tetrahydropyridine (MPTP) induces parkinsonism in animals and man at least in part through its effects on mitochondria. MPTP is converted to its active metabolite, MPP+, in dopamine neurons; it then becomes concentrated in the mitochondria. The MPP+ then selectively inhibits the mitochondrial enzyme NADH:ubiquinone oxidoreductase ("Complex I"), leading to the increased production of free radicals, reduced production of adenosine triphosphate, and ultimately, the death of affected dopamine neurons.

Apoptotic cell death is thought to constitute the terminal process in some neurodegenerative diseases, notably Alzheimer's and Parkinson's disease. It has been proposed that agents that help to maintain $\Delta\psi$ might offer novel agents for preventing or treating neurodegenerative apoptosis (Tatton et al., *Ann. Neurol.* 44:S134–S141, 1998). Individuals suspected of having or being predisposed to developing Parkinson's disease (PD) may be identified using the ET-based assay $\Delta\psi$ of the invention. Moreover, the ET-based $\Delta\psi$ assay of the invention can be used to identify and characterize compounds that enhance or stabilize $\Delta\psi$, and these compounds are expected to have remedial, therapeutic, palliative, rehabilitative, preventative, prophylactic or disease-impeditive effects on patients suffering from, or thought to be predisposed to developing, PD. The ET-based assay of $\Delta\psi$ of the invention can also be used to estimate which agent(s) are most likely to be effective for a given individual, in that a PD patient having mitochondria that exhibit an altered $\Delta\psi$ is expected to be more likely to respond to agents that modulate $\Delta\psi$ than a PD patient having mitochondria with a normal $\Delta\psi$.

Alzheimer's Disease

Alzheimer's disease (AD) is a chronic, progressive neurodegenerative disorder that is characterized by loss and/or atrophy of neurons in discrete regions of the brain, and that is accompanied by extracellular deposits of β-amyloid and the intracellular accumulation of neurofibrillary tangles. It is a uniquely human disease, affecting over 13 million people worldwide. It is also a uniquely tragic disease. Many individuals who have lived normal, productive lives are slowly stricken with AD as they grow older, and the disease gradually robs them of their memory and other mental faculties. Eventually, they cease to recognize family and loved ones, and they often require continuous care until their eventual death.

Mitochondrial dysfunction is thought to be critical in the cascade of events leading to apoptosis in various cell types (Kroemer et al., *FASEB J.* 9:1277–1287, 1995), and may be a cause of apoptotic cell death in neurons of the AD brain. Altered mitochondrial physiology may be among the earliest events in PCD (Zamzami et al., *J. Exp. Med.* 182:367–77, 1995; Zamzami et al., *J. Exp. Med.* 181:1661–72, 1995) and elevated reactive oxygen species (ROS) levels that result from such altered mitochondrial function may initiate the apoptotic cascade (Ausserer et al., *Mol. Cell. Biol.* 14:5032–42, 1994). Indeed, one hallmark pathology of AD is the death of selected neuronal populations in discrete regions of the brain. Cell death in AD is presumed to be apoptotic because signs of programmed cell death (PCD) are seen and indicators of active gliosis and necrosis are not found (Smale et al., *Exp. Neurolog.* 133:225–230, 1995; Cotman et al., *Molec. Neurobiol.* 10:19–45, 1995.) The consequences of cell death in AD, neuronal and synaptic loss, are closely associated with the clinical diagnosis of AD and are highly correlated with the degree of dementia in AD (DeKosky et al., *Ann. Neurology* 2757–464, 1990).

In several cell types, including neurons, reduction in the mitochondrial membrane potential ($\Delta\Psi$) precedes the nuclear DNA degradation that accompanies apoptosis. In cell-free systems, mitochondrial, but not nuclear, enriched fractions are capable of inducing nuclear apoptosis (Newmeyer et al., *Cell* 70:353–64, 1994). Moreover, cybrids comprising mitochondria derived from AD patients have lower resting mitochondrial membrane potentials than the corresponding parental SH-SY5Y cell line, and cyclosporin A reverses the depressed $\Delta\psi$ in the AD cybrids (Cassarino et al., *Biochem. Biophys. Res. Commun.* 248:168–173, 1998). Individuals suspected of having or being predisposed to developing AD may be identified using the ET-based assay $\Delta\psi$ of the invention. Moreover, the ET-based $\Delta\psi$ assay of the invention can be used to identify and characterize compounds that enhance or stabilize $\Delta\psi$, and these compounds are expected to have remedial, therapeutic, palliative, rehabilitative, preventative, prophylactic or disease-impeditive effects on patients suffering from, or thought to predisposed to developing, AD. The ET-based assay of $\Delta\psi$ of the invention can also be used to estimate which agent(s) are most likely to be effective for a given individual, in that an AD patient having mitochondria that exhibit an altered $\Delta\psi$ is expected to be more likely to respond to agents that modulate $\Delta\psi$ than an AD patient having mitochondria with a normal $\Delta\psi$.

Other Neurological Disorders

Similar theories have been advanced for analogous relationships between mitochondrial defects and other neurological diseases, including Alzheimer's disease, Leber's hereditary optic neuropathy, schizophrenia, "mitochondrial encephalopathy, lactic acidosis, and stroke" (MELAS), and "myoclonic epilepsy ragged red fiber syndrome" (MERRF).

Increasing evidence points to the fundamental role of mitochondrial dysfunction in chronic neurodegenerative diseases (Beal, *Biochim. Biophys. Acta* 1366: 211–223, 1998), and recent studies implicate mitochondria for regulating the events that lead to necrotic and apoptotic cell death (Susin et al., *Biochim. Biophys. Acta* 1366: 151–168, 1998). Stressed (by, e.g., free radicals, high intracellular calcium, loss of ATP, among others) mitochondria may release preformed soluble factors that can initiate apoptosis through an interaction with apoptosomes (Marchetti et al., *Cancer Res.* 56:2033–2038, 1996; Li et al., *Cell* 91:479–489, 1997). Release of preformed soluble factors by stressed mitochondria, like cytochrome c, may occur as a consequence of a number of events. In any event, it is thought that the magnitude of stress (ROS, intracellular calcium levels, etc.) influences the changes in mitochondrial physiology that ultimately determine whether cell death occurs via a necrotic or apoptotic pathway. To the extent that apoptotic cell death is a prominent feature of degenerative diseases, mitochondrial dysfunction may be a critical factor in disease progression. To the extent that $\Delta\psi$ depression or collapse is a causative or compounding factor in degenerative disorders, individuals suspected of having or being predisposed to developing such disorders may be identified using the ET-based assay $\Delta\psi$ of the invention. The ET-based $\Delta\psi$ assay of the invention can also be used to identify and characterize agents that enhance or stabilize $\Delta\psi$, and these agents are expected to have remedial, therapeutic, palliative, rehabilitative, preventative, prophylactic or disease-impeditive effects on patients suffering from, or thought to be predisposed to developing, such disorders. The ET-based assay of $\Delta\psi$ of the invention can also be used to estimate which agent(s) are most likely to be effective for a given individual, in that a patient having mitochondria that exhibit an altered $\Delta\psi$ is expected to be more likely to respond to agents that modulate $\Delta\psi$ than a patient having mitochondria with a normal $\Delta\psi$.

Stroke

In contrast to chronic neurodegenerative diseases, neuronal death following stroke occurs in an acute manner. A vast amount of literature now documents the importance of mitochondrial function in neuronal death following ischemia/reperfusion injury that accompanies stroke, cardiac arrest and traumatic injury to the brain. Experimental support continues to accumulate for a central role of defective energy metabolism, alteration in mitochondrial function leading to increased oxygen radical production and impaired intracellular calcium homeostasis, and active mitochondrial participation in the apoptotic cascade in the pathogenesis of acute neurodegeneration.

A stroke occurs when a region of the brain loses perfusion and neurons die acutely or in a delayed manner as a result of this sudden ischemic event. Upon cessation of the blood supply to the brain, tissue ATP concentration drops to negligible levels within minutes. At the core of the infarct, lack of mitochondrial ATP production causes loss of ionic homeostasis, leading to osmotic cell lysis and necrotic death. A number of secondary changes can also contribute to cell death following the drop in mitochondrial ATP. Cell death in acute neuronal injury radiates from the center of an infarct where neurons die primarily by necrosis to the penumbra where neurons undergo apoptosis to the periphery where the tissue is still undamaged (Martin et al., *Brain Res. Bull.* 46:281–309, 1998).

Much of the injury to neurons in the penumbra is caused by excitotoxicity induced by glutamate released during cell lysis at the infarct focus, especially when exacerbated by bioenergetic failure of the mitochondria from oxygen deprivation (MacManus and Linnik, *J. Cerebral Blood Flow Metab.* 17:815–832, 1997). The initial trigger in excitotoxicity is the massive influx of $Ca^{2+}$ primarily through the NMDA receptors, resulting in increased uptake of $Ca^{2+}$ into the mitochondria (reviewed by Dykens, "Free radicals and mitochondrial dysfunction in excitotoxicity and neurodegenerative diseases" in *Cell Death and Diseases of the Nervous System*, V. E. Koliatos and R. R. Ratan, eds., Humana Press, New Jersey, pages 45–68, 1999). The $Ca^{2+}$ overload collapses the mitochondrial membrane potential ($\Delta\Psi_m$) and induces increased production of reactive oxygen species (Dykens, *J Neurochem* 63:584–591, 1994; Dykens, "Mitochondrial radical production and mechanisms of oxidative excitotoxicity" in *The Oxygen Paradox*, K. J. A. Davies, and F. Ursini, eds., Cleup Press, U. of Padova, pages 453–467, 1995). If severe enough, $\Delta\Psi_m$ collapse and mitochondrial $Ca^{2+}$ sequestration can induce opening of a pore in the inner mitochondrial membrane through a process called mitochondrial permeability transition (MPT), indirectly releasing cytochrome c and other proteins that initiate apoptosis (Bernardi et al., *J Biol Chem* 267:2934–2939, 1994; Zoratti et al., *Biochim Biophys Acta* 1241:139–176, 1995; Ellerby et al., *J Neurosci* 17:6165–6178, 1997). Consistent with these observations, glutamate-induced excitotoxicity can be inhibited by preventing mitochondrial $Ca^{2+}$ uptake or blocking MP (Budd et al., *J. Neurochem* 66:403–411, 1996; White et al., *J. Neurosci* 16:5688–5697, 1996; Li et al., *Brain Res* 753:133–140, 1997; Stout et al., *Nat. Neurosci.* 1:366–373, 1998).

Agents and methods that maintain mitochondrial integrity during transient ischemia and the ensuing wave of excitotoxicity would be expected to be novel neuroprotective agents with utility in limiting stroke-related neuronal injury. Given the limited therapeutic window for blockade of necrotic death at the core of an infarct, it may be particularly desirable to develop therapeutic strategies to limit neuronal death by preventing mitochondrial dysfunction in the non-necrotic regions of an infarct. As explained in more detail in Example 9 herein, such agents may be isolated by screening collections of compounds for their ability to stabilize $\Delta\psi$ under excitotoxic conditions that mimic transient ischemia. Such agents are expected to have remedial, therapeutic, palliative, rehabilitative, preventative, prophylactic or disease-impeditive effects on patients who have had, or who are thought to be predisposed to have, strokes. The ET-based assay of $\Delta\psi$ of the invention can also be used to estimate which agent(s) are most likely to be effective for a given individual, in that a patient having mitochondria that exhibit an altered $\Delta\psi$ is expected to be more likely to respond to agents that modulate $\Delta\psi$ than a patient having mitochondria with a normal $\Delta\psi$.

Hyperproliferative Disorders

Whereas mitochondria-mediated apoptosis may be critical in degenerative diseases, it is thought that disorders such as cancer involve the unregulated and undesirable growth (hyperproliferation) of cells that have somehow escaped a mechanism that normally triggers apoptosis in such undesirable cells. Enhanced expression of the anti-apoptotic protein Bcl-2 and its homologues is involved in the pathogenesis of numerous human cancers. Bcl-2 acts by inhibiting programmed cell death and overexpression of Bcl-2, and the related protein Bcl-$X_L$, block mitochondrial release of cytochrome c from mitochondria and the activation of caspase 3 (Yang et al, Science 275:1129–1132, 1997; Kluck et al., Science 275:1132–1136, 1997; Kharbanda et al., Proc. Natl. Acad. Sci. U.S.A. 94:6939–6942, 1997). In contrast, overexpression of Bcl-2 and Bcl-$X_L$ protect against the mitochondrial dysfunction preceding nuclear apoptosis that is induced by chemotherapeutic agents. In addition, acquired multi-drug resistance to cytotoxic drugs is associated with inhibition of cytochrome c release that is dependent on overexpression of Bcl-$X_L$ (Kojima et al., J. Biol. Chem. 273:16647–16650, 1998).

There is a need for compounds and methods that inhibit the growth or enhance the death of cells and tissues that have escaped appropriate apoptotic signals, as well as cytotoxic agents that cause the death of undesirable (e.g., cancer) cells by triggering the apoptotic cascade or otherwise. In particular, because mitochondria are mediators of apoptotic events, agents that stimulate mitochondrially mediated pro-apoptotic events would be especially useful. Because mitochondria have been implicated in apoptosis, it is expected that agents that interact with mitochondrial components will effect a cell's capacity to undergo apoptosis. Such agents are expected to have remedial, therapeutic, palliative, rehabilitative, preventative, prophylactic or disease-impeditive effects on patients suffering from, or thought to be predisposed to developing, hyperproliferative diseases such as cancer and psoriasis. The ET-based assay of $\Delta\psi$ of the invention can also be used to estimate which agent(s) are most likely to be effective for a given individual, in that a patient having mitochondria that exhibit an altered $\Delta\psi$ is expected to be more likely to respond to agents that modulate $\Delta\psi$ than a patient having mitochondria with a normal $\Delta\psi$.

The ET-based assay of mitochondrial $\Delta\psi$ of the invention may also be used to identify agents that are selectively cytotoxic for hyperproliferative or other undesirable cell types. For example, $\Delta\psi$ is elevated in some carcinoma cell lines, and agents that accumulate in mitochondria as a function of $\Delta\psi$ (such as rhodamine 123) are preferentially cytotoxic to such carcinoma cells (Modica-Napolitano et al., Cancer Res. 47:4361–4365, 1987; Andrews et al., Cancer Res. 52:1895–1901, 1992).

In sum, the invention may be used to develop assays for subcellular conditions or intracellular processes, such as changes in mitochondrial $\Delta\psi$, in order to identifty and characterize agents to treat degenerative disorders and diseases as well as hyperproliferative diseases. The ET-based assay of $\Delta\psi$ can be used to identify, depending on the disease or disorder for which treatment is sought, agents that are mitochondria protecting agents, anti-apoptotic agents or pro-apoptotic agents.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLES

Example 1

Selection of Compounds and Optimization of Conditions for ET-based Assays

In order to develop an ET-based assay to detect conditions within a subcellular compartment (such as an organelle or a membrane-bounded portion thereof), and monitor changes thereof, it is necessary to determine appropriate pairs of donor and acceptor compounds and useful concentrations thereof. Using the information and methods presented herein, one skilled in the art can readily determine donor and acceptor compounds, and concentrations thereof, appropriate for a variety of such assays.

One step in the process of developing an ET-based assay involves optimizing concentrations of the donor and acceptor compounds, as well as other conditions for the assay. In general, with regards to the concentrations of the donor and acceptor compounds, at least two criteria apply. First, the concentrations of the donor and acceptor compounds should be sufficient for energy transfer to occur. Second, the concentration of each compound should be low enough that (a) any non ET-based signal from the compounds is negligible, so that the background signal in the assay is minimal, and (b) any undesirable effects on cellular physiology, including cellular toxicity, and/or effects on the subcellular compartment of interest, are minimal. It should be noted, however, that not every compound will have undesirable effects on cellular physiology.

In the case of a FRET-based assay of $\Delta\psi$ using NAO and TMRM, these criteria are applied as follows. Because NAO is known to be toxic to some cells at higher concentrations (Maftah et al., FEBS Lett. 260:236–240, 1990), such as, e.g., >10 $\mu$M, it should generally not be applied at such concentrations. The concentration of NAO at which such toxicity may occur may vary depending on the cell line used in a given experiment and other conditions such as, e.g., time of exposure, whether or not other toxic or protective factors are present, and the like. However, one skilled in the art will be able to determine and correct for such variations by altering, for example, the concentration of NAO or time of exposure relative to the conditions presented herein.

A series of experiments were carried to determine the optimum ratio and concentrations of NAO and TMRM for a FRET-based assay of $\Delta\psi$. These tests can be applied to other pairs of donor and acceptor compounds in other ET-based assays.

General Protocols

The FRET-based assay of $\Delta\psi$ was generally carried out in the following manner, although variations to these general procedures can be made without affecting the sensitivity, accuracy or efficiency of the assay.

Cell Lines and Preparation Thereof

A variety of cell lines were used in the following experiments. The neuroblastoma cell line SH-SY5Y is a multiply subcloned cell line of human origin (Perez-Polo et al., Dev. Neurosci. 5:418–423, 1982). The SH-SY5Y cell line is a well-characterized cell line that is capable of differentiating into neuron-like cells and is an accepted cellular model for a variety of neuronal cell functions (for reviews, see Vaughan et al., *Gen. Pharmacol.* 26:1191–1201, 1995; Pahlman et al., *Acta Physiol. Scand. Suppl.* 592:25–37, 1990).

Cybrid (cytoplasmic hybrid) cells comprise a nuclear component from one cell type and a cytoplasmic (including mitochondrial) component from another cell type. Procedures for preparing cybrid cells comprising mitochondria derived from patients having Alzheimer's disease have been previously described (Miller et al., *J. Neurochem.* 67:1897–1907, 1996; Swerdlow et al., *Neurology* 49:918–925, 1997; and U.S. Pat. No. 5,888,498, all of which are hereby incorporated by reference). The 1685 cybrid cell line is one example of a cybrid cell line of this type. The 1685 cybrid cell line was created by fusing platelets from an AD donor with SH-SY5Y neuroblastoma cells that had been made rho$^0$ by extended treatment with ethidium bromide. "MixCon" designates a Mixed Control composed of cybrids prepared in like fashion but using platelets from n normal age-matched patients (n=2–3, depending on the particular experiment).

NCI-H460 is a human lung large cell carcinoma cell line available from the American Type Culture Collection (ATCC, Manassas, Va.) under accession No. ATCC HTB-177. A preferred cellular medium for NCI-H460 cells is 90% (RPMI 160 medium with 2 mM L-glutamine, 1.5 g/L sodium carbonate, 4.5 g/L glucose, 10 mM HEPES and 1.0 mM sodium pyruvate), 10% (fetal bovine calf serum).

MCF-7 is a human breast carcinoma cell line available from the ATCC under accession No. ATCC HTB-22. MCF-7 has been used in studies of the relationship between disruption of mitochondrial $\Delta\psi$ and apoptotic events (see, e.g., Heerdt et al., *Cancer Res.* 59:1584–1591, 1999). A preferred cellular medium for MCF-7 cells is 90% (minimum essential medium Eagle medium with 2 mM L-glutamine and Earle's BSS, 1.5 g/L sodium carbonate, 0.1 mM non-essential amino acids and 1.0 mM sodium pyruvate), 10% (fetal bovine calf serum with 10 ug/ml bovine insulin).

In general, cells were plated at about 2 to $3\times10^4$ cells per well on 96-well microplates (Costar, black wall; clear, flat bottom) at least about 24 hours prior to the assay. HBSS was generally used as cellular media but any media appropriate for a given cell line may be used in the assay.

Preparation of Donor and Acceptor Compounds

A 5 mg/ml stock solution of the ET donor compound, nonylacridine orange (NAO, Molecular Probes, Inc., Eugene, Oreg.; catalog #A1372), was prepared in DMSO. The stock solution was aliquoted into microfuge tubes and stored frozen at −20° C. until thawed on ice immediately prior to the assay. Unless otherwise specified, for use in assays the 5 mg/ml NAO stock solution was diluted 1:5000 in Hank's balanced salt solution (HBSS, Life Technologies, Grand Island, N.Y.) to yield a working stock solution containing 1 μg/ml NAO, which was further diluted as indicated below.

A stock solution of acceptor compound, 100 mM TMRM (Molecular Probes, Inc., Eugene, Oreg.; catalog #T668), was prepared in DMSO. This concentration corresponds to 20,000×the final concentration used in the assay. The stock solution was aliquoted into microfuge tubes and stored frozen at −20° C. until thawed on ice immediately prior to the assay.

A combined stock solution was also prepared for ease of manipulation, containing both the ET donor and acceptor compounds (25 mM TMRM and 1 mg/ml NAO, in DMSO (i.e., both ET molecules at 5,000 times the final concentration used in the assay). The combined stock solution was aliquoted into microfuge tubes and stored frozen at −20° C., and thawed on ice immediately prior to the assay.

Instrument Preparation

The FLIPR™ heaters and laser are turned on for at least 1 hour before the assay is performed. Typically, the following settings were used: shutter, 0.4 sec.; f-stop, 0.2; filter, #2; laser at 300 mW (15 A). In later experiments, a special order filter (Omega Optical, Inc., Brattleboro, Vt.) for 530±25 nm was used.

In the FLIPR™ instrument, there are positions for three 96-well microplates. A centrally located 96-well microplate contains samples, and up to two 96-well plates, one on each side of the central plate, containing reagents can be included. In a typical assay, the first reagent 96-well (8 rows, 12 columns) plate was set up so that the wells in Row A contained media (typically, HBSS), the wells in Row B contained a $\Delta\psi$ collapsing agent (typically, CCCP), and the remaining Rows (C through H) contained the test compound (s). Furthermore, in a Type II assay (see Example 5), a second reagent plate was set up so that each well contained an appropriate amount of a $\Delta\psi$ collapsing agent (typically, CCCP) to be added to the samples sometime after the test compound(s).

Fluorophore Loading

Fifteen minutes prior to the assay, the entire plate was gently flicked over a sink to remove the cell media. The displaced media was replaced in each well with 100 ul HBSS that contained 5 uM TMRM and was prewarmed to 37° C. In general, it is preferred to prewarm media and reagents to 37° C. and to maintain cells at 37° C. in order to avoid thermal shock that can itself cause changes in $\Delta\psi$ or cause the death of sensitive cells. Ten minutes later, 20 μl of the NAO working stock solution prepared as described above (1 μg/ml NAO) was added to each well (final concentration, 200 ng/ml, equal to 0.4 μM).

In an optional step, after letting the cells incubate in the presence of both fluorophores for about 5 minutes, excess fluorophore was removed by gently flicking the plate to remove cell media and adding 100 ul prewarmed HBSS to each well; this process was repeated up to three times. After the final plate flicking, 100 ul prewarmed HBSS was added to each well. Cells can be incubated for some period of time, depending on the cell type, before addition of the test compound(s), with no appreciable loss of signal. In the case of SH-SY5Y cells, this incubation period can be up to about 40 minutes.

Assay Readings

Prior to the addition of test compounds, about 20 readings were taken on the FLIPR instrument at 3-second intervals. Although these data are not used in calculating the results of the assay, they are useful for assessing the integrity of the cells and/or monitoring for spontaneous collapse of $\Delta\psi$. For example, if cellular integrity has been compromised, a significant collapse in $\Delta\psi$ would be detected after the optional rinsing step but before addition of the test compounds. Next, the test compounds were added and 175 readings were taken at 5-second intervals.

To determine the ET value corresponding to maximal collapse of $\Delta\psi$ (i.e., $\Delta\psi\sim0$ in theory), a $\Delta\psi$ collapsing agent (e.g., CCCP) was added as follows. In Type I assays (FIG. 3A), the collapsing agent was added to wells distinct from those receiving the test compounds at roughly the same time that the test compounds were added, and readings of these wells were taken at the same time as readings were taken of the wells that received test compounds. In Type II assays (FIG. 3A), the collapsing agent was added to the same wells that received the test compounds after readings had been taken at 5-second intervals for a period of time (typically about 9–15 minutes), and readings were then taken for a second period of time roughly equivalent to the first period of time.

Data Analysis

The assay results are presented as plots of relative fluorescence units (RFU) over time (FIG. 6) for qualitative analysis. For quantitative analyses, calculations were as follows:

For Type I assays, the initial instrument reading for each well was set to zero. The readings taken at 5-second intervals following those taken at 3-second intervals to verify cellular integrity, typically readings numbered from about reading 21 to about reading 195–200, were summed ($\Sigma F_x$). Tests of significance for multiple (i.e., >2) groups, such as one-way ANOVA of treatment groups with no transform, Newman-Keuls or Bonferroni (Dunn's) multi-comparisons, were used to evaluate the significance of results.

For Type II assays, the initial instrument reading for each well was set to zero, and readings taken at 5-second intervals (following integrity confirmation) numbered from about 21 to about 195–200 were summed ($\Sigma F_x$). For normalization, the readings during the final 4 minutes (i.e., readings numbers about 214 to 230) after addition of the $\Delta\psi$ collapsing agent (CCCP) to maximally compromise membrane potential were averaged ($F_{CCCP}$). Because the use of ratios would violate mathematical assumptions inherent in ANOVA algorithms, the data were transformed (log or arcsin) before being evaluated for significance in one-way ANOVA analyses.

For either type of assay, sums and averages for each well were calculated using the software provided with the FLIPR™ instrument, exported into EXCEL™ (Microsoft, Inc., Redmond, Wash.) via *.txt, and finally exported into GB Stat for ANOVA. FLIPR™ kinetic data are exported into EXCEL for mean and standard error calculations of the readings taken over the time courses. It is desirable, but not necessary, to back up all FLIPR™ data on CD, or another appropriate machine-readable format, on a daily basis.

Results

In an initial set of experiments, MixCon cybrid cells were treated with six different concentrations of TMRM (0, 1.25, 2.5, 5.0, 10 and 20 uM) and NAO (0, 6, 12, 25, 50, 100, 200 and 400 ng/ml; respectively, 0, 13, 26, 52, 105, 210, 420 and 840 nM) on a 96-well plate. Each of the 48 possible combinations of TMRM and NAO concentrations were tested in duplicate using a FLIPR instrument using a 0.1 second shutter with the laser set at 300 mW and readings taken using a 510–590 nm filter. CCCP was added to all samples (1.5 uM) at 1 minute after the plate was put into the FLIPR™ instrument.

If FRET occurs between NAO and TMRM, which localize to the inner mitochondrial membrane and the mitochondrial matrix, respectively, then a change in FRET-based signal should occur following CCCP addition. That is, the addition of CCCP should cause $\Delta\psi$ to be decreased and, as a consequence, the mitochondrial concentration of the acceptor compound (TMRM) decreases as TMRM leaves the mitochondria and/or is taken up less by mitochondria. Because the donor compound (NAO) is retained by mitochondria regardless of $\Delta\psi$, the donor and acceptor compounds ceased to be in sufficient proximity to one another for FRET to occur, and the signal resulting from FRET decreases, as indicated by a change in fluorescence (expressed in relative fluorescence units, RFU).

The energy transfer from NAO to TMRM can be measured either directly or indirectly (see FIG. 1). Direct measurement of NAO→TMRM FRET involves exciting the donor, NAO, at an appropriate wavelength for its excitation [$\lambda D(ex)$], which in turn emits energy at a wavelength [$\lambda D(em)$] that overlaps the excitation spectrum of the acceptor, TMRM, and measuring the emission from excited TMRM molecules at ore near their peak emission wavelength [$\lambda A(em)$]. Indirect measurement of NAO →TMRM FRET also involves exciting NAO at $\lambda Dex$, but it is the emission from the donor NAO, not from the acceptor TMRM, that is measured (i.e., $\lambda D(em)$ is measured rather than $\lambda A(em)$). If energy transfer occurs efficiently from the exicted donor (NAO) to the acceptor (TMRM), then emissions from the donor will be "quenched" and the signal at $\lambda D(em)$ will be minimal. If and when the acceptor compound ceases to be proximal to the donor, energy transfer will cease to occur and the emissions from the donor will be "dequenched" (i.e., the signal at $\lambda D(em)$ will increase).

In the present case, FRET was measured indirectly. That is, the cells were treated with light having a wavelength of 488 nm (near $\lambda D(ex)$ for NAO, 485 nm) and the signal at 530±25 nm (near $\lambda D(em)$ for NAO) was measured over time after CCCP addition. The expected result is that, if FRET occurs between the donor NAO and the acceptor TMRM, the addition of CCCP (which results in a decreased concentration of TMRM in the mitochondria) should yield a dequenching of the signal from NAO (i.e., increasing fluorescence at or near $\lambda Dem$). In contrast, if FRET had been measured directly, the signal at or near $\lambda D(em)$ for TMRM would have been measured and expected to decrease following the addition of CCCP and mitochondrial exodus of TMRM.

Figure 4:
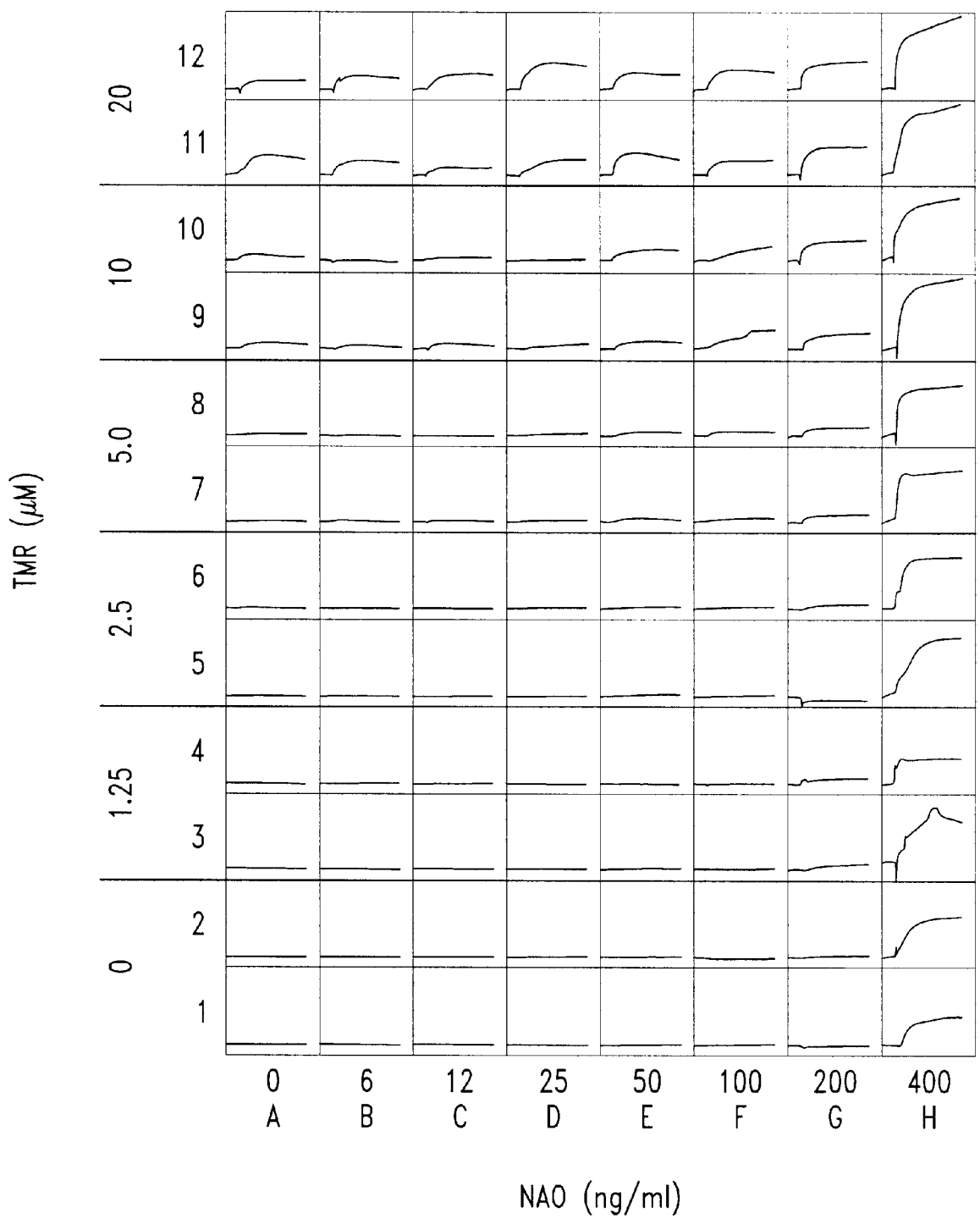
FIG. 4 shows titration of an ET donor molecule (NAO) and an ET acceptor molecule (TMRM) in FRET assays of $\Delta\psi_m$.

The results of the experiment are shown in FIG. 4. In these results, FRET is seen as an increase in signal (dequenching of NAO emission) that occurs following CCCP addition only when both donor and acceptor compounds are present at a given set of concentrations, i.e., does not occur when either the acceptor or donor compound alone is present at the same concentration. For example, in FIG. 4, FRET occurs in wells E9, E10, F9, F10, 9G and 10G; compare the signal in these cells to that in wells A9 and A10 (NAO absent) and wells F1 and F2 (TMRM absent). Although FRET is probably occurring in other wells in the extreme upper righthand portion of FIG. 4, the signal in these wells may also include a significant contribution from background signal from NAO alone (compare wells H11 and H12 to H1 and H2) or TMRM alone (compare wells H11and H12 to A11 and A12). Based on these results, optimal concentrations of NAO and TMRM for the assay include 50 ng/ml NAO and 10 uM TMRM (wells E9 and E10), 100 ng/ml NAO and 10 uM TMRM (wells F9 and F10), 200 ng/ml NAO and 10 uM TMRM (wells G9 and G10 ), and 200 ng/ml NAO and 5 uM TMR (wells G7 and G8).

Figure 5:
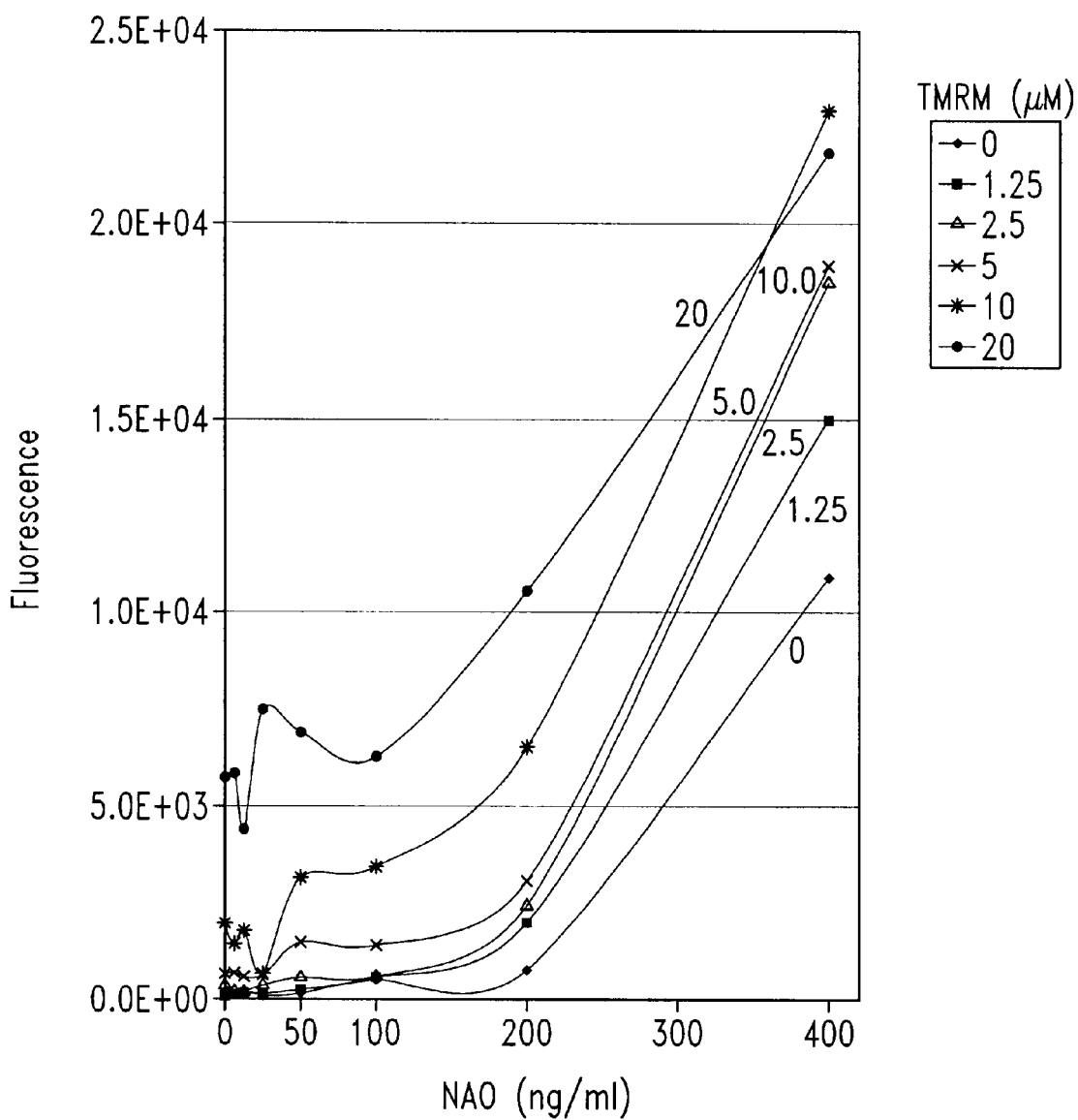
FIG. 5 shows calibration of the concentrations of an ET donor molecule (NAO) and an ET acceptor molecule (TMRM) in FRET assays of $\Delta\psi_m$.

The data in FIG. 4 were analyzed as described above for the Type I assay, i.e., the initial reading for each well was set to zero, and the RFU readings taken from about 21 to about 175 seconds were summed ($\Sigma F_x$). The results for varying concentrations of TMRM are graphed as a function of NAO concentration in FIG. 5. FRET occurred at 50, 100 and 200 ng/ml of NAO with 5 or 10 uM TMRM, as evidenced by the increase in signal at these concentrations (compare the 5 and 10 uM TMRM curves in the 50–200 ng/1 ml NAO range with the 0, 1.25 and 2.5 uM TMRM curves in the same range of NAO concentrations).

Figure 6:
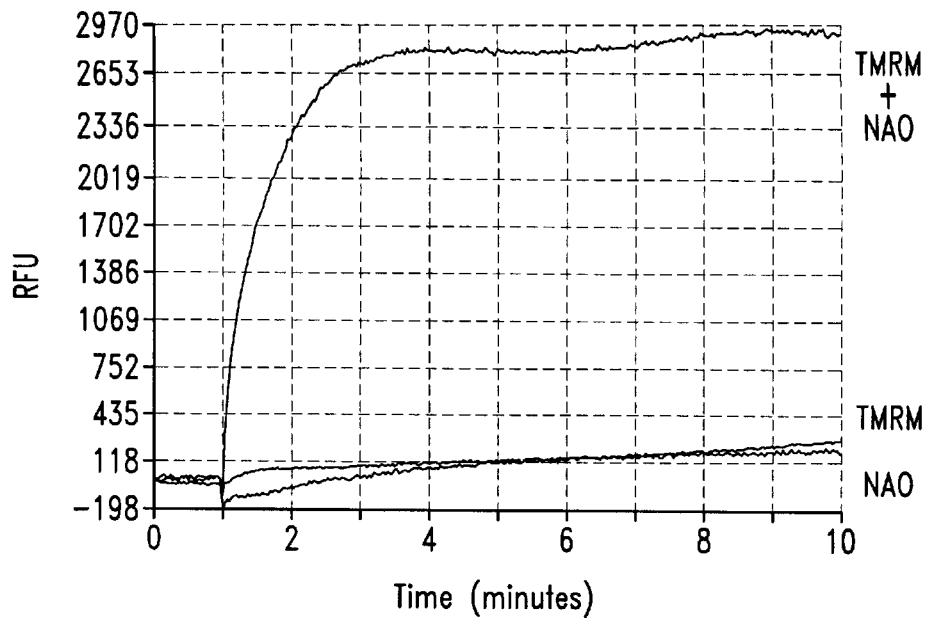
FIG. 6 shows time-course data from a FRET assay of $\Delta\psi_m$ using NAO and TMRM alone and in combination.

In another experiment designed to examine the background signal from each fluorophore individually as well as time course of CCCP-mediated $\Delta\psi$ collapse, FRET was measured in cells treated with either 5 uM TMRM, 420 nM NAO, or with both compounds, for a more extended period after CCCP addition (1.5 uM). As shown in FIG. 6, a rapid increase in fluorescence occurred within the first two minutes after CCCP addition, after which the change in fluorescence reached a plateau. When either NAO or TMRM was present alone, the fluorescent signal was essentially constant.

In order to determine if the NAO dequenching signal that is measured in the FRET-based assay is linear over different cell densities, the following experiments were performed. Different numbers of MixCon or 1685 cybrid cells were preincubated in replicate in wells of 96-well plates for about 10 minutes with 5 uM TMRM, after which 4 ng/ml NAO was added and the cells were incubated for an additional 5 minutes. Finally, CCCP (1 uM) was added to each well, and fluorescence signals were monitored at 530±25 nm using a FLIPR™ device. Mitochondrial efflux of TMRM then took place, as demonstrated by an increase in fluorescence signal corresponding to the dequenching of NAO emissions over time. The initial slopes of the curves (RFU over time) were plotted against the number of cells per well. The results show that the $\Delta\psi$-dependent fluorescent signal increases in a linear fashion over the range of from about 38,000 to about 330,000 cells per well.

Although many of the experiments described herein make use of a FLIPR instrument, and involve a series of measurements over time, the invention may be carried out using any instrument or device of sufficient sensitivity capable of monitoring at least two time points (i.e., before and after addition of an agent that affects $\Delta\psi$). In one experiment, for example, MixCon and 1685 cybrid cells were preincubated with TMRM and NAO as above, and fluorescence at 538 nm was measured using an fmax™ fluorimetric plate reader (excitation=485 nm) and then treated with CCCP (final concentartion, 1.3 uM). Ten minutes later, the fluorescence at 538 nm was again determined, and found to have increased significantly as compared to cells treated with buffer in all three cell types.

Moreover, the 1685 cybrid cell line, which comprises mitochondria from a patient having Alzheimer's disease, was more sensitive to ionomycin, i.e., showed a greater degree of loss of $\Delta\psi$ than the control cybrid cells (MixCon) or the parental SH-SY5Y cell line. This result demonstrates that the assay can be used to detect differences among cell types in reactions to agents that influence $\Delta\psi$.

Example 2

Parameter-Dependent Co-Localization of Acceptor-Donor Compounds

Another step in the process of developing an ET-based assay to detect conditions within a subcellular compartment (such as an organelle or a membrane-bounded portion thereof), and monitor changes thereof, is to confirm that not only do the donor and acceptor compounds co-localize in sufficient proximity for energy transfer to occur, but also that such co-localization is dependent on the state of the parameter to be measured. That is, at least one of the compounds must localize to (accumulate in) the subcellular compartment of interest as a function of the measured parameter, and must leave that compartment and/or accumulate less rapidly or efficiently in that compartment as that parameter changes.

For example, for an ET-based assay designed to measure $\Delta\psi$ of mitochondria, one of the compounds (either the donor or the acceptor) must accumulate in and/or be released from mitochondria in a manner that is dependent on $\Delta\psi$, whereas the presence of the other compound (the acceptor or donor, respectively) in mitochondria must be $\Delta\psi$-independent. Combining these criteria with the information presented herein, one skilled in the art can readily choose donor-acceptor combinations that are appropriate for ET-based $\Delta\psi$ assays.

Compounds whose mitochondrial concentration is not dependent on $\Delta\psi$ include, by way of example and not limitation, NAO (Petit et al., *Eur. J. Biochem.* 194:389–397, 1990; Maftah et al., *Biochem. Biophys. Res. Comm.* 164:185–190, 1989), MitoTracker® Green FM (U.S. Pat. Nos. 5,459,268 and 5,686,261), MitoFluor™ Green (Haugland, *Handbook of Fluorescent Probes and Research Chemicals*, 6th Ed., Spence, ed., Molecular Probes, inc., Eugene, Oreg., 1996, page 269) and fusion proteins comprising (a) a red- or yellow-shifted Green Fluorescent Protein polypeptide, or a "FLASH" polypeptide, and (b) a polypeptide sequence that localizes the fusion protein to the mitochondrial matrix or inner membrane. These compounds are listed as Group IV and V donor compounds in Table 2. A series of representative Group IV and V acceptor compounds is also presented in Table 2. Of the Group IV and V acceptor compounds in Table 2, ones that accumulate in mitochondria in a $\Delta\psi$-dependent manner include, by way of example and not limitation, rhodamine 123 (Emaus et al., *Biochim. Biophys. Acta* 850:436–448, 1986; Scaduto et al., *Biophys. J.* 76:469–477, 1999), TMRM and TMRE (Farkas et al., *Biophys. J.* 56:1053–1069, 1989; Ehrenberg et al., *Biophys. J.* 53:785–794, 1988).

With regard to specific sites of accumulation of these compounds, NAO specifically interacts with the inner mitochondrial membrane (Maftah et al., *Biochem. Biophys. Res. Comm.* 164:185–190, 1989). TMRM, TMRE and rhodamine 123 are thought to localize to the mitochondrial matrix, but a recent report indicates that these compounds additionally accumulate reversibly in the inner and outer aspects of the inner mitochondrial membrane because of localized intensification of membrane potential at sites there (Scaduto et al., *Biophys. J.* 76:469–477, 1999). In any event, whether TMRM, TMRE and rhodarnine 123 localize to either the inner mitochondrial membrane, or the mitochondrial matrix (or both), they are expected to be in close proximity to the inner mitochondrial membrane, where NAO localizes (see FIG. 1).

In order to confirm that FRET only occurs between appropriately localized donor-acceptor pairs of compounds in living cells, the following experiment was carried out. SH-SY5Y cells were cultured and assayed as in Example 1 with the following exceptions. Cells were incubated with an "acceptor" compound at 5 uM for 10 minutes, and then further incubated with a "donor" compound at 4 ng/ml for an additional 10 minutes. At this time, an agent that collapses $\Delta\psi$, CCCP, was added to the cells at a concentration of 1 uM, and relative fluorescence was measured using an fmax™ fluorimetric plate reader (excitation, 485 nm; emission read at 538 nm±20 nm). The mean rate of change in relative fluorescent units (RFU) in 6 to 8 replicate wells was calculated as the slope of the curve over the initial 3.5 minutes using the software provided with the fmax™ instrument via least squares linear regression.

The results are shown in Table 4. FRET occurred between NAO and TMRM, which localize to the inner mitochondrial membrane and the mitochondrial matrix, as indicated by the mean rate of RFU change following CCCP addition. That is, FRET occurred between NAO and TMRM until the addition of CCCP. The addition of CCCP caused $\Delta\psi$ to be decreased and the acceptor compound (TMRM) to leave the mitochondria. Because the donor compound (NAO) is retained by mitochondria regardless of $\Delta\psi$, the donor and acceptor compounds ceased to be in sufficient proximity to one another for FRET to occur, and the signal resulting from FRET decreased (as indicated by the relatively rapid rate of change in RFU).

In contrast to the effect seen with NAO and TMRM, when calcein or CO-Fluor were used as "donor" compounds, the rate of RFU change following CCCP addition was negligible. This reflects the fact that, although calcein and CO-Fluor have emission peaks similar to that of NAO, they do not localize to mitochondria and thus are not in close enough proximity to the "acceptor" compound (the mitochondrially localized TMRM) for FRET to occur. In like fashion, when SNAFL, which does not localize to mitochondria, was used as an "acceptor" compound and NAO was used as a "donor" compound, FRET was not observed, even though the excitation peak wavelength of SNAFL (514 nm) is closer to emission peak wavelength of NAO (517 nm) than the excitation peak wavelength of TMRM (544 nm). Thus, as expected, for energy transfer to occur, both spectral overlap and physical proximity are required.

TABLE 4

FRET Only Occurs Between Appropriately Co-Localized Donor and Acceptor Compounds

| "Donor" Compound | | "Acceptor" Compound | | | Mean Rate of RFU Change |
|---|---|---|---|---|---|
| λD(ex) | λD(em) | λA(ex) | λA(em) | | |
| NAO 495 nm | 519 nm | 548 nm | 573 nm | TMRM | 0.3750*** |
| Calcein 494 nm | 517 nm | 548 nm | 573 nm | TMRM | 0.0050*** |
| CO-Fluor 492 nm | 517 nm | 548 nm | 573 nm | TMRM | 0.0025*** |
| NAO 495 nm | 519 nm | 514 nm | 546 nm | SNAFL | 0.0025*** |

In sum, energy transfer (in this example, FRET) occurs only when the donor and acceptor compound are appropriately co-localized within the subcellular compartment of interest. Moreover, processes that cause the donor or acceptor compound to localize to a different site in such a manner that the pair of compounds are no longer in sufficient proximity for energy transfer to occur can be monitored and assayed by measuring changes in a signal generated as a result of the energy transfer.

Example 3

Parameter-Dependent Changes in Energy Transfer

The preceding Examples show how it can be determined that energy transfer occurs between a donor and acceptor compound, how to optimize conditions including concentrations of the donor and acceptor compound, and how to demonstrate that energy transfer is dependent upon co-localization of both compounds within the same or adjacent subcellular sites. In order to demonstrate that an ET-based assay detects the condition or parameter within a subcellular compartment of interest, and monitor changes thereof, it is useful to validate the assay with agents having known effects on the chosen condition or parameter.

Using a FRET-based assay designed to measure $\Delta\psi$ of mitochondria as a model, a variety of agents are known in the art to lower (dissipate) or eliminate (collapse) $\Delta\psi$. Additionally, some agents are known to increase $\Delta\psi$ above normal levels, i.e., to hyper-polarize mitochondria. Both types of agents were evaluated using the FRET-based assay of $\Delta\psi$.

Agents that Increase $\Delta\psi$

Oligomycin is an example of a compound that hyperpolarizes mitochondria. MixCon cybrid cells were contacted with TMRM (5 uM) and NAO (420 nM) as in Example 1. On the same 96-well plate, a second set of MixCon cells was also treated with 10 $\mu$M oligomycin, dissolved in HBSS buffer for 10 minutes prior to addition to cells, and added to cells 10 minutes before the addition of TMRM. The "initial FRET signal," ie., the first reading before initiating $\Delta\psi$ collapse was determined for eight separate wells of each of the three combinations of cells and agents using a FLIPR™ instrument.

If the agents work as expected, hyperpolarization should increase $\Delta\psi$, leading to increased intramitochondrial TMRM accumulation, leading in turn to increased energy transfer (i.e., NAO quenching). The results (Table 5) show that oligomycin had the predicted effect. That is, because the cells treated with oligomycin contained hyper-polarized mitochondria, the initial FRET signal was significantly less than that seen in cells that were not exposed to oligomycin.

TABLE 5

Effect of Oligomycin on FRET-Based Assay of $\Delta\psi$

| zCells | Oligo-mycin | Initial FRET Signal | Significance* Relative to MixCon, No Oligomycin | Standard Error |
|---|---|---|---|---|
| MixCon | (none) | 521.1 | — | 17 |
| MixCon | 10 uM | 296.2 | P <10⁻⁸ | 13 |

*Calculated via two-tailed t-test

Agents that Decrease $\Delta\psi$ and Protective Agents:
Ionomycin and Bongkrekic Acid The effect on $\Delta\psi$ of the calcium ionophore ionomycin, which dissipates and eventually collapses $\Delta\psi$, alone or in combination with bongkrekic acid (BKA), was compared to the effects of the $\Delta\psi$-collapsing agent CCCP. Because BKA binds to the adenine nucleotide translocator, the activity of which is required for mitochondrial permeability transition (MPT), it was predicted that BKA would have an ameriolating effect on the $\Delta\psi$ dissipation caused by ionomycin. SH-SY5Y cells were treated with donor and acceptor compounds (respectively, NAO, 420 nm, and TMRM, 5 uM) according to the procedure described in Example 1, and HBBS media, CCCP (1.5 uM), ionomycin (5 uM), or ionomycin (5 uM) and BKA (2 uM; preincubated with cells at 37° C. for 10 minutes before TMRM was added). RFU was monitored using a FLIPR™ instrument.

The results (FIG. 7) show that, as in the preceding Examples, CCCP induced a rapid increase in fluorescence due to dequenching of the NAO emission signal, consistent with collapse of $\Delta\psi$ and mitochondrial exodus of the acceptor compound, TMRM. Treatment with ionomycin ultimately yielded a more gradual change in fluorescence, as was expected for an agent known in the art to cause a slower dissipation in $\Delta\psi$ than CCCP. As predicted, the addition of BKA to ionomycin-treated cells was to some degree protective of ionomycin's effects and ultimately resulted in a fluorescence signal that was similar to that seen when HBSS media was added to the cells.

Ionomycin and Ruthenium Red

Figure 8:
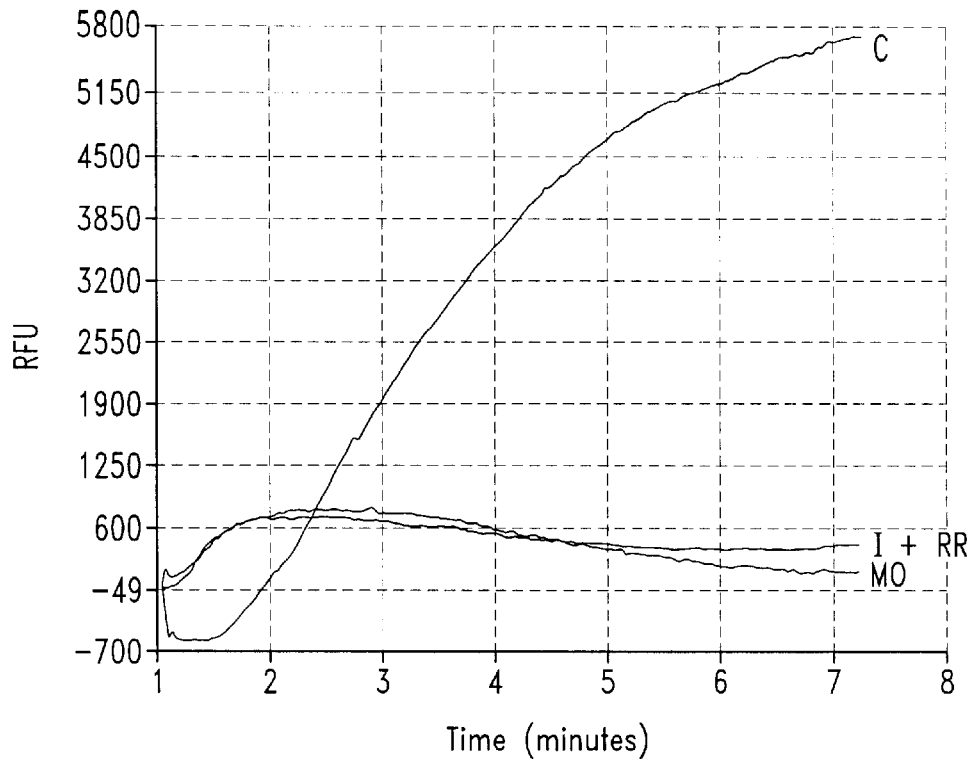
FIG. 8 shows Type I FRET $\Delta\psi_m$ assay of various agents. Symbols: "MO," media (HBSS) only; "C," CCCP; "I+RR," ionomycin and ruthenium red.

Ruthenium red was confirmed to have a protective effect with regards to the $\Delta\psi$-dissipating effects of ionomycin. Ionomycin is an ionophore that increases the level of cytosolic calcium; this leads to a dissipation of $\Delta\psi$ as mitochondria take up calcium from the cytosol. Ruthenium red blocks the activity of the mitochondrial calcium uniporter, thus inhibiting or blocking rnitochondrial uptake of calcium, and thus is expected to counteract the effect of ionomycin. SH-SY5Y cells were prepared and preincubated with NAO and TMRM as in the preceding experiments and treated with CCCP (1.5 uM), ionomycin (5 uM) with ruthenium red (100 uM) and media (1BSS) only. Fluorescence was measured over time at 530±25 nm using a FLIPR™ instrument. The results (FIG. 8) demonstrate that the FRET-based assay yields data that follow the expected patterns, i.e., the ionomycin-mediated dissipation of Δψ is essentially completely blocked by ruthenium red.

Ionomycin or MPP+ and Cyclosporin A

Figure 9:
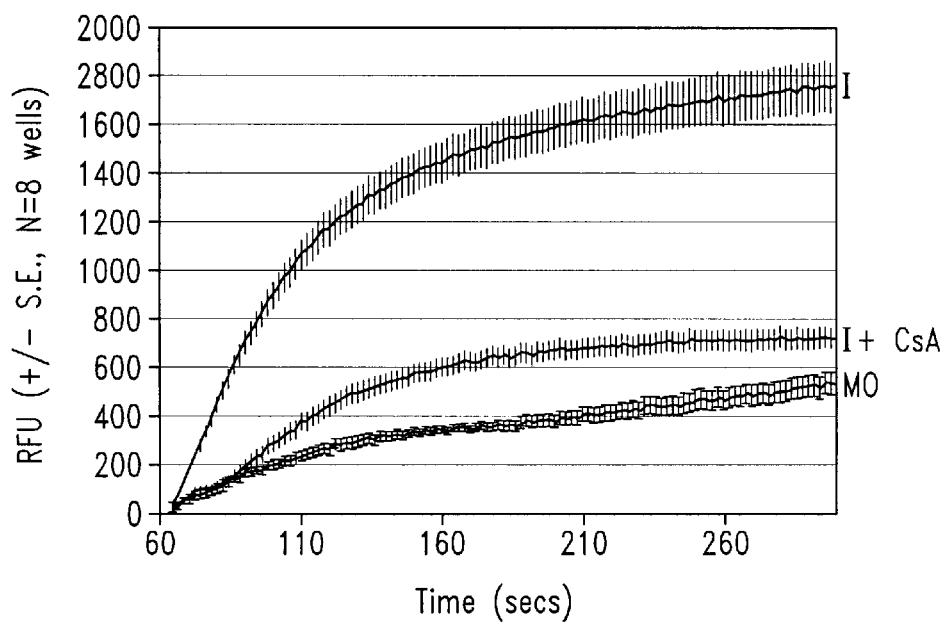
FIG. 9 shows Type I FRET $\Delta\psi_m$ assay of various agents. Symbols: "MO," media (HBSS) only; "I," ionomycin; "I+CsA," ionomycin and cyclosporin A. The vertical lines indicate the standard error for each reading.

In another related experiment, cyclosporin A was confirmed to have a protective effect with regards to the Δψ-dissipating effects of ionomycin. Cyclosporin A binds to cyclophilin D and, like BKA, blocksMPT, and is thus expected to counteract the effect of ionomycin. MixCon cells were prepared and preincubated with NAO and TMRM as in the preceding experiments and treated with ionomycin (5 uM). One group of cells was preincubated with cyclosprin A (10 uM) for 15 minutes prior to CCCP addition. Fluorescence was measured over time at 530±25 nm using a FLIPR™ instrument. The results (FIG. 9) demonstrate that the FRET-based assay yields data that follow the expected patterns, i.e., the ionomycin-mediated dissipation of Δψ is inhibited by cyclosporin A. In other experiments, the assay was used to confirm that cyclosporin A (10 uM, added 10 minutes prior to addition of the Δψ agent) essentially blocks the long-term (>10 minutes after addition) dissipation and collapse of Δψ otherwise caused by 0.5 mM MPP+.

Atractyloside and Cyclosporin A

The assay was also validated by the fact that it showed a dissipation of Δψ in SH-SY5Y cells treated with atractyloside (ATR, 5 mM) that peaked at about 6 minutes after ATR addition. At this concentration of ATR, Δψ recovered after about 15 minutes, whereas CCCP (1 $\mu$M) led to a more complete collapse of Δψ that was maintained for at least 15 minutes. Pretreatment with cyclosporin A (5 $\mu$M, 5 minutes) resulted in a significant moderation of the response to ATR; the peak fluorescent signal in the ATR-plus-cyclosporin A sample was roughly half that of the sample treated with ATR alone.

In sum, energy transfer (in this example, FRET) occurs in a manner that accurately reflects changes in a parameter (in this example, Δψ) known to influence the concentration of the donor and/or acceptor compounds (in this example, the concentration of the acceptor compound TMRM decreases as a function of decreasing Δψ). Moreover, the measured activities of agents known to increase (e.g., oligomycin) or decrease (e.g., CCCP, ionomycin, MPP+, ATR) the chosen parameter (Δψ) are in agreement with their predicted effects. The same is true for protective agents (BKA, ruthenium red, cyclosporin A) that are known to counteract, in whole or in part, the effects of parameter-changing agents. These results indicate that the ET-based assay may be used to screen for and evaluate previously uncharacterized compounds for their effects on the chosen parameter (in this example, Δψ) and for their ability to counteract the effects of known compounds on the parameter of interest.

Example 4

Evaluation of Assay Results

Figure 7:
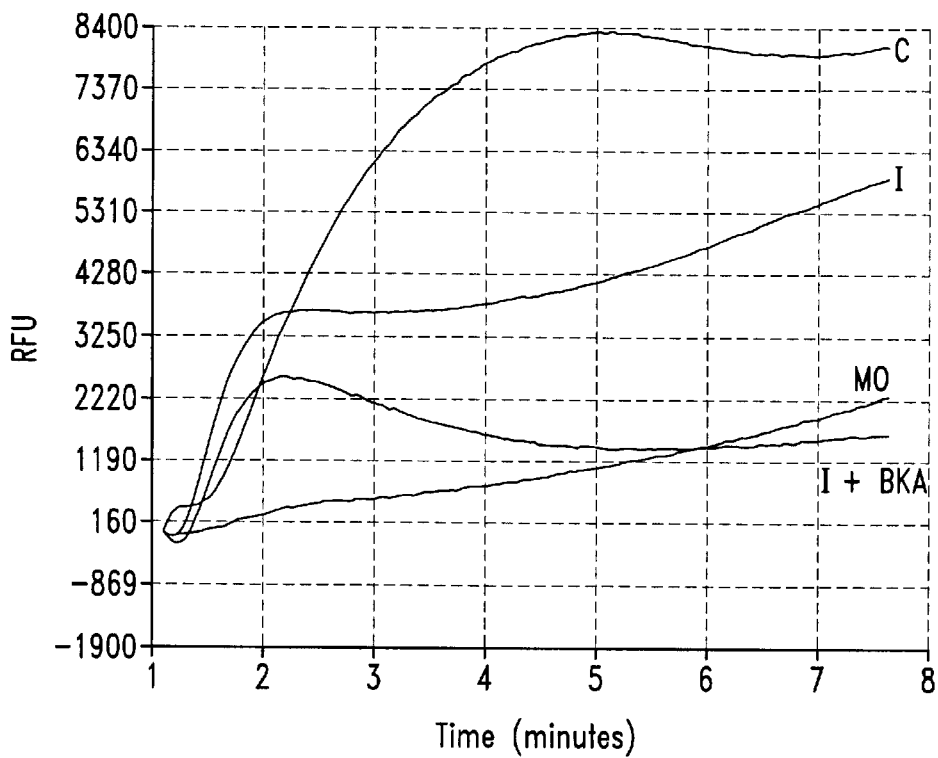
FIG. 7 shows Type I FRET $\Delta\psi_m$ assay using various agents. Symbols: "MO," media (HBSS) only; "C," CCCP; "I," ionomycin; "I+BKA," ionomycin and bongrekic acid.

The results presented in the preceding examples demonstrate the need to evaluate ET-based assay results in a fashion that yields meaningful conclusions. Using the results presented in FIG. 7 as an example, although the initial rates of change in RFU of the samples treated with CCCP, ionomycin or ionomycin and BKA were similar from about 78 seconds to about 127 seconds, the readings for these three samples diverged thereafter and were markedly different at 460 seconds. There are a variety of ways to evaluate the results of an ET-based assay, and examples of these using the results shown in FIG. 7 are summarized in Table 6.

One method of evaluation of ET-based assays is to measure the time taken in each sample to reach a defined RFU value, i.e., to determine an intercept of each sample. Such a determination will indirectly reflect the intial slope of the curves. As shown in Table 6, however, selection of an appropriate RFU value is critical in this method of evaluation. Selecting RFU=2220 for the intercept yields results that are inconsistent with the expected effects on Δψ of the various treatments (i.e., CCCP>ionomycin>ionomycin & BKA>media only). Moreover, the RFU=2220 results are also somewhat confounding as the sample treated with ionomycin and BKA intercepts RFU=2220 twice. On the other hand, selecting a lower intercept value (RFU=160) yields results having the expected order. In the latter case, however, the protective effects of BKA might not be fully appreciated, as the result for ionomycin plus BKA (0.345) is only slightly different than that for ionomycin alone (0.400).

Another method of evaluation of ET-based assays is to directly determine the initial slope of the curve for each sample. However, as the results shown in FIG. 7 demonstrate, results from different samples can yield curves having similar initial slopes, even thought the overall shape of the curves and their endpoints are distinct.

Another method of evaluation is to sum the area under the curve of the plot, or to undertake some similar operation such as, e.g., adding the RFU values each time point, for each sample over a given time frame. As shown in Table 6, this method yields results for the four treatments that are consistent with the expected order of effect on Δψ (i.e., CCCP>ionomycin>ionomycin & BKA>media only). Thus, summing the area under each curve, or performing an operation that yields results that correspond to the area under the curves, is preferable in most instances, although other methods of evaluation may be used.

TABLE 6

Different Evaluations of the Results in FIG. 7

| Treatment (from expected most to least effect on Δψ) | Area Under Curve* | Ratio to media only Sample | Time$_{2220}$ Time (min.) to Reach RFU = 2220** | Ratio to media only Sample | Time$_{160}$ Time (min.) to Reach RFU = 160** | Ratio to media only Sample |
|---|---|---|---|---|---|---|
| CCCP | 16.2 × 10$^5$ | 10.1 | 0.85 | 0.133 | 0.050 | 0.083 |
| ionomycin | 6.79 × 10$^5$ | 4.22 | 0.55 | 0.086 | 0.200 | 0.333 |

TABLE 6-continued

Different Evaluations of the Results in FIG. 7

| Treatment | Area | | Time$_{2220}$ | | Time$_{160}$ | |
|---|---|---|---|---|---|---|
| (from expected most to least effect on Δψ) | Area Under Curve* | Ratio to media only Sample | Time (min.) to Reach RFU = 2220** | Ratio to media only Sample | Time (min.) to Reach RFU = 160** | Ratio to media only Sample |
| ionomycin and BKA | 2.37 × 10$^5$ | 1.47 | 1 = 0.75<br>2 = 1.85 | 1 = 0.117<br>2 = 0.711 | 0.255 | 0.425 |
| media only | 1.61 × 10$^5$ | 1.00 | 6.40 | 1.000 | 0.600 | 1.000 |

*Measured as sum of all readings over 0 to 460 seconds.
**Measured from moment when all 4 curves were coincident (t = 1.1 min.).

Example 5

FRET-Based Assay of Δψ

Figure 3A:
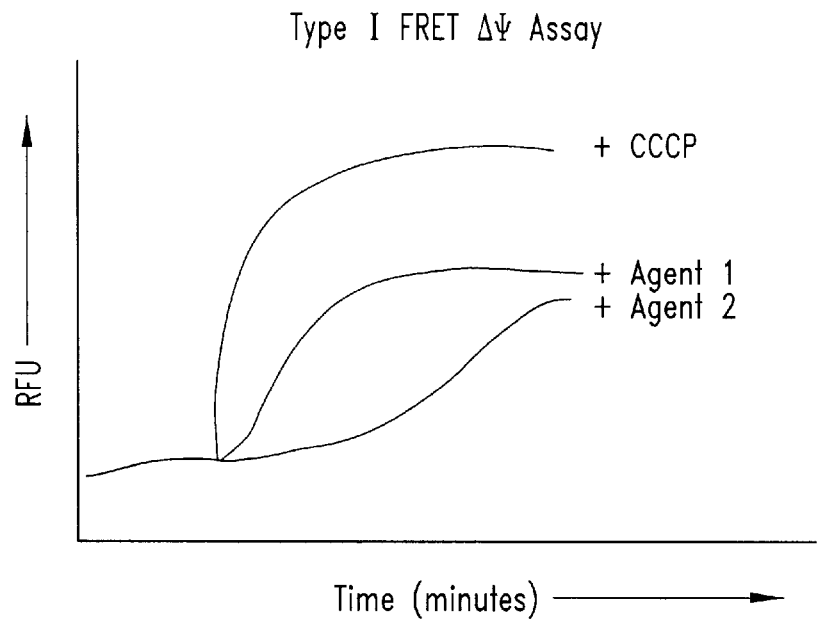
FIG. 3A, data from a Type I assay.

The preceding Example illustrates a potential limitation in the "Type I" FRET-based assay of Δψ, in which the effects of various agents on Δψ is compared to the effects of an agent (CCCP) that collapses Δψ (FIG. 3A). In order to yield more meaningful results, the "Type II" assay was developed. In the Type II assay, the agent(s) being tested is first added to a sample and, after allowing the agent(s) being tested some time to exert their effects, a Δψ collapsing agent is subsequently added to the same sample in order to drive Δψ to zero, thus establishing a baseline value for the results.

Figure 3B:
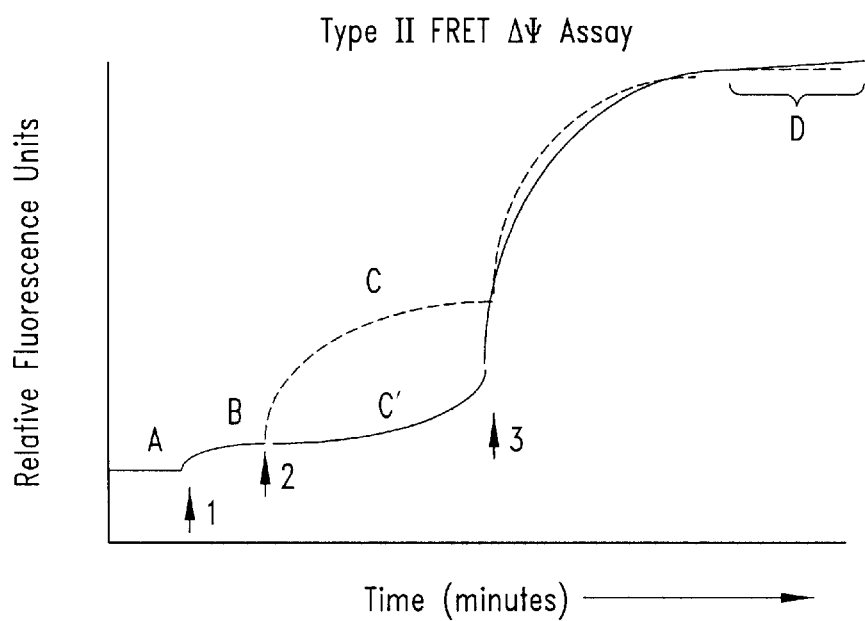
FIG. 3B, data from a Type II assay.

FIG. 3B shows a Type II assay. In one version of the Type II assay, wherein a compound is being tested for its ability to dissipate Δψ, the symbols in FIG. 3B are as follows. Optional initial readings ("A" or "B") that can be normalized to zero are first taken. The candidate Δψ-dissipating compound is added at timepoint "2." If the candidate Δψ-dissipating compound has little or no effect on Δψ, a signal like that represented by the solid line ("C'") is expected, whereas a test compound that dissipates Δψ results in a signal like that represented by the dashed line ("C"). At timepoint "3," an agent that completely collapses Δψ(such as, e.g., CCCP) is added, and a reading ("D") is taken after the collapse of Δψ is complete in order to allow for normalization for variations in cell density and efficiency of loading of the donor and acceptor compounds. The Δψ-dissipating activity of the test compound is calculated as the Δψ-Dissipating Value according to the formula:

Δψ–Dissipating Value=$(C-B)/(D-B)$ wherein a higher value for the Δψ-Dissipating Value indicates a greater Δψ-dissipating ability of the candidate compound.

In another version of the Type II assay, wherein a compound is being tested for its ability to inhibit or enhance the activity of an agent that dissipates Δψ, the symbols in FIG. 3B are as follows. An optional initial reading ("A") that can be normalized to zero is first taken. The test compound is added at timepoint "1," and a baseline measurement ("B") is taken. The Δψ-dissipating agent (e.g., ionomycin, atractyloside, etc.) is added at timepoint "2." If the test compound has little or no effect on the activity of the Δψ-dissipating agent, a signal like that represented by the dotted line ("C'") is expected, whereas a test compound that inhibits or protects against the activity of the Δψ-dissipating agent results in a signal like that represented by the solid line ("C"'). At timepoint "3," an agent that completely collapses Δψ (such as, e.g., CCCP) is added, and a reading ("D") is taken after the collapse of Δψ is complete in order to allow for normalization for variations in cell density and efficiency of loading of the donor and acceptor compounds. The activity of the test compound is calculated as the Efficacy Index according to the formula:

Efficacy Index=$(C-B)/(D-B)$ wherein a lower value for the Efficacy Index indicates a greater protective effect of the test compound.

Although CCCP and ionomycin are used in the following exemplary experiments, other Δψ collapsing agents are known and can be used. Such Δψ collapsing agents include, by way of example and not limitation, valinomycin, A23187 and 4-Br-A23187.

It is desirable to establish a dose-response curve for whatever Δψ collapsing agent is used, as conditions for the Type II are preferably such that Δψ collapses, and the measured signal reaches a plateau, in a rapid manner (i.e., preferably within 5 minutes after addition of the Δψ collapsing agent, more preferably within 3 minutes, and most preferably within 2 minutes). Another parameter that can be established from dose-response experiments is the optimal concentration of Δψ collapsing agent.

Figure 10:
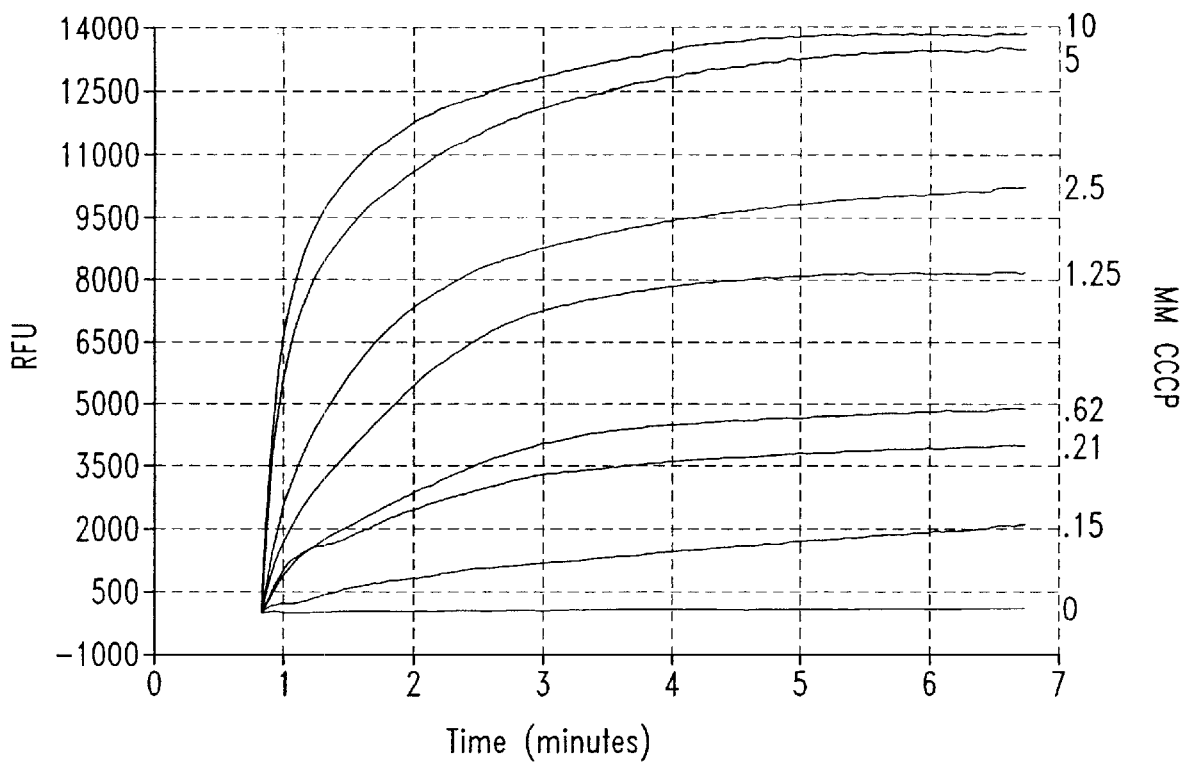
FIG. 10 is a dose-response curve for the $\Delta\psi_m$ collapsing agent CCCP.

A dose-response curve for CCCP is shown in FIG. 10. In the experiments performed to generate the data in this figure, SH-SY5Y cells were treated with 420 nM NAO and 5 uM TMRM according to the general procedure of Example 1 and then monitored for approximately 60 seconds before the indicated amount of CCCP was added. Dequenching of the emission signal from NAO was measured as in the preceding Examples. The dose-response curve reveals an increasingly rapid loss of NAO dequenching, as evidenced by the increasingly rapid rise in RFU, as higher concentrations of CCCP are used. These data also suggest that 10 uM is a near saturating concentration of CCCP to use, as the response to 10 uM CCCP is only slightly greater than that seen when 5 uM CCCP is applied (compare to the change in responses between 2.5 uM and 5 uM CCCP).

Figure 11:
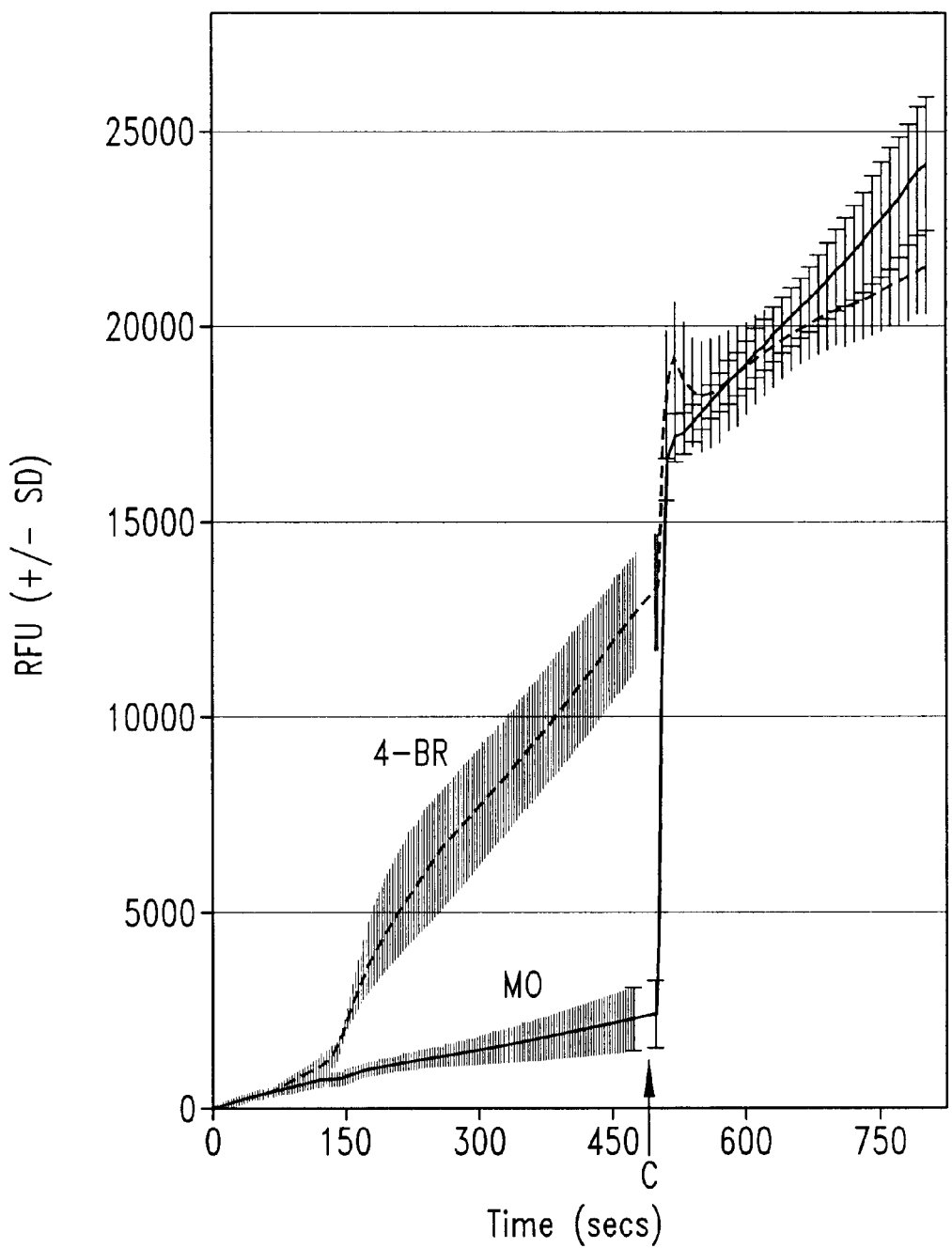
FIG. 11 shows Type II FRET $\Delta\psi_m$ assay. Symbols: "MO," results from samples treated with media (HBSS) only; "4BA;" results from samples treated with the $\Delta\psi_m$-dissipating agent 4-bromo-A23187; "C," and arrow indicate time of CCCP addition to samples.

The results from a representative Type II FRET experiment are shown in FIG. 11, which shows relative fluorescence units±standard errors for readings taken at the indicated timepoints. In this experiment, SH-SY5Y cells were contacted with NAO and TMRM according to the procedure of Example 1, placed in a FLIPR instrument. After about 2 minutes, half the samples were treated with prewarmed media alone and the other half were treated with prewarmed media comprising 5 μM of the Δψ-dissipating agent 4-bromo-A23187. About 6.5 minutes later, the Δψ-collapsing agent CCCP (final concentration, 5 μM) was added to all the samples and the fluorescence was read for an additional 7.5 minutes. As shown in FIG. 11, the cells treated with 4-bromo-A23187 ("4-BR") exhibited a gradual loss of $\Delta\psi$ up until the time CCCP was added, at which point $\Delta\psi$ further decreased and ultimately collapsed. As also shown in FIG. 11, the cells treated with media ("MO") also showed a rapid loss of $\Delta\psi$ following CCCP addition and approached complete $\Delta\psi$ collapse, the MO and 4-BR curves becoming asymptotic after about 600 seconds and for the remainder of the experiment.

Example 6

Dose Response Curves for $\Delta\psi$-Dissipating and $\Delta\psi$ Protective Agents Having established the basic parameters of the ET-based assay of $\Delta\psi$, more exact experiments were carried out to demonstrate that the assay can be used to generate dose-response curves for both $\Delta\psi$-dissipating and $\Delta\psi$-protective agents. SH-SY5Y cells were used in these experiments. The calcium ionophore ionomycin was used as a mock compound being evaluated for its capacity to cause dissipation of $\Delta\psi$, and cyclosporin A was used as a mock ionomycin-protective agent.

Figure 13:
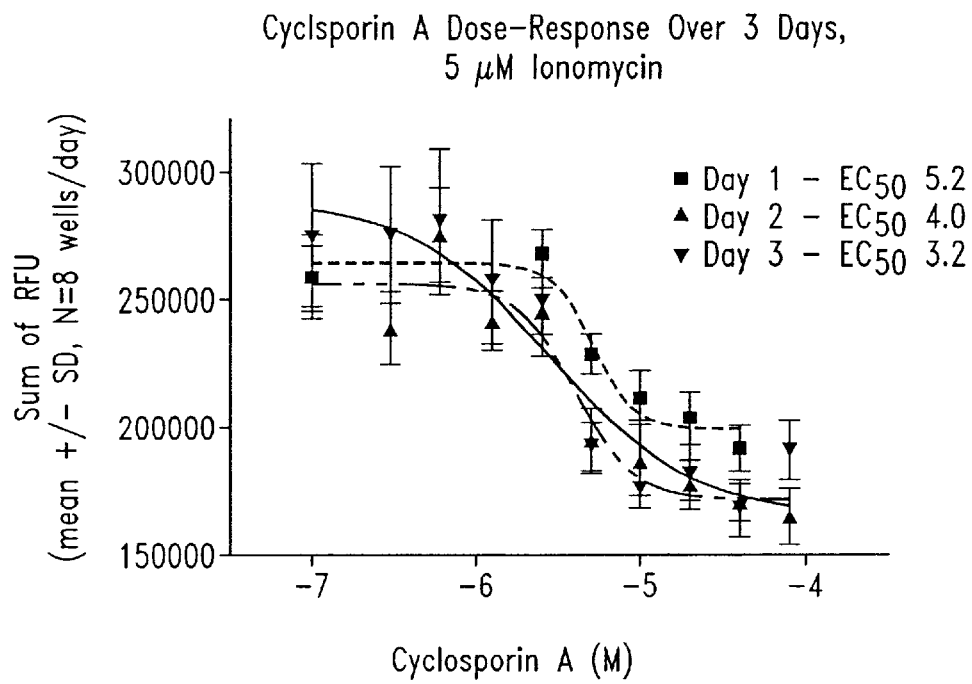
FIG. 13 is a dose response curve for a compound (cyclosporin A) that protects mitochondria against a $\Delta\psi$-dissipating compound (ionomycin).

Cells were grown to specific cell density and transferred to 96-well plates as described above. For both sets of experiments, TMRM and NAO were added at the concentrations and in the order and timing described in Example 1. For the experiments involving ionomycin alone, ionomycin was added at various concentrations 10 minutes after addition of NAO. In the case of the experiments designed to quantify the ability of cyclosporin A to protect against the effects of ionomycin, cells were loaded for 10 minutes with TMRM and for 5 minutes with NAO as described above for fluorophore loading, following which the cells were washed and exposed to various concentrations of cyclosporin A for 15 minutes prior to initiation of instrument readings. Readings numbered 1–21 were recorded at 3-second intervals, and thereafter readings numbered 22–196 were recorded at 5-second intervals. As shown in FIG. 13, he sum of the fluorescence signal over each time interval was determined and plotted against the $\log_{(10)}$ ionomycin concentration (M) to generate a cyclosporin A dose-response curve.

Figure 12:
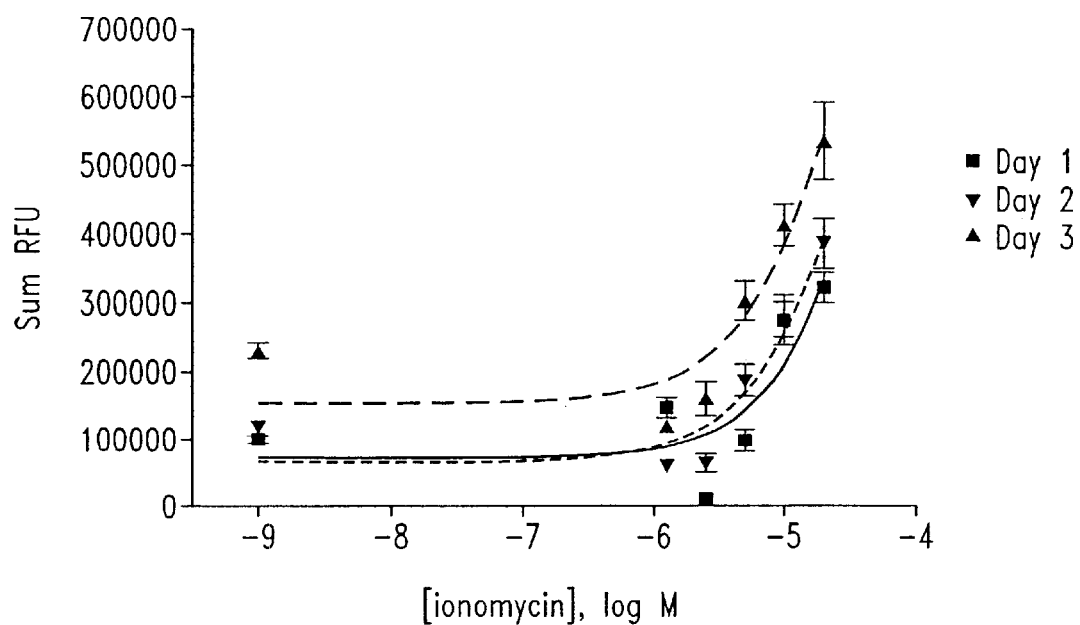
FIG. 12 is a dose response curve for a $\Delta\psi$-dissipating compound (ionomycin).

The dose response curves for cells exposed to ionomycin in three separate experiments (50,000 cells per well in each experiment) are shown in FIG. 12. The data generated parallel curves when plotted, demonstrating the reproducibility of the assay in analyzing compounds have a negative impact on $\Delta\psi$.

The dose response curves for cells pretreated with varying amounts of cyclosporin A and then exposed to ionomycin in three separate experiments (39,000 cells per well in each experiment) are shown in FIG. 13. The data generated similar curves when plotted, demonstrating the reproducibility of the assay in analyzing compounds that protect mitochondria from agents that have a negative impact on $\Delta\psi$.

Example 7

FRET in Various Cell Types

In the preceding examples, the FRET-based assay of $\Delta\psi$ was performed on a neuroblastoma cell line (SH-SY5Y) and the MixCon and 1685 cybrid cell lines. As mentioned previously, MixCon refers to a control cybrid cell line derived from several presumed normal donors (mixed), whereas the 1685 cybrid cell line has a mitochondrial component from a patient diagnosed as having Alzheimer's disease. Both cybrid cell lines have a common nuclear component derived from the SH-SY5Y neuroblastoma cell line.

Although the control (MixCon) and Alzheimer's (1685) cybrids show the same general response to various agents and treatments that influence $\Delta\psi$, some differences were detected by the FRET-based assay. For example, in one set of experiments, MixCon or 1685 cells (about 50,000 cells per well) were preincubated with 420 nM NAO and 5 uM TMRM according to the procedure of Example 1, after which A23187 (0 to 5 uM) was added. Loss of quenching of the NAO signal (i.e., fluorescence at 530±25 nm), reflecting was measured over time (4 minutes).

Figure 14:
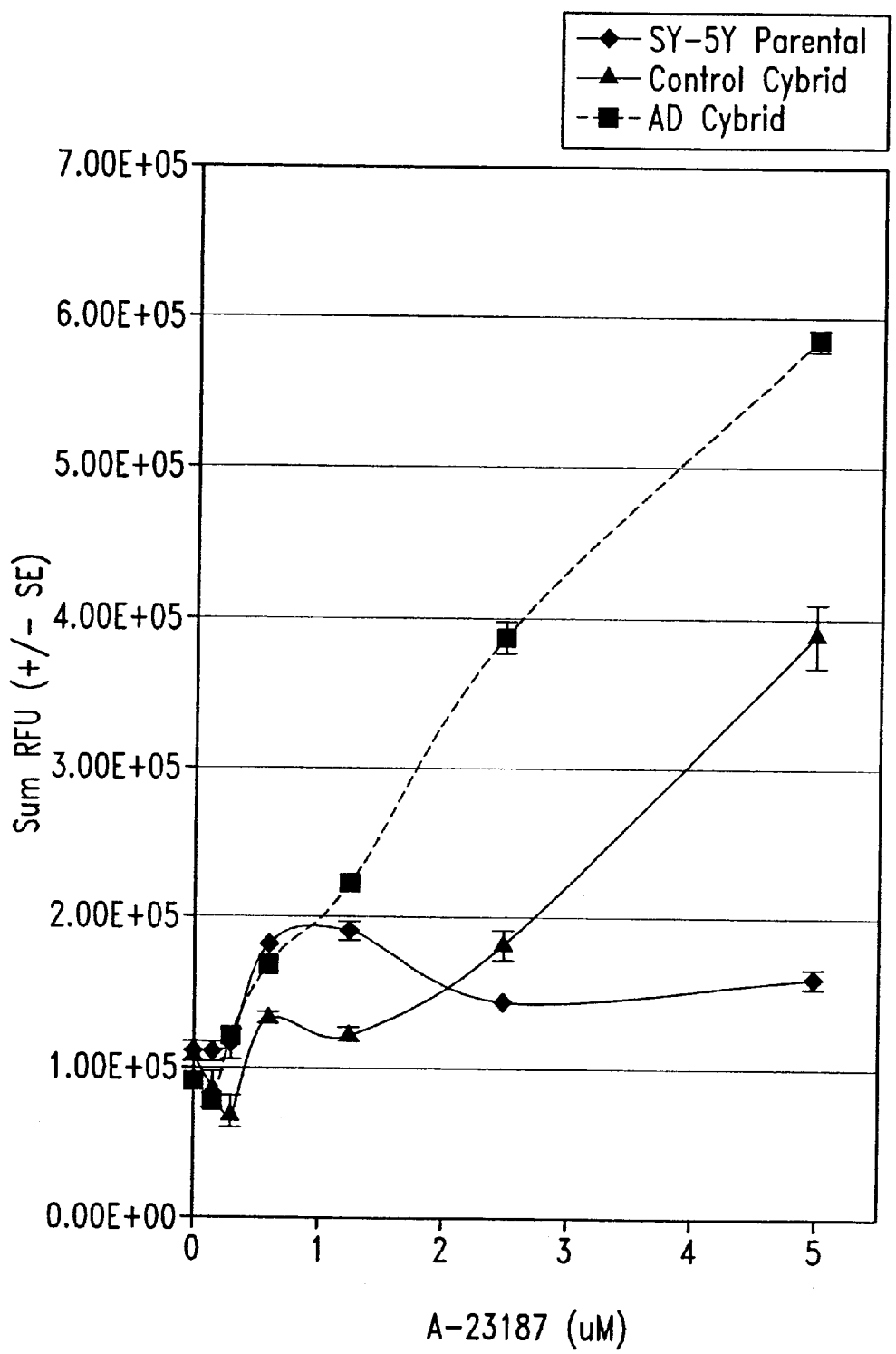
FIG. 14 shows a dose-response curve of three cell lines to the $\Delta\psi_m$-dissipating agent A-23187.

The results are expressed as sums of all the datapoints over the 4 minute windows for each concentration of A23187 (FIG. 14). These results reveal some differences in response between the SH-SY5Y parental cells and the 1685 and MixCon cybrids. The AD (1685) cybrids demonstrated the highest degree of sensitivity to A23187, and the control (MixCon) cybrids were somewhat more sensitive to A23187 than the parental SH-SY5Y cells. Statistical analysis (ANOVA) demonstrates that the increased susceptibility of the AD (1685) cybrid cells is significant. Thus, the ET-based assay of $\Delta\psi$ of the invention can be used to characterize mitochondrial abnormalities in whole cells. When such cells are isolated from an individual suspected of having or being predisposed to having a mitochondria-associated disease, the assay may be used to aid in the diagnosis of such diseases.

Example 8

ET-Based Assays for Detecting Specific Cell Types in a Sample

Assays utilizing energy transfer can be used to detect specific cell types in a biological sample. For example, rhodamine 123 (a Group II, III and IV acceptor compound; see Table 2) is taken up rapidly and retained for long periods (greater than 24 hours) by a variety of human carcinoma cells after washing, even though it is not usually well retained by other cell types when they are washed (Nadakavukaren et al., Cancer Res. 45:6093–6099, 1985; Summerhayes et al., Proc. Natl. Acad. U.S.A. 79:5292–5296, 1982; Christman et al., Gynecol. Oncol. 39:72–79, 1990).

An ET-based assay for carcinoma cells in a sample thus comprises the steps of (1) obtaining a biological sample from a patient, wherein the sample comprises cells; (2) contacting the cells in the sample with rhodamine 123; (3) optionally washing the cells; (4) contacting the cells with a mitochondrial donor compound from Group II, III or IV (Tables 2 and 3), such as NAO, MitoTracker® Green FM or MitoFluor™ Green; (5) exciting the sample with light having a wavelength within the excitation spectrum of the donor, and (6) detecting energy transfer as a quenching of the donor emission by rhodamine-123. Carcinoma cells retain rhodamine 123 and thus exhibit FRET with the donor compound.

The following experiment was carried out in order to demonstrate that certain cell types (in this Example, a human carcinoma cell line) differentially take up and retain particular ET donor and/or acceptor molecules as provided herein, and therefore have unique properties permitting such specific cell types to be detected by an ET-based assay of the present invention, thereby distinguishing such cell types from others that may be present. NCI-H460 is a human lung large cell carcinoma cell line (see Example 1 for details). NCI-H460 cells were added to 96-well plates (about 50,000 cells per well). In a Type II $\Delta\psi$ assay TMRM (5 µM) and NAO (420 nM) were added to the cells according to the procedure of Example 1. Ionomycin (50 µM) in media was also added to one set (n=24) of samples and media only was added to a control set of samples. The $\Delta\psi$ collapsing agent CCCP (5 µM) was added to all the samples about 9 minutes later. Fluorescence was measured using a FLIPR™ instrument during the experiment.

Figure 15:
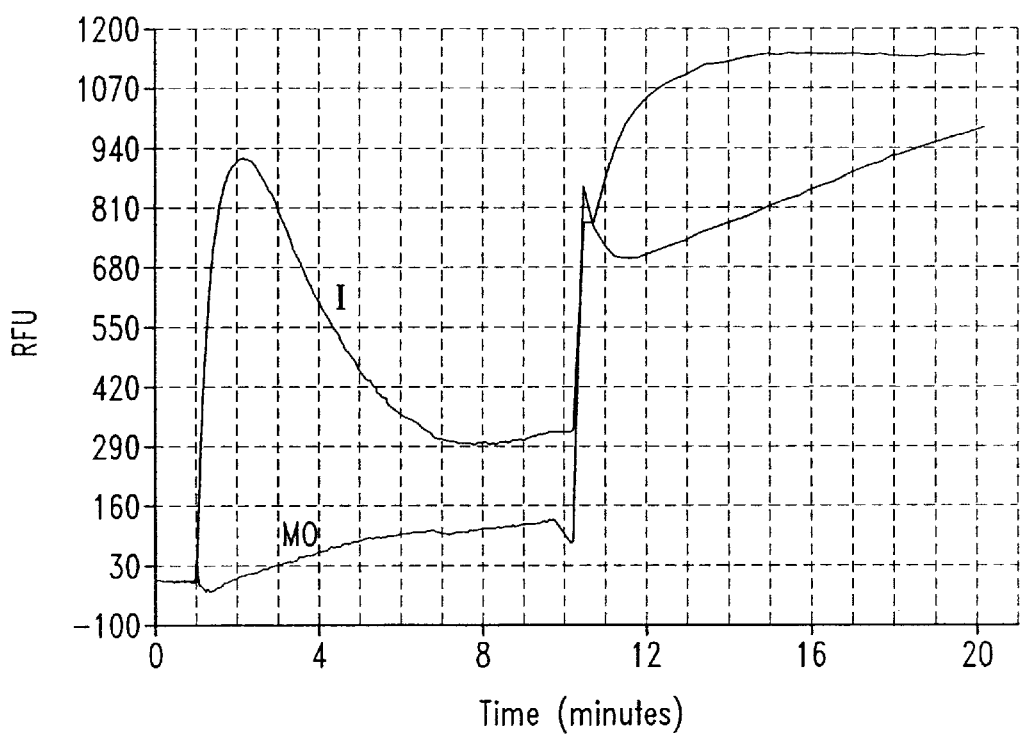
FIG. 15 shows representative data from FRET based assay of $\Delta\psi_m$.

The results are shown in FIG. 15. Although ionomycin caused a large degree of $\Delta\psi$ dissipation, the carcinoma cells recovered relatively rapidly by about 6 minutes after addition of ionomycin. This recovery is unlike that seen with the cybrid cell lines or the neuroblastoma SH-SY5Y cell line used in the preceding Examples and suggests that the mitochondria in the carcinoma cel line take up TMRM more rapidly, either in general or at least after a challenge to $\Delta\psi$, than do mitochondria from other cell types. It is particularly noteworthy that differential susceptibility to inducers of $\Delta\Psi$ collapse, as shown here by differential sensitivity to ionomycin detected in the FRET assay of mitochondrial membrane potential, can be used to distinguish cell types: The ionomycin concentration used here for NCI-H460 cells (50 µM), a concentration from which these cells recovered, is ten times the ionomycin concentration to which SH-SY5Y cells were sensitive, as indicated by their loss of mitochondrial membrane potential (FIG. 12). As described above, FIG. 12 depicts increased dequenching of NAO fluorescence at higher ionomycin conditions using SH-SY5Y cells, indicative of greater mitochondrial membrane potential collapse at the higher ionomycin concentrations, which effected the loss of TMRM from the mitochondrial compartment.

Example 9

Methods for Identifying Compounds for Treating Stroke

Mechanisms of cell death from ischemia and reperfusion involve both necrosis and delayed apoptosis, with mitochondrial dysfunction as a common antecedent to both. A number of events follow ischemia-induced loss of mitochondrial function, including decreased mitochondrial energy metabolism, increased mitochondrial production of toxic reactive oxygen species (ROS) after reperfusion, and active mitochondrial initiation of apoptotic cascades in conditions where energy production can be restored.

Following a neuronal ischemic event, mitochondrial ATP production halts due to the lack of oxygen. Although glycolytic ATP production can continue under anoxic conditions, glycolysis cannot meet the energy demands of neurons due to limited stores of glycolysis substrates in the brain. Still, lactate does accumulate in anoxic brain tissue, providing a measurable endpoint for biologic assays. Because of losses in aerobic competence, the tissue ATP concentration drops to negligible levels within minutes after cessation of oxygen flow to the brain.

Without adequate ATP, the ATP-dependent ion transporters fail, and the loss of ion homeostasis results in osmotic lysis and necrosis of neurons at the anoxic core of the infarct. De-energization also involves the loss of ATP-dependent transport processes that sequester glutamate. Massive influx of $Ca^{2+}$ and other ions ensues from activation of voltage-dependent and ligand-dependent ion channels (White et al., J. Neurosci. 15:1318–1328, 1995; Harrington et al., Neuron 16:219–228, 1996; Schinder et al., J. Neurosci. 16:6125–6133, 1996). Upon reperfusion, high levels of cytosolic $Ca^{2+}$ directly activate mitochondrial calcium uptake, preventing the establishment of normal mitochondrial function upon re-introduction of oxygen. Excessive $Ca^{2+}$ accumulation in the mitochondria can potentiate the production of oxygen- and carbon-centered radicals in neurons and lead to inactivation of mitochondrial electron transfer system (Dykens, J. Neurochem. 63:584–591, 1994; Reynolds et al, J. Neurosci. 15:3318–3327, 1995; Dugan et al., J. Neurosci. 15:6377–6388, 1995, Bindokas et al., J. Neurosci. 16:1324–1336, 1996).

Another consequence of mitochondrial $Ca^{2+}$ uptake is the induction of the membrane permeability transition (MPT), the opening of a nonspecific, voltage-sensitive, pore that dissipates $\Delta\Psi_m$. and allows solutes of <1,500 Daltons to equilibrate across the inner mitochondrial membrane (see reviews, Zoratti et al., Biochim Biophys. Acta 1241:139–176, 1995; Bernardi et al., J. Bioenerg. Biomemb. 26:509–517, 1994). High $\Delta\Psi_m$ that is normally generated by the electron transport chain in the absence of high $Ca^{2+}$ or free radical-induced injury, is a potent deterrent to MPT pore formation. Agents that moderate MPT and $\Delta\Psi_m$ collapse, such as Bcl-2 and cyclosporin A, correspondingly moderate glutamate excitotoxicity both in vitro and in vivo (Hoyt et al., Br. J. Pharmacol. 122:803–808, 1997; Niemninen et al., Neurosci. 75:993–997, 1996; Ankarcrona et al., FEBS Lett. 394:321–324, 1996; Uchino et al., Acta Physiol. Scand. 155:469–471, 1995; Li et al., Brain Res. 753:133–140, 1997).

Failure of cellular $Ca^{2+}$ efflux mechanisms and activation of phospholipases and proteases appear as late-stage events after ischemia and can lead to widespread damage to membranes and proteins. Cells exposed to less severe stress may initiate an apoptotic cascade. In this case, mitochondria may be reversibly damaged and release sufficient levels of apoptogenic factors to induce death while maintaining a residual capacity to generate ATP (MacManus et al., J. Cerebral Blood Flow Metab. 17:815–832, 1997). Therefore, healthy mitochondria play a bifunctional role in preservation of neuronal viability in ischemia/reperfusion injury: 1) by supplying ATP, mitochondria provide the driving force for glutamate re-uptake from the synaptic cleft and the ATP-dependent maintenance of normal membrane potential that further resists opening of voltage-sensitive ion channels, and 2) uninjured mitochondria resist the release of factors that can direct neurons down an apoptotic pathway. Maintaining mitochondrial integrity during ischemia/reperfusion and thereby defending against the ensuing wave of excitotoxicity thus permits identification of novel neuroprotective agents having utility for preventing stroke-related neuronal injury.
Primary Screening Assays Measurement of $\Delta\Psi_m$ provides a comprehensive indication of mitochondrial function and integrity. Therefore, the primary screening assay in stroke drug discovery utilizes the ET-based assay of $\Delta\Psi$ in whole cells in a high-throughput format. Agents and methods that maintain mitochondrial integrity during transient ischemia and the ensuing wave of excitotoxicity are expected to be effective neuroprotective agents with utility in limiting stroke-related neuronal injury. Given the limited therapeutic window for blockade of necrotic death at the core of an infarct, it is particularly desirable to develop therapeutic strategies to limit neuronal death by preventing mitochondrial dysfunction in the non-necrotic regions of an infarct. To this end, compounds are screened for their effects on $\Delta\Psi$ under control and $Ca^{2+}$ overload conditions.

Following a stroke, much of the injury to neurons in the penumbra is caused by excitotoxicity induced by glutamate released during cell lysis at the infarct focus. In order to more closely mimic in vivo biochemical and cellular events, primary screening assays are carried out in cells comprising one or more types of glutamate receptors (for reviews, see Gasis et al., *Curr. Opin. Neurobiol.* 1:20–26, 1991; Westbrook, *Curr. Opin. Neurobiol.* 4:337–346, 1994; and Lynch et al., *Curr. Opin. Neurobiol.* 7:510–516, 1994).

Glutamate receptors include ionotropic glutamate receptors (iGluRs) and metabotropic receptors (mGluRs). The iGluRs are glutamate-gated cation channels that are further classified further into the subclasses of NMDA receptors, AMPA receptors and kainate receptors. NMDA receptors are heteromeric complexes including, for example, NMDAR1/2A, NMDAR1/2B, NMDAR1/2C and NMDAR1/2D. AMPA receptors are homomeric complexes including, for example, GluR1, GluR2, GluR3 and GluR4. Kainate receptors may be either homomeric or heteromeric complexes of GluR5, GluR6, GluR7, KA-1 and KA-2. The mGluRs are 7-transmembrane G-protein coupled receptors that are also classified further into subclasses. Some mGluRs are phospholipase C-coupled mGluRs that increase cytosolic calcium; these include mGluR1 and mGluR5. Other mGluRs are adenylate cyclase-coupled mGluRs that decrease cytosolic cAMP; these include mGluR2, mGluR3, mGluR4, mGluR7, and mGluR8.

One example of a cell comprising one or more types of glutamate receptors that are used in primary screens is a primary cortical neuron expressing endogenous NMDA receptors. In these cells, application of extracellular glutamate elevates intracellular calcium levels (Stout et al., *Nat. Neurosci.* 1:366–373, 1998). Subsequent to glutamate addition, changes in $\Delta\Psi$ are measured using the ET-based assay of $\Delta\Psi$. Mitochondria-defective cybrid cells that have a depressed $\Delta\Psi$ (Cassarino et al., *Biochem. Biophys. Res. Commun.* 248:168–173, 1998) are also utilized in addition to primary neuronal cultures in order to provide a more extensive response to agents and/or conditions that are tested for their ability to dissipate or collapse $\Delta\Psi$.

Other examples of cells comprising one or more types of glutamate receptors that are used in primary screens include cells that have been genetically engineered to express or overexpress one or more glutamate receptors. A number of mammalian cell lines have been manipulated to stably express glutamate receptors in culture (for a review, see Varney et al., *Methods. Mol. Biol.* 128:43–59, 1999). Non-limiting examples of glutamate receptors that have been cloned and expressed in mammalian cells include NMDRA1A/2A and NMDAR1A/2B (Varney et al., *J. Pharmacol. Exp. Ther.* 279:367–378, 1996); NMDAR2C, isoforms 1, 2, 3 and 4 (Dagget et al., *J. Neurochem.* 71:1953–1968, 1998); GluR3 (Varney et al., *J. Pharmacol. Exp. Ther.* 285:358–370, 1998); and GluR1b and GluR5a (Lin et al., *Neuropharmacology* 36:917–931, 1997).

Secondary Screening Assays

Compounds that prevent the prolonged collapse of $\Delta\Psi_m$ caused by high $[Ca^{2+}_i]$ in the primary assay are evaluated further in secondary assays, including ROS production, measurement of cytochrome c release and caspase-3 activation as indicators of apoptosis, and cell viability. In this way, "hits" identified in the FRET $\Delta\Psi_m$ assay are further verified, and the mechanism by which the compound affects $\Delta\Psi_m$ can be better defined. The rationale for these assays is based on evidence suggesting that compounds that can maintain mitochondrial integrity under conditions of excitotoxicity or oxidative stress may correspondingly decrease the release of apoptogens and rescue penumbral neurons that are at risk of apoptotic death following transient ischemia.

The following assays are described in more detail in copending U.S. patent application Ser. No. 09/299,044, filed Apr. 23, 1999.

Assay for Inhibition of Production of Reactive Oxygen Species Using Dichlorofluorescin Diacetate: According to this assay, the ability of a mitochondria protecting agent of the invention to inhibit production of ROS intracellularly may be compared to its antioxidant activity in a cell-free environment. Production of ROS may be monitored using, for example by way of illustration and not limitation, 2',7'-dichlorodihydrofluorescein diacetate ("dichlorofluorescin diacetate" or DCFC), a sensitive indicator of the presence of oxidizing species. Non-fluorescent DCFC is converted upon oxidation to a fluorophore that can be quantified fluorimetrically. Cell membranes are also permeable to DCFC, but the charged acetate groups of DCFC are removed by intracellular esterase activity, rendering the indicator less able to diffuse back out of the cell.

In the cell-based aspect of the DCFC assay for inhibition of production of ROS, cultured cells may be pre-loaded with a suitable amount of DCFC and then contacted with a mitochondria protecting agent. After an appropriate interval, free radical production in the cultured cells may be induced by contacting them with iron (III)/ascorbate and the relative mean DCFC fluorescence can be monitored as a function of time.

In the cell-free aspect of the DCFC assay for inhibition of production of ROS, a mitochondria protecting agent may be tested for its ability to directly inhibit iron/ascorbate induced oxidation of DCFC when the protecting agent, the fluorescent indicator and the free radical former are all present in solution in the absence of cells.

Comparison of the properties of a mitochondria protecting agent in the cell-based and the cell-free aspects of the DCFC assay may permit determination of whether inhibition of ROS production by a mitochondria protecting agent proceeds stoichiometrically or catalytically. Without wishing to be bound by theory, mitochondria protecting agents that scavenge free radicals stoichiometrically (e.g., on a one-to-one molecular basis) may not represent preferred agents because high intracellular concentrations of such agents might be required for them to be effective in vivo. On the other hand, mitochondria protecting agents that act catalytically may moderate production of oxygen radicals at their source, or may block ROS production without the agents themselves being altered, or may alter the reactivity of ROS by an unknown mechanism. Such mitochondria protecting agents may "recycle" so that they can inhibit ROS at substoichiometric concentrations. Determination of this type of catalytic inhibition of ROS production by a mitochondria protecting agent in cells may indicate interaction of the agent with one or more cellular components that synergize with the agent to reduce or prevent ROS generation. A mitochondria protecting agent having such catalytic inhibitory characteristics may be a preferred agent for use according to the method of the invention.

Mitochondria protecting agents that are useful according to the instant invention may inhibit ROS production as quantified by this fluorescence assay or by other assays based on similar principles. The person having ordinary skill in the art is familiar with variations and modifications that may be made to the assay as described here without departing from the essence of this method for determining the effectiveness of a mitochondria protecting agent, and such variations and modifications are within the scope of this disclosure.

Assay for Mitochondrial Permeability Transition (MPT) Using 2-, 4-Dimethylaminostyryl-N-Methylpyridinium (DASPMI): According to this assay, one may determine the ability of a mitochondria protecting agent of the invention to inhibit the loss of mitochondrial membrane potential that accompanies mitochondrial dysfunction. As noted above, maintenance of a mitochondrial membrane potential may be compromised as a consequence of mitochondrial dysfunction. This loss of membrane potential or mitochondrial permeability transition (MPT) can be quantitatively measured using the mitochondria-selective fluorescent probe 2-,4-dimethylaminostyryl-N-methylpyridinium (DASPMI).

Upon introduction into cell cultures, DASPMI accumulates in mitochondria in a manner that is dependent on, and proportional to, mitochondrial membrane potential. If mitochondrial function is disrupted in such a manner as to compromise membrane potential, the fluorescent indicator compound leaks out of the membrane bounded organelle with a concomitant loss of detectable fluorescence. Fluorimetric measurement of the rate of decay of mitochondria associated DASPMI fluorescence provides a quantitative measure of loss of membrane potential, or MPT. Because mitochondrial dysfunction may be the result of reactive free radicals such as ROS, mitochondria protecting agents that retard the rate of loss of DASPMI fluorescence may be effective agents for treating mitochondria associated diseases according to the methods of the instant invention.

Assays of Apoptosis in Cells Treated with Mitochondria Protecting Agents: As noted above, mitochondrial dysfunction may be an induction signal for cellular apoptosis. According to the assays in this section, one may determine the ability of a rnitochondria protecting agent of the invention to inhibit or delay the onset of apoptosis. Mitochondrial dysfunction may be present in cells known or suspected of being derived from a subject with a mitochondria associated disease, or mitochondrial dysfunction may be induced in cultured normal or diseases cells by one or more of a variety of physical (e.g., UV radiation), physiological and biochemical stimuli with which those having skill in the art will be familiar.

Apoptosis and/or biochemical processes associated with apoptosis may also be using one or more "apoptogens," i.e., agents that induce apoptosis and/or associated processes when contacted with or withdrawn from cells or isolated mitochondria. Such apoptogens include by way of illustration and not limitation (1) apoptogens that are added to cells having specific receptors therefor, e.g., tumor necrosis factor (TNF), FasL, glutamate and NMDA; (2) withdrawal of growth factors from cells having specific receptors for such factors, such factors including, for example, IL-3 or corticosterone; and apoptogens that may be added to cells but which do not require a specific receptor, including (3) Herbimycin A (Mancini et al., *J. Cell. Biol.* 138:449–469, 1997), (4) Paraquat (Costantini et al., *Toxicology* 99:1–2, 1995); (5) ethylene glycols (http://www.ulaval.ca/vrr/rech/Proj/532866.html); (6) protein kinase inhibitors, such as, e.g.: Staurosporine, Calphostin C, d-erythro-sphingosine derivatives, Chelerythrine chloride, Genistein, 1-(5-isoquinolinesulfonyl)-2-methylpiperazine, KN-93, Quercitin, N-[2-((p-bromocinnamyl)amino)ethyl]-5-5-isoquinolinesulfonamide and caffeic acid phenethyl ester; (7) ionophores such as, e.g.: lonomycin and valinomycin; (8) MAP kinase inducers such as, e.g.: Anisomycin and Anandamine; (9) cell cycle blockers such as, e.g.: Aphidicolin, Colcemid, 5-fluorouracil and homoharringtonine; (10) Acetylcholinesterase inhibitors such as, e.g.: berberine; (11) anti-estrogens such as, e.g.: Tamoxifen; (12) pro-oxidants, such as, e.g., tert-butyl peroxide and hydrogen peroxide; (13) free radicals such as, e.g., nitric oxide; (14) inorganic metal ions, such as, e.g.: cadmium; (15) DNA synthesis inhibitors such as, for example, Actinomycin D, Bleomycin sulfate, Hydroxyurea, Methotrexate, Mitomycin C, Camptothecin, daunorubicin and intercalators such as, e.g., doxorubicin; (16) protein synthesis inhibitors such as, e.g., cyclohexamide, puromycin and rapamycin; (17) agents that affect microtubulin formation or stability such as, e.g., Vinblastine, Vincristine, colchicine, 4-hydroxyphenylretinainde and paclitaxel; (18) agents that raise intracellular calcium levels by causing the release thereof from intracellular stores, such as, e.g., thapsigargin (Thastrup et al., *Proc. Natl. Acad. Sci. U.S.A.* 87:2466–2470, 1990), thpasigargicin (Santarius et al., *Toxicon* 25:389–399, 1987) and excitatory amino acids and their derivatives such as, e.g., kainate, N-methyl-D-aspartic acid (NMDA), N-acetylaspartylglutamate (NAAG, a glutamate derivative), 2-amino-3-(3-hydroxy-5-methylisoxazol-4-yl)propionic acid (AMPA) and 2-amino-3-(3-hydroxy-5-phenylisoxazol-4-yl)propionic acid (APPA, an AMPA derivative); and agents that are added to isolated mitochondria, such as (19) MPT inducers, e.g., Bax protein (Jurgenmeier et al., *Proc. Natl. Acad. Sci. U.S.A.* 95:4997–5002, 1998); and (20) calcium and inorganic phosphate (Kroemer et al., *Ann. Rev. Physiol.* 60:619–642, 1998).

In one aspect of the apoptosis assays, cells that are suspected of undergoing apoptosis may be examined for morphological, permeability or other changes that are indicative of an apoptotic state. For example by way of illustration and not limitation, apoptosis in many cell types may cause altered morphological appearance such as plasma membrane blebbing, cell shape change, loss of substrate adhesion properties or other morphological changes that can be readily detected by those skilled in the art using light microscopy. As another example, cells undergoing apoptosis may exhibit fragmentation and disintegration of chromosomes, which may be apparent by microscopy and/or through the use of DNA specific or chromatin specific dyes that are known in the art, including fluorescent dyes. Such cells may also exhibit altered membrane permeability properties as may be readily detected through the use of vital dyes (e.g., propidium iodide, trypan blue) or the detection of lactate dehydrogenase leakage into the extracellular milieu. Damage to DNA may also be assayed using electrophoretic techniques (see, for example, Morris et al., *BioTechniques* 26:282–289, 1999). These and other means for detecting apoptotic cells by morphologic, permeability and related changes will be apparent to those familiar with the art.

In another aspect of the apoptosis assays, translocation of cell membrane phosphatidylserine (PS) from the inner to the outer leaflet of the plasma membrane is quantified by measuring outer leaflet binding by the PS-specific protein annexin (Martin et al, *J. Exp. Med.* 182:1545–1556, 1995; Fadok et al., *J. Immunol.* 148:2207–2216, 1992.). In a perferred format, exteriorization of plasma membrane PS is assessed in 96-well plates using a labeled annexin derivative such as an annexin-fluorescein isothiocyanate conjugate (annexin-FITC, Oncogene Research Products, Cambridge, Mass.).

In another aspect of the apoptosis assays, quantification of the mitochondrial protein cytochrome c that has leaked out of mitochondria in apoptotic cells may provide an apoptosis indicator that can be readily determined (Liu et al., *Cell* 86:147–157, 1996). Such quantification of cytochrome c may be performed spectrophotometrically, immunochemically or by other well established methods for detecting the presence of a specific protein. Release of cytochrome c from mitochondria in cells challenged with apoptotic stimuli (e.g., ionomycin, a well known calcium ionophore) can be followed by a variety of immunological methods. Matrix-assisted laser desorption ionization time of flight mass MALDI-TOF) spectrometry coupled with affinity capture is particularly suitable for such analysis since apo-cytochrome c and holo cytochrome c can be distinguished on the basis of their unique molecular weights. For example, the SELDI system (Ciphergen, Palo Alto, USA) may be utilized to follow the inhibition by mitochondria protecting agents of cytochrome c release from mitochondria in ionomycin treated cells. In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular weight of the protein is determined by its time of flight to the detector of the SELDI mass spectrometer.

In another aspect of the apoptosis assays, induction of specific protease activity in a family of apoptosis-activated proteases known as the caspases (Thornberry and Lazebnik, *Science* 281:1312–1316, 1998) is measured, for example by determination of caspase-mediated cleavage of specifically recognized protein substrates. These substrates may include, for example, poly-(ADP-ribose) polymerase (PARP) or other naturally occurring or synthetic peptides and proteins cleaved by caspases that are known in the art (see, e.g., Ellerby et al., *J. Neurosci.* 17:6165–6178, 1997). The labeled synthetic peptide Z-Tyr-Val-Ala-Asp-AFC, wherein "Z" indicates a benzoyl carbonyl moiety and AFC indicates 7-amino-4-trifluoromethylcoumarin (Kluck et al., 1997 *Science* 275:1132–1136, 1997; Nicholson et al., *Nature* 376:37–43, 1995), is one such substrate. Another labeled synthetic peptide substrate for caspase-3 consists of two fluorescent proteins linked to each other via a peptide linker comprising the recognition/cleavage site for the protease (Xu et al., *Nucleic Acids Res.* 26:2034–2035, 1998). Other substrates include nuclear proteins such as U1-70 kDa and DNA-PKcs (Rosen and Casciola-Rosen, *J. Cell. Biochem.* 64:50–454, 1997; Cohen, *Biochem. J.* 326:1–16, 1997).

In another aspect of the apoptosis assays, the ratio of living to dead cells, or the proportion of dead cells, in a population of cells exposed to an apoptogen is determined as a measure of the ultimate consequence of apoptosis. Living cells can be distinguished from dead cells using any of a number of techniques known to those skilled in the art. By way of non-limiting example, vital dyes such as propidium iodide or trypan blue may be used to determine the proportion of dead cells in a population of cells that have been treated with an apoptogen and a compound according to the invention.

The person of ordinary skill in the art will readily appreciate that there may be other suitable techniques for quantifying apoptosis, and such techniques for purposes of determining the effects of mitochondria protecting agents on the induction and kinetics of apoptosis are within the scope of the assays disclosed here.

Assay of Electron Transport Chain (ETC) Activity in Isolated Mitochondria: As described above, mitochondria associated diseases may be characterized by impaired mitochondrial respiratory activity that may be the direct or indirect consequence of elevated levels of reactive free radicals such as ROS. Accordingly, a mitochondria protecting agent for use in the methods provided by the instant invention may restore or prevent further deterioration of ETC activity in mitochondria of individuals having mitochondria associated diseases. Assay methods for monitoring the enzymatic activities of mitochondrial ETC Complexes I, II, III, IV and ATP synthetase, and for monitoring oxygen consumption by mitochondria, are well known in the art. (See, e.g., Parker et al., *Neurology* 44:1090–1096, 1994; Miller et al, *J. Neurochem.* 67:1897–1907 1996.) It is within the scope of the methods provided by the instant invention to identify a mitochondria protecting agent using such assays of mitochondrial function.

Furthermore, mitochondrial function may be monitored by measuring the oxidation state of mitochondrial cytochrome c at 540 nm. As described above, oxidative damage that may arise in mitochondria associated diseases may include damage to mitochondrial components such that cytochrome c oxidation state, by itself or in concert with other parameters of mitochondrial function including but not limited to mitochondrial oxygen consumption, may be an indicator of reactive free radical damage to mitochondrial components. Accordingly, the invention provides various assays designed to test the inhibition of such oxidative damage by mitochondria protecting agents. The various forms such assays may take will be appreciated by those familiar with the art and is not intended to be limited by the disclosures herein, including in the Examples.

For example by way of illustration and not limitation, Complex IV activity may be determined using commercially available cytochrome c that is fully reduced via exposure to excess ascorbate. Cytochrome c oxidation may then be monitored spectrophotometrically at 540 nm using a stirred cuvette in which the ambient oxygen above the buffer is replaced with argon. Oxygen reduction in the cuvette may be concurrently monitored using a micro oxygen electrode with which those skilled in the art will be familiar, where such an electrode may be inserted into the cuvette in a manner that preserves the argon atmosphere of the sample, for example through a sealed rubber stopper. The reaction may be initiated by addition of a cell homogenate or, preferably a preparation of isolated mitochondria, via injection through the rubber stopper. This assay, or others based on similar principles, may permit correlation of mitochondrial respiratory activity with structural features of one or more mitochondrial components. In the assay described here, for example, a defect in complex IV activity may be correlated with an enzyme recognition site.

Tertiary Screening Assays

Compounds that possess the desired activity profile in secondary in vitro assays are tested for in vivo efficacy in the rodent middle cerebral artery occlusion (MCAO) model of transient focal ischemia that is reported to produce ischemia analogous to MCAO branch occlusion in humans (Longa et al., *Stroke* 1:84–91, 1989). Initially, test compounds are administered by a continuous intravenous infusion before and during the ischemia/reperfusion period to ensure the greatest chance for experimental success. Once efficacy is established, experiments are conducted in which efficacy is assessed as a post-treatment using single and multiple drug administration regimens. The efficacy of the test compounds is directly assessed by measuring the reduction of neuronal loss in the infarcted brain region using techniques such as magnetic resonance imaging. Other additional endpoints are then measured, including reduction of brain lactate production as a consequence of the switch from aerobic to anaerobic metabolism after oxygen deprivation, reduction in DNA, protein and lipid oxidation products.

Example 10

ET-Based Assays for Monitoring Fusion of Subcellular Compartments

Assays utilizing energy transfer can be used to monitor the fusion of subcellular compartments such as, e.g., organelles. For example, mitochondria undergo changes, including fission and fusion, and the latter process involves apparently coordinated rearrangements of internal elements (i.e., the inner membrane, cristae, etc.) (for a review, see Bereiter-Hahn and Voth, *Microscopy Research and Technique* 27:198–219, 1994). Such changes are believed to be important for various developmental processes. In a variety of organisms including yeast such as *C. cerevisiae*, insects such as *D. melanogaster*, invertebrates such as *C. elegans*, and mammals such as *H. sapiens*, fusion of mitochondria is mediated by GTPase proteins generally known as "mitofusins" (see Hales et al., *Cell* 90:121–129, 1997; Hermann et al., *J. Cell. Biol.* 143:359–373, 1998; and published PCT patent application WO 98/55618). Mutations in the fuzzy onions (fzo) gene, which encodes a mitofusin in *D. melanogaster*, impair spermatogenesis and renders male insects sterile (Hales et al., *Cell* 90:121–129, 1997).

Accordingly, in certain embodiments the present invention provides a method of identifying an agent that alters (i.e., increases or decreases) the fusion of mitochondria by assaying, in the absence and presence of a candidate agent, a mitochondrial fusion event. Such an agent is identified by contacting a first sample comprising one or more mitochondria with an ET donor molecule and a second sample comprising one or more mitochondria with an ET acceptor molecule, contacting the first and second samples with one another in the absence and presence of a candidate agent under conditions and for a time sufficient to permit mitochondrial fusion, exciting the ET donor to produce an excited ET donor molecule, detecting a signal generated by energy transfer from the ET donor to the ET acceptor and comparing the signal generated in the absence of the candidate agent to the signal generated in the presence of the candidate agent.

In those certain preferred embodiments wherein the invention is directed to a method for identifying an agent that alters mitochondrial fusion, neither the ET donor molecule nor the ET acceptor molecule is endogenous to mitochondria, and the ET donor and the ET acceptor each localize independently of one another to the same submitochondrial site or to acceptably adjacent submitochondrial sites as provided herein. Typically, based upon the teachings provided herein, a person having ordinary skill in the art can readily determine when a candidate agent alters mitochondrial fusion, for example, by detecting a statistically significant change in the ET signal generated in the presence of the agent relative to the ET signal generated in the absence of the agent. As noted above, conditions permissive for mitochondrial fusion events are known in the art, such that those having ordinary skill in the art can readily determine what are suitable conditions for conducting the instant assay method without undue experimentation. By way of illustration and not limitation, such conditions may include those that permit fusion of isolated mitochondria, which refers to mitochondria that have been removed from the milieu in which they occur naturally; such conditions may also include those that permit at least one sample population of mitochondrial to undergo fusion within cells.

It is desirable to develop novel antibiotics or pesticides that function by selectively inhibiting mitofusin activity in undesirable insects or eukaryotic parasites but have minimal or no effect on the mitofusin of desirable insects or plants or on mammalian hosts including humans. It is also desirable to identify and characterize agents that stimulate or inhibit intracellular mitochondrial fusion events for the treatment of human diseases. The present invention can be used to achieve these goals in the following manner.

In general, a first group of mitochondria is preincubated with a donor compound, and a second group of mitochondria is incubated with an appropriate acceptor compound. Coincubation of the first and second group of mitochondria will result in fusion of individual mitochondria from each set, in which case the donor and acceptor compounds will achieve proximity to each other. Thus, mitochondrial fusion will lead to energy transfer that can be measured according to the present disclosure. If an agent that stimulates or inhibits mitochondrial fusion is also added to these reactions, the degree of energy transfer and/or the rate at which energy transfer occurs will increase or decrease, respectively. Candidate agents having an effect on the activity or level of expression of mitofusin proteins can thus be screened for and characterized via an ET-based assay.

Example 11

ET-Based Assays for Monitoring Localization of Agents to Specific Subcellular Sites Assays utilizing energy transfer can be used to monitor the influx or efflux of agents into a specific subcellular compartment within isolated oragnelles or intact cells; in the latter case, such assays can be used to estimate pharmacokinetic properties of candidate therapeutic agents. For example, agents comprising tertramethylrhodamine (TMR) or related moieties have been described. For example, oligonucleotides that are 5'-end labeled with TMR are available from Genomyx Corp. (Foster City, Calif.), and dideoxynucleotides conjugated to rhodamine or dichlororhodamine moieties are available from the Perkin-Elmer Corp. (Norwalk, Conn.). General methods for preparing conjugates comprising NAO- or JC-1-based moieties are described in published PCT patent application WO 98/17826. Mitochondrial uptake of such agents can be evaluated using the present invention as follows.

The uptake of agents comprising tertramethylrhodamine (TMR) or related moieties into mitochondria can be monitored by preincubating mitochondria or cells containing mitochondria with a donor compound such as NAO, MitoTracker® Green FM or MitoFluor™ Green for a period of time, after which the TMR-conjugated agent of interest is added. If the agent is taken up by mitochondria, the TMR or TMR-like portion thereof will act as an acceptor for energy emitted from the donor compound. Uptake of the agent can thus be followed as a function of either decreasing emission from the donor or increasing emission from the TMR or TMR-like moiety.

Similarly, the uptake of agents comprising NAO or NAO-like moieties into mitochondria can be monitored by preincubating mitochondria or cells containing mitochondria with an acceptor compound such as TMRM, TMRE or rhodamine 123 for a period of time, after which the NAO-conjugated agent of interest is added. If the agent is taken up by mitochondria, the NAO or NAO-like portion thereof will act as a donor for energy emitted from the acceptor. Uptake of the agent can thus be followed as a function of either increasing emission from the acceptor compound or decreasing emission from the NAO or NAO-like moiety. Uptake of agents comprising JC-1-based moieties are monitored in like fashion, except that donor or acceptor compounds appropriate for JC-1 and mitochondria (see Tables 2 and 3) are used.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for assaying mitochondrial membrane potential, comprising the steps of:
   (a) contacting a sample comprising one or more mitochondria, simultaneously or sequentially and in either order, with each of a first and a second energy transfer molecule that is not endogenous to the mitochondria, wherein:
      (i) the first and second energy transfer molecules each localize independently of one another to the same submitochondrial site or to acceptably adjacent submitochondrial sites, the sites being selected from the group consisting of mitochondrial outer membrane, mitochondrial inner membrane, mitochondrial intermembrane space and mitochondrial matrix, and
      (ii) said first energy transfer molecule is an energy donor molecule and said second energy transfer molecule is an energy acceptor molecule;
   (b) exciting said energy donor molecule to produce an excited energy donor molecule; and
   (c) detecting a signal generated by energy transfer from said first energy transfer molecule to said second energy transfer molecule, wherein the concentration of at least one of said energy transfer molecules in the mitochondria changes as a function of membrane potential.

2. The method of claim 1 wherein the excited energy donor molecule transfers energy to the energy acceptor molecule to produce an excited energy acceptor molecule, and the signal detected in step (c) results from energy released by the excited energy acceptor molecule.

3. The method of claim 1 wherein energy transfer from the first energy transfer molecule to the second energy transfer molecule results in a decrease in the detectable signal.

4. The method of claim 1, further comprising contacting the mitochondria with an agent that induces dissipation of mitochondrial membrane potential.

5. The method of claim 4 wherein the agent that induces dissipation of mitochondrial membrane potential is an ionophore.

6. The method of either claim 1 or claim 4, further comprising contacting the mitochondria with an agent that induces collapse of mitochondrial membrane potential.

7. The method of claim 6, wherein the agent that induces collapse of mitochondrial membrane potential is selected from the group consisting of CCCP and FCCP.

8. The method of claim 1 wherein the sample is washed prior to the step of detecting a signal.

9. The method of claim 1 wherein the signal detected in step (c) is compared with a reference signal.

10. The method of claim 9 wherein the reference signal is generated by an indicator selected from the group consisting of an indicator of cell number, an indicator of mitochondrial mass, an indicator of cellular protein, an indicator of cellular DNA, an indicator of mitochondrial DNA, an indicator of mitochondrial protein and an indicator of fluid volume.

11. The method of claim 1 wherein the sample comprises one or more mitochondria that are present within at least one cell, and wherein the signal detected in step (c) is compared with a reference signal.

12. The method of claim 11 wherein the reference signal is generated from a subcellular site selected from the group consisting of mitochondrial outer membrane, mitochondrial inner membrane, mitochondrial intermembrane space, mitochondrial matrix, cytoplasm, nucleus, nuclear membrane and plasma membrane.

13. The method of claim 11 wherein the reference signal is generated from extracellular medium.

14. The method of claim 1 wherein mitochondria are present within at least one cell during at least one step.

15. The method of claim 14 wherein the cell is an organism.

16. The method of claim 14 wherein the cell is a cultured cell.

17. The method of claim 14 wherein the cell is a cybrid cell.

18. The method of claim 14, wherein the cell is a plant cell.

19. The method of claim 14 wherein the cell is an animal cell.

20. The method of claim 14 wherein the cell is present in a biological sample derived from a multicellular organism.

21. The method of claim 20 wherein the cell is a plant cell.

22. The method of claim 20, wherein the cell is an animal cell.

23. The method of claim 22, wherein the animal is a mammal.

24. The method of claim 23, wherein the mammal is a human.

25. The method of claim 24, wherein said human has, is suspected of having or is at risk of having a disease or disorder associated with organellar dysfunction.

26. The method of claim 25 wherein the organellar dysfunction is mitochondrial dysfunction.

27. The method of claim 25 wherein the organellar dysfunction is lysosomal dysfunction.

28. The method of claim 1 wherein the first energy transfer molecule localizes to a submitochondrial site selected from the group consisting of mitochondrial matrix and mitochondrial inner membrane and the second energy transfer molecule localizes to a submitochondrial site selected from the group consisting of mitochondrial matrix and mitochondrial inner membrane.

29. The method of claim 28 wherein the concentration of the first energy transfer molecule in the submitochondrial site does not change as a function of membrane potential, and the concentration of the second energy transfer molecule in the mitochondrial matrix decreases as a function of membrane potential.

30. The method of claim 29 wherein
   (a) the first energy transfer molecule has an excitation maximum at a wavelength of from about 373 nm to about 390 nm, and an emission maximum at a wavelength of from about 400 nm to about 500 nm; and
   (b) the second energy transfer molecule has an excitation maximum at a wavelength of from about 400 nm to about 500 nm.

31. The method of claim 30 wherein
   (i) the first energy transfer molecule is a fusion protein, wherein said fusion protein comprises (a) a blue-shifted green fluorescent protein polypeptide having a mutation in at least one of Phe-64, Ser-65, Tyr-66, Val-68 and Tyr-145, and (b) a polypeptide sequence that localizes said fusion protein to a submitochondrial site selected from the group consisting of mitochondrial matrix and mitochondrial inner membrane; and
   (ii) the second energy transfer molecule is selected from the group consisting of DASPEI, DASPMI, 4-Di-1-ASP, 2-Di-1-ASP, $DiOC_7(3)$, $DiOC_6(3)$, JC-1 and SYTO® 18 yeast mitochondrial stain.

32. The method of claim 29 wherein
   (a) the first energy transfer molecule has an excitation maximum at a wavelength of from about 425 nm to about 440 nm, and an emission maximum at a wavelength of from about 450 nm to about 535 nm; and (b) the second energy transfer molecule has an excitation maximum at a wavelength of from about 450 nm to about 530 nm.

33. The method of claim 32 wherein
(i) said first energy transfer molecule is a fusion protein, wherein said fusion protein comprises (a) a cyan-shifted Green Fluorescent Protein polypeptide having a mutation in at least one of Phe-64, Ser-65, Tyr-66, Asn-146, Met-153, Val-163 and Asn-212, and (b) a polypeptide sequence that localizes said fusion protein to a submitochondrial site selected from the group consisting of mitochondrial matrix and mitochondrial inner membrane; and
(ii) the second energy transfer molecule is selected from the group consisting of DASPEI, 2-Di-1-ASP, $DiOC_6$(3), SYTO® 18 yeast mitochondrial stain, rhodamine 6G, JC-1, NBD C6-ceramide and NBD C6-sphingomyelin.

34. The method of claim 29 wherein
(a) said first energy transfer molecule has an excitation maximum at a wavelength of from about 470 nm to about 500 nm, and an emission maximum at a wavelength of from about 505 nm to about 565 nm; and
(b) said second energy transfer molecule has an excitation maximum at a wavelength of from about 505 nm to about 565 nm.

35. The method of claim 34 wherein
(i) said first energy transfer molecule is selected from the group consisting of nonylacridine orange, MitoTracker® Green FM, MitoFluor™ Green, and a fusion protein, wherein said fusion protein comprises (a) a Green Fluorescent Protein polypeptide selected from the group consisting of a wildtype Green Fluorescent Protein polypeptide, a red-shifted Green Fluorescent Protein polypeptide having a mutation in one or more of Phe-64, Ser-65, Tyr-66, Gln-69, Ser-72 and Thr-203 and a yellow-shifted Green Fluorescent Protein polypeptide having a mutation in one or more of Phe-64, Ser-65, Tyr-66, Gln-69, Ser-72 and Thr-203, and (b) a polypeptide sequence that localizes said fusion protein to a submitochondrial site selected from the group consisting of mitochondrial matrix and mitochondrial inner membrane; and
(ii) said second energy transfer molecule is selected from the group consisting of rhodamine 123, JC-1, tetrabromorhodamine 123, rhodamine 6G, TMRM, TMRE, tetramethylrosamine and rhodamine B.

36. The method of claim 29 wherein
(a) said first energy transfer molecule has an excitation maximum at a wavelength of from about 545 to about 560 nm, and an emission maximum at a wavelength of from about 565 to about 625 nm; and
(b) said second energy transfer molecule has an excitation maximum at a wavelength of from about 565 to about 625 nm.

37. The method of claim 36 wherein
(i) said first energy transfer molecule is MitoTracker® Orange CMTMRos; and
(ii) said second energy transfer molecule is $DiOC_2$(5).

38. The method of claim 29 wherein
(a) said first energy transfer molecule has an excitation maximum at a wavelength of from about 495 to about 510 nm, and an emission maximum at a wavelength of from about 510 to about 570 nm; and (b) said second energy transfer molecule has an excitation maximum at a wavelength of from about 510 to about 560 nm.

39. The method of claim 38 wherein
(i) said first energy transfer molecule is a fusion protein, wherein said fusion protein comprises (a) a polypeptide sequence selected from the group consisting of a FLASH protein sequence and a yellow-shifted Green Fluorescent Protein polypeptide sequence having a mutation in one or more of Ser-65, Tyr-66, Ser-72 and Thr-203, and (b) a polypeptide sequence that localizes said fusion protein to a submitochondrial site selected from the group consisting of mitochondrial matrix and mitochondrial inner membrane; and
(ii) said second energy transfer molecule is selected from the group consisting of JC-1, tetrabromorhodamine 123, rhodamine 6G, TMRM, TMRE, tetramethylrosamine, rhodamine B and 4-dimethylamino-tetramethylrosamine.

40. The method of claim 1 wherein a relative amount of the signal generated by energy transfer is detected.

41. The method of claim 1 wherein the signal is detected over a period of time and a rate of change in the signal level is determined.

42. The method of claim 1 wherein the signal is detected over a period of time and integrated.

43. The method of claim 1 wherein membrane potential comprises an electric potential, a pH potential, or both.

44. The method of claim 1 wherein the first and second energy transfer molecules localize to within from about 10 angstroms to about 100 angstroms of each other.

45. The method claim 1 wherein the first and second energy transfer molecules localize to within from about 10 angstroms to about 50 angstroms of each other.

46. The method claim 1 wherein the first and second energy transfer molecules localize to within from about 20 angstroms to about 50 angstroms of each other.

47. The method of any one of claims 1–46 wherein the signal is generated by fluorescence resonance energy transfer.

48. A method for assaying cellular membrane potential, comprising the steps of:
(a) contacting a sample comprising at least one cellular membrane, simultaneously or sequentially and in either order, with each of a first and a second energy transfer molecule that is not endogenous to the sample, wherein:
(i) the first and second energy transfer molecules each localize independently of one another to a same membrane site or to acceptably adjacent membrane sites such that at least one of the energy transfer molecules localizes to a cellular membrane that forms a subcellular compartment, and
(ii) the first energy transfer molecule is an energy donor molecule and the second energy transfer molecule is an energy acceptor molecule;
(b) exciting the energy donor molecule to produce an excited energy donor molecule; and
(c) detecting a signal generated by energy transfer from the first energy transfer molecule to the second energy transfer molecule, wherein the concentration of at least one of the energy transfer molecules in the membrane site changes as a function of membrane potential.

49. The method of claim 48 wherein the first energy transfer molecule localizes to a first membrane site selected from the group consisting of mitochondria, endoplasmic reticulum, Golgi, lysosome and plasma membrane and the second energy transfer molecule localizes to the same membrane site or to an acceptably adjacent membrane site selected from the group consisting of mitochondria, endoplasmic reticulum, Golgi, lysosome and plasma membrane.

50. The method of claim 48 wherein the concentration of the first energy transfer molecule in the first membrane site does not change as a function of membrane potential, and the concentration of the second energy transfer molecule in the membrane site decreases as a function of membrane potential.

51. The method of claim 48 wherein
   (a) the first energy transfer molecule has an excitation maximum at a wavelength of from about 373 nm to about 390 nm, and an emission maximum at a wavelength of from about 400 nm to about 500 nm; and
   (b) the second energy transfer molecule has an excitation maximum at a wavelength of from about 400 nm to about 500 nm.

52. The method of claim 48 wherein
   (a) the first energy transfer molecule has an excitation maximum at a wavelength of from about 425 nm to about 440 nm, and an emission maximum at a wavelength of from about 450 nm to about 535 nm; and
   (b) the second energy transfer molecule has an excitation maximum at a wavelength of from about 450 nm to about 530 nm.

53. The method of claim 48 wherein
   (a) said first energy transfer molecule has an excitation maximum at a wavelength of from about 470 nm to about 500 nm, and an emission maximum at a wavelength of from about 505 nm to about 565 nm; and
   (b) said second energy transfer molecule has an excitation maximum at a wavelength of from about 505 nm to about 565 nm.

54. The method of claim 48 wherein
   (a) said first energy transfer molecule has an excitation maximum at a wavelength of from about 545 to about 560 nm, and an emission maximum at a wavelength of from about 565 to about 625 nm; and
   (b) said second energy transfer molecule has an excitation maximum at a wavelength of from about 565 to about 625 nm.

\* \* \* \* \*